United States Patent [19]

Naka et al.

[11] Patent Number: 5,389,641

[45] Date of Patent: Feb. 14, 1995

[54] FUSED HETEROCYCLIC COMPOUNDS, HAVING ANGIOTENSIN II ANTAGONISTIC ACTIVITY

[75] Inventors: Takehiko Naka; Yoshiyuki Inada, both of Hyogo, Japan

[73] Assignee: Takeda Chemical Industries, Ltd., Osaka, Japan

[21] Appl. No.: 127,356

[22] Filed: Sep. 28, 1993

Related U.S. Application Data

[63] Continuation of Ser. No. 868,841, Apr. 16, 1992, abandoned.

[30] Foreign Application Priority Data

| Apr. 16, 1991 | [JP] | Japan | 3-173473 |
| Jul. 5, 1991 | [JP] | Japan | 3-263341 |
| Sep. 25, 1991 | [JP] | Japan | 3-315629 |

[51] Int. Cl.$^6$ .................. A61K 31/395; C07D 519/00
[52] U.S. Cl. .................... 514/303; 514/262; 514/291; 514/259; 514/343; 514/381; 544/253; 544/284; 546/80; 546/118; 546/271; 548/253; 548/262.4
[58] Field of Search ............... 544/253, 284; 546/80, 546/118, 271; 514/259, 262, 291, 303, 343, 381; 548/253, 262.4

[56] References Cited

U.S. PATENT DOCUMENTS

4,880,804 11/1989 Carini et al. .................. 514/234.5

FOREIGN PATENT DOCUMENTS

| 0028833 | 5/1981 | European Pat. Off. . |
| 0245637 | 11/1987 | European Pat. Off. . |
| 0253310 | 1/1988 | European Pat. Off. . |
| 0291969 | 11/1988 | European Pat. Off. . |
| 0323841 | 7/1989 | European Pat. Off. . |
| 0392317 | 10/1990 | European Pat. Off. . |
| 0399732 | 11/1990 | European Pat. Off. . |
| 0400835 | 12/1990 | European Pat. Off. . |
| 0407102 | 1/1991 | European Pat. Off. . |
| 0411507 | 2/1991 | European Pat. Off. . |
| 0420237 | 4/1991 | European Pat. Off. . |
| 0028834 | 5/1991 | European Pat. Off. . |
| 461040 | 12/1991 | European Pat. Off. . |
| 480204 | 4/1992 | European Pat. Off. . |

*Primary Examiner*—Howard T. Mars
*Assistant Examiner*—Michael B. Hydorn
*Attorney, Agent, or Firm*—Foley & Lardner

[57] ABSTRACT

Fused heterocyclic compounds of the formula (I):

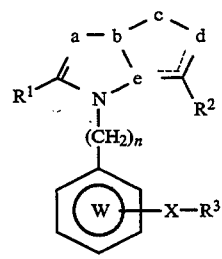

wherein $R^1$ is an optionally substituted hydrocarbon residue which may be attached through a hetero atom; $R^2$ is a group capable of forming an anion or a group convertible thereinto; $R^3$ is an optionally substituted aromatic hydrocarbon or heterocyclic residue which contains at least one hetero atom; X is a direct bond or a spacer having an atomic length of two or less between the $R^3$ group and the ring W group; W is an optionally substituted aromatic hydrocarbon or heterocyclic residue which contains at least one hereto atom; a,c and d are independently selected from the group consisting of one or two optionally substituted carbon atoms and one or two optionally substituted hetero atoms; b and e are independently selected from the group consisting of one optionally substituted carbon atom and one optionally substituted nitrogen atom wherein one of b or e must be nitrogen; the dotted line is a bond to form one double bond; n is an integer of 1 or 2 and when a, which is an optionally substituted carbon atom, is taken together with $R^1$, the following group:

(Abstract continued on next page.)

may form a ring group; provided that when

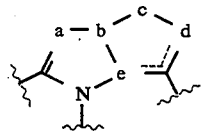

is a benzimidazole, thieno[3,4-d]imidazole, or thieno[2,3-d]imidazole ring, at least one of the group:

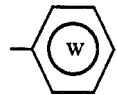

and $R^3$ is an optionally substituted heterocyclic residue; and the pharmaceutically acceptable salts thereof, have potent angiotensin II antagonistic activity and antihypertensive activity, thus being useful as therapeutic agents for treating circulatory system diseases such as hypertensive diseases, heart diseases (e.g. hypercardia, heart failure, cardiac infarction, etc.), strokes, cerebral apoplexy, nephritis, etc.

14 Claims, No Drawings

FUSED HETEROCYCLIC COMPOUNDS, HAVING ANGIOTENSIN II ANTAGONISTIC ACTIVITY

This application is a continuation of Ser. No. 07/868,841 filed Apr. 16, 1992, now abandoned.

FIELD OF THE INVENTION

The present invention relates to novel fused heterocyclic compounds having potent pharmacological actions and intermediates for the preparation thereof. More particularly, the present invention relates to fused heterocyclic compounds having potent anti-hypertensive activity and strong angiotensinII antagonistic activity, which are useful as therapeutic agents for treating circulatory diseases such as hypertensive diseases, heart diseases (e.g. hypercardia, heart failure, cardiac infarction, etc.), strokes, cerebral apoplexy, nephritis, etc.

BACKGROUND OF THE INVENTION

The renin-angiotensin system is involved in the homeostatic function to control systemic blood pressure, the volume of body fluid, balance among the electrolytes, etc., associated with the aldosterone system. Development of angiotensinII converting enzyme inhibitors (ACE inhibitor: this converting enzyme produces angiotensinII which possesses a strong vasoconstrictive action) has clarified the relation between the renin-angiotensin system and hypertension. Since angiotensinII constricts blood vessels to elevate blood pressure via the angiotensinII receptors on the cellular membranes, angiotensinII antagonists, like the ACE inhibitor, would be useful in treating hypertension caused by angiotensinII.

It has been reported that various angiotensinII analogues such as saralasin, [Sar$^1$,Ile$^8$]AII, and the like, possess potent angiotensinII antagonist activity.

It has, however, been reported that, when peptide antagonists are administered parenterally, their actions are not prolonged and, when administered orally, they are ineffective (M. A. Ondetti and D. W. Cushman, Annual Reports in Medicinal Chemistry, 13, 82–91 (1978)).

It would be highly desirable to develop a non-peptide angiotensinII antagonist which overcomes these drawbacks. In the earliest studies in this field, imidazole derivatives having angiotensinII antagonist activity have been disclosed in Japanese Patent Laid Open No. 71073/1981; No. 71074/1981; No. 98270/1982; and No. 157768/1983; U.S. Pat. Nos. 4,355,040; and 4,340,598, etc. Later, improved imidazole derivatives were disclosed in European Patent Laid Open No. 0253310; No. 0291969; No. 0324377; and No. 403158, WO No. 9100277, and Japanese Patent Laid Open No. 23868/1988; and No. 117876/1989. Further, pyrrole, pyrazole, and triazole derivatives are disclosed as angiotensinII antagonists in European Patent Laid Open No. 0323841; and No. 0409332, and Japanese Patent Laid Open No. 287071/1989. Benzimidazole derivatives are disclosed as angiotensinII antagonists in U.S. Pat. No. 4,880,804, European Patent Laid Open No. 0392317, No. 0399732, and No. 0400835, and Japanese Patent Laid Open No. 63264/1991. Azaindene derivatives are disclosed as angiotensinII antagonists in European Patent Laid Open No. 0399731. Pyrimidone derivatives are disclosed as angiotensinII antagonists in European Patent Laid Open No. 0407342. Quinazoline derivatives are disclosed as angiotensinII antagonists in European Patent Laid Open No. 0411766.

It is considered that clinically useful angiotensinII antagonistic compounds for practical use are required to have a prolonged potent angiotensinII antagonistic by oral administration and the activity of even the above disclosed prior art compounds is insufficient for clinical uses.

OBJECT OF THE INVENTION

It is an object of the present invention to provide novel fused heterocyclic compounds having potent anti-hypertensive activity and strong angiotensinII antagonistic action, which are of practical value in clinical use as therapeutic agents.

The present inventors considered that compounds functioning to control the renin-angiotensin system as well as clinically useful for the treatment of circulatory diseases such as hypertensive diseases, heart diseases (e.g. hypercardia, heart failure, cardiac infarction, etc.), strokes, cerebral apoplexy, etc. are required to have potent angiotensinII receptor antagonistic activity and to exert strong oral and long-lasting angiotensinII antagonist action. Extensive investigations were made based on those consideration. As a result of this research, the present inventors have succeeded in synthesizing novel fused heterocyclic compounds (I) possessing highly angiotensinII receptor antagonistic activity as well as exerting prolonged angiotensinII antagonistic and anti-hypertensive action by oral administration thereof and developed the present invention.

SUMMARY OF THE INVENTION

The present invention relates to fused heterocyclic compounds having the formula I:

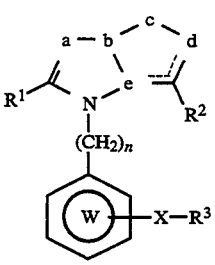

wherein $R^1$ is an optionally substituted hydrocarbon residue which may be attached through a hetero atom; $R^2$ is a group capable of forming an anion or a group convertible thereinto; $R^3$ is an optionally substituted aromatic hydrocarbon or heterocyclic residue which contains at least one hetero atom; X is a direct bond or a spacer having an atomic length of two or less between the $R^3$ group and the ring W group; W is an optionally substituted aromatic hydrocarbon or heterocyclic residue which contains at least one hetero atom; a,c and d are independently selected from the group consisting of one or two optionally substituted carbon atoms and one or two optionally substituted hetero atoms; b and e are independently selected from the group consisting of one optionally substituted carbon atom and one optionally substituted nitrogen atom; the dotted line is a bond to form one double bond; n is an integer of 1 or 2 and when a, which is an optionally substituted carbon atom, is taken together with $R^1$, the following group:

may form a ring group; provided that when

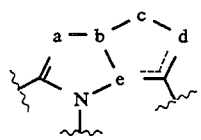

is a benzimidazole, thieno[3,4-d]imidazole, or thieno[2,3-d]imidazole ring, at least one of the group:

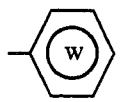

and $R^3$ is an optionally substituted heterocyclic residue; and the pharmaceutically acceptable salts thereof.

These compounds are unexpectedly potent angiotensinII antagonists which are of value in the treatment of circulatory system diseases such as hypertensive diseases, heart diseases, strokes, nephritis, etc.

Another aspect of the present invention relates to pharmaceutical compositions comprising an effective amount of the fused heterocyclic compounds having the formula I and a pharmaceutically acceptable carrier useful in treating circulatory system diseases such as hypertensive diseases, heart diseases, strokes, renal failure, nephritis, etc., and processes for preparing such compounds and compositions.

Still another aspect of the present invention relates to a method for treating said circulatory system diseases of animals, which comprises administering an effective amount of the fused heterocyclic compounds having the formula I or the pharmaceutical composition thereof to said animal.

DETAILED DESCRIPTION OF THE INVENTION

The present invention provides the fused heterocyclic compounds (I) and the pharmaceutically acceptable salts thereof, which possess strong angiotensinII antagonist activity and are of value in the treatment of circulatory diseases such as hypertensive diseases, heart diseases, strokes, cerebral diseases, nephritis, etc., pharmaceutical compositions comprising an effective amount of the fused heterocyclic compounds having the formula I and a pharmaceutically acceptable carrier useful in treating said circulatory diseases, and processes for preparing such compounds and compositions.

The present invention further provides a method for treating said circulatory system diseases of animals, which comprises administering an effective amount of the fused heterocyclic compounds (I) or the pharmaceutical composition thereof to said animal.

With regard to the foregoing formula (I), hydrocarbon residues for $R^1$ include, for example, alkyl, alkenyl, alkynyl, cycloalkyl, aryl, and aralkyl groups. Among them, alkyl, alkenyl, and cycloalkyl groups are preferable. The hydrocarbon residue can be attached through a hetero atom to the ring and may be substituted with one or more substituents such as optionally substituted hydrocarbon residues for $R^1$, which may be attached through a hetero atom.

Alkyl groups for $R^1$ are lower alkyl groups having 1 to about 8 carbon atoms, which may be straight or branched, and include, for example, methyl, ethyl, propyl, isopropyl, butyl, isobutyl, sec-butyl, t-butyl, pentyl, i-pentyl, hexyl, heptyl, octyl, and the like.

Alkenyl groups for $R^1$ are lower alkenyl groups having 2 to about 8 carbon atoms, which may be straight or branched, and include, for example, vinyl, propenyl, 2-butenyl, 3-butenyl, isobutenyl, 2-octenyl, and the like.

Alkynyl groups for $R^1$ are lower alkynyl groups having 2 to about 8 carbon atoms, which may be straight or branched, and include, for example, ethynyl, 2-propynyl, 2-butynyl, 2-pentynyl, 2-octynyl, and the like.

Cycloalkyl groups for $R^1$ are lower cycloalkyl groups having 3 to about 6 carbon atoms, and include, for example, cyclopropyl, cyclobutyl, cyclopentyl, cyclohexyl, and the like.

The above-mentioned alkyl, alkenyl, alkynyl, and cycloalkyl groups may be substituted with hydroxyl, an optionally substituted amino group (e.g. amino, N-lower ($C_{1-4}$) alkylamino such as methylamino and ethylamino, N,N-di-lower ($C_{1-4}$) alkylamino such as dimethylamino and diethylamino, etc.), halogen, a lower ($C_{1-4}$) alkoxy group, a lower ($C_{1-4}$) alklthio group or the like.

Aralkyl groups for $R^1$ include, for example, phenyl-lower ($C_{1-4}$) alkyl such as benzyl, phenethyl, and the like.

Aryl groups for $R^1$ include, for example, phenyl, napthtyl, and the like.

The above-mentioned aralkyl and aryl groups may be substituted with, for example, halogen (e.g. F, Cl, Br, etc.), nitro, an optionally substituted amino group (e.g. amino, N-lower ($C_{1-4}$) alkylamino such as methylamino and ethylamino, N,N-di-lower ($C_{1-4}$) alkylamino such as dimethylamino and diethylamino, etc.), lower ($C_{1-4}$) alkoxy (e.g. methoxy, ethoxy, etc.), lower ($C_{1-4}$) alkylthio (e.g. methylthio, ethylthio, etc.), lower ($C_{1-4}$) alkyl (e.g. methyl, ethyl, etc.), or the like at various positions of the benzene ring.

Among the above-mentioned groups for $R^1$, preferred examples are optionally substituted alkyl and alkenyl groups (e.g. lower ($C_{1-5}$) alkyl and lower ($C_{2-5}$) alkenyl groups optionally substituted with hydroxyl, an amino group, halogen or a lower ($C_{1-4}$) alkoxy group).

The above-mentioned $R^1$ may be attached through a hetero atom (e.g. nitrogen [—N($R^{10}$)— wherein $R^{10}$ is hydrogen or lower ($C_{1-4}$) alkyl], oxygen, sulfur [—S-($O_m$)— wherein m is an integer of 0 to 2], etc.) to the ring. Among such groups for $R^1$, preferred examples are groups containing optionally substituted alkyl and alkenyl groups (i.e. for example, methylamino, ethylamino, propylamino, propenylamino, isopropylamino, allylamino, butylamino, isobutylamino, dimethylamino, methoxy, ethoxy, propoxy, isopropoxy, propenyloxy, allyloxy, butoxy, isobutoxy, sec-butoxy, t-butoxy, 2-butenyloxy, 3-butenyloxy, isobutenyloxy, pentoxy, isopentoxy, hexyloxy, methylthio, ethylthio, propylthio, isopropylthio, allylthio, butylthio, isobutylthio, sec-butylthio, t-butylthio, 2-butenylthio, 3-butenylthio, isobutenylthio, pentylthio, isopentylthio, hexylthio, and the like).

Examples of groups capable of forming an anion and groups convertible thereinto for $R^2$ include carboxyl, tetrazolyl, trifluoromethanesulfonic amide (—NH- $SO_2CF_3$), phosphoric acid, sulfonic acid, cyano, lower ($C_{1-4}$) alkoxycarbonyl, and the like. These groups may be protected with, for example, an optionally substituted lower alkyl group (e.g. lower ($C_{1-4}$) alkyl optionally substituted with lower ($C_{1-4}$) alkoxy, aryl, etc.) or an acyl group (e.g. lower ($C_{2-5}$) alkanoyl, optionally substituted benzoyl, etc.). Such groups may include those which are capable of forming anions or convertible thereinto either chemically or under biological and/or physiological conditions (for example, in vivo reaction such as oxidation-reduction or hydrolysis catalyzed by in vivo enzymes).

Examples of carboxyl, esters thereof or amides thereof for $R^2$ include, for example, groups having the formula: —CO—D wherein D is hydroxyl, optionally substituted amino (e.g. amino, N-lower ($C_{1-4}$) alkylamino, N,N-di-lower ($C_{1-4}$) alkyl amino, etc.), or optionally substituted alkoxy [e.g. lower ($C_{1-6}$) alkoxy optionally substituted with hydroxyl, optionally substituted amino (e.g. amino, dimethylamino, diethylamino, piperidino, morpholino, etc.), halogen, lower ($C_{1-6}$) alkoxy, lower ($C_{1-6}$) alkylthio or optionally substituted dioxolenyl (e.g. 5-methyl-2-oxo-1,3-dioxolen-4-yl, etc.) on the alkyl moiety and groups having the formula: —OCH($R^4$)OCOR$^5$ wherein $R^4$ is hydrogen, straight or branched lower alkyl having 1 to 6 carbon atoms (e.g. methyl, ethyl, n-propyl, isopropyl, n-butyl, isobutyl, t-butyl, n-pentyl, isopentyl, neopentyl, etc.), or cycloalkyl having 3 to 8 carbon atoms (e.g. cyclopentyl, cyclohexyl, cycloheptyl, etc.) and $R^5$ is straight or branched lower alkyl having 1 to 6 carbon atoms (e.g. methyl, ethyl, n-propyl, isopropyl, n-butyl, isobutyl, sec-butyl, t-butyl, n-pentyl, isopentyl, neopentyl, etc.), straight or branched lower alkenyl having 2 to about 8 carbon atoms (e.g. vinyl, propenyl, 2-butenyl, 3-butenyl, isobutenyl, octenyl, etc.), cycloalkyl having 3 to 8 carbon atoms (e.g. cyclopentyl, cyclohexyl, cycloheptyl, etc.), lower ($C_{1-3}$) alkyl (e.g. methyl, ethyl, n-propyl, isopropyl, etc.) which is substituted with optionally substituted aryl (e.g. phenyl, etc.) or cycloalkyl having 3 to 8 carbon atoms (e.g. benzyl, p-chlorobenzyl, phenethyl, cyclopentylmethyl, cyclohexylmethyl, etc.), lower ($C_{2-3}$) alkenyl (e.g. vinyl, propenyl, allyl, isopropenyl, etc.) which is substituted with optionally substituted aryl (e.g. phenyl, etc.) or cycloalkyl having 3 to 8 carbon atoms (e.g. cinnamyl, etc.), optionally substituted aryl (e.g. phenyl, p-tolyl, naphthyl, etc.), straight or branched lower alkoxy having 1 to 6 carbon atoms (e.g. methoxy, ethoxy, n-propoxy, isopropoxy, n-butoxy, isobutoxy, sec-butoxy, t-butoxy, n-pentyloxy, isopentyloxy, neopentyloxy, etc.), straight or branched lower alkenyloxy having 2 to about 8 carbon atoms (e.g. allyloxy, isobutenyloxy, etc.), cycloalkyloxy having 3 to 8 carbon atoms (e.g. cyclopentyloxy, cyclohexyloxy, cycloheptyloxy, etc.), lower ($C_{1-3}$) alkoxy (e.g. methoxy, ethoxy, n-propoxy, isopropoxy, etc.) which is substituted with optionally substituted aryl (e.g. phenyl, etc.) or cycloalkyl having 3 to 8 carbon atoms (e.g. benzyloxy, phenethyloxy, cyclopentylmethyloxy, cyclohexylmethyloxy, etc.), lower ($C_{2-3}$) alkenyloxy (e.g. vinyloxy, propenyloxy, allyloxy, isopropenyloxy, etc.) which is substituted with optionally substituted aryl (e.g. phenyl, etc.) or cycloalkyl having 3 to 8 carbon atoms (e.g. cinnamyloxy, etc.), optionally substituted aryloxy (e.g. phenoxy, p-nitrophenoxy, naphthoxy, etc.)]. Examples of groups for $R^2$ may include groups capable of forming an anion and groups convertible thereinto such as tetrazolyl groups optionally protected with optionally substituted lower alkyl such as lower ($C_{1-4}$) alkyl and lower ($C_{1-4}$) alkoxy lower ($C_{1-4}$) alkyl or acyl such as lower ($C_{2-5}$) alkanoyl and optionally substituted benzoyl, trifluoromethanesulfonic amide, phosphoric acid, sulfonic acid, and the like. Examples of substituents for $R^2$ include —COOH and salts thereof, —COOMe, —COOEt, —COOtBu, —COOPr, pivaloyloxymethoxycarbonyl, 1-(cyclohexyloxycarbonyloxy)ethoxycarbonyl, 5-methyl-2-oxo-1,3-dioxolen-4-ylmethyloxycarbonyl, acetoxymethyloxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetyloxy)ethoxycarbonyl, 1-(isobutyryloxy)ethoxycarbonyl, cyclohexylcarbonyloxymethoxycarbonyl, benzoyloxymethoxycarbonyl, cinnamyloxycarbonyloxymethoxycarbonyl, cyclopentylcarbonyloxymethoxycarbonyl, etc. Such groups may include those which are capable of forming anions (e.g. —COO⁻, derivatives thereof, etc.) or convertible thereinto either chemically or under biological and/or physiological conditions (for example, in vivo reaction such as oxidation-reduction or hydrolysis catalyzed by in vivo enzymes).

$R^2$ can be carboxyl, the anion therefrom, or its prodrug form. $R^2$ may include chemically or biologically in vivo convertible groups.

The compounds wherein $R^2$ is a group capable of forming an anion or convertible thereinto chemically (e.g. by oxidation, reduction or hydrolysis) (for example, an optionally protected tetrazolyl group (e.g. a group having the formula:

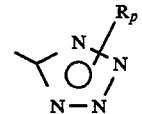

wherein Rp is methyl, triphenylmethyl, 2-tetrahydropyranyl, tert-butyl, methoxymethyl, ethoxymethyl, or optionally substituted benzyl such as p-methoxybenzyl and p-nitrobenzyl), cyano and the like), are useful as synthetic intermediates.

Among the above-mentioned groups for $R^2$, preferred examples are carboxyl, esters thereof (e.g. methyl ester, ethyl ester, the ester residue of the above-mentioned formula: —OCH($R^4$)OCOR$^5$, etc.), optionally protected tetrazolyl groups, carboaldehyde, hydroxymethyl, and the like.

$R^3$ represents an optionally substituted aromatic hydrocarbon or heterocyclic residue which may contain at least one hetero atom. The aromatic hydrocarbon and heterocyclic residues may include aromatic groups such as phenyl, cyclic groups containing only the same hetero atoms or cyclic groups containing two or more different heteroatoms, e.g. heterocyclic groups having a single or fused ring with 4 to 7 ring members in each ring and having one or more hetero atoms in each ring independently selected from oxygen, nitrogen and sulfur. Examples of the heterocyclic group for $R^3$ include pyridyl, pyrimidinyl, pyridazinyl, pyrazinyl, thienyl, furyl, pyrrolyl, imidazolyl, pyrazolyl, isothiazolyl, isoxazolyl, benzofuranyl, isobenzofuranyl, indolizinyl, isoindolyl, 3H-isoindolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, pteridinyl, oxazolyl, thiazolyl, oxadiazolyl, thiadiazolyl, triazolyl, tetrazolyl, triazinyl, oxotriazinyl, tetrazolo[1,5-b]pyridazinyl, triazolo[4,5-b]pyridazinyl, pyrrolidinyl, piperidyl, pyranyl, thiopyranyl, oxazinyl, morpholinyl, thiazinyl, and piperazinyl. A preferred example of $R^3$ is phenyl.

The above-mentioned aromatic hydrocarbon and heterocyclic residues for $R^3$ are optionally substituted with $R^6$. $R^6$ may include groups capable of forming an anion and groups convertible thereinto such as carboxyl, tetrazolyl, trifluoromethanesulfonic amide (—NHSO$_2$CF$_3$), phosphoric acid, sulfonic acid, cyano, lower (C$_{1-4}$) alkoxycarbonyl, and the like. These groups may be protected with, for example, an optionally substituted lower alkyl group (e.g. lower (C$_{1-4}$) alkyl such as methyl and ethyl, lower (C$_{1-4}$) alkyl optionally substituted with lower (C$_{1-4}$) alkoxy or aryl (e.g. phenyl), the above-mentioned group: —OCH(R$^4$)OCOR$^5$, etc.) or an acyl group (e.g. lower (C$_{2-5}$) alkanoyl, optionally substituted benzoyl, etc.).

The above-mentioned aromatic hydrocarbon and heterocyclic residues for $R^3$ may optionally contain substitution in addition to the $R^6$ group and such substituents include halogen (e.g. F, Cl, Br, etc.); nitro; cyano; lower (C$_{1-4}$) alkoxy (e.g. methoxy, ethoxy, etc.), an optionally substituted amino group (e.g. amino, N-lower (C$_{1-4}$) alkylamino such as methylamino and ethylamino, N,N-di-lower (C$_{1-4}$) alkylamino such as dimethylamino and diethylamino, etc.), lower (C$_{1-4}$) alkylthio (e.g. methylthio, ethylthio, etc.), lower (C$_{1-4}$) alkyl (e.g. methyl, ethyl, etc.), or the like.

The compounds wherein $R^6$ is a group capable of forming an anion or convertible thereinto chemically (e.g. by oxidation, reduction or hydrolysis) [for example, an optionally protected tetrazolyl group (e.g. a tetrazolyl group protected by methyl, triphenylmethyl, 2-tetrahydropyranyl, tert-butyl, methoxymethyl, ethoxymethyl, or optionally substituted benzyl such as p-methoxybenzyl and p-nitrobenzyl), cyano and the like], are useful as synthetic intermediates.

W represents an optionally substituted aromatic hydrocarbon or heterocyclic residue which contains at least one hereto atom. The aromatic hydrocarbon and heterocyclic residues may include aromatic groups such as phenyl, cyclic groups containing only the same hereto atoms or cyclic groups containing two or more different heteroatoms, e.g. heterocyclic groups having a single or fused ring with 4 to 7 ring members in each ring and having one or more hereto atoms in each ring independently selected from oxygen, nitrogen and sulfur. Examples of the heterocyclic group for W include pyridyl, pyrimidinyl, pyridazinyl, pyrazinyl, thienyl, furyl, pyrrolyl, imidazolyl, pyrazolyl, isothiazolyl, isoxazolyl, benzofuranyl, isobenzofuranyl, indolizinyl, isoindolyl, 3H-isoindolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, pteridinyl, oxazolyl, thiazolyl, oxadiazolyl, thiadiazolyl, triazolyl, tetrazolyl, triazinyl, oxotriazinyl, tetrazolo[1,5-b]pyridazinyl, triazolo[4,5-b]pyridazinyl, pyrrolidinyl, piperidyl, pyranyl, thiopyranyl, oxazinyl, morpholinyl, thiazinyl, and piperazinyl. A preferred example of W is phenyl.

The above-mentioned aromatic hydrocarbon and heterocyclic residues for W are optionally substituted with, for example, halogen (e.g. F, Cl, Br, etc.); nitro; cyano; lower C$_{1-4}$) alkoxy (e.g. methoxy, ethoxy, etc.), an optionally substituted amino group (e.g. amino, N-lower (C$_{1-4}$) alkylamino such as methylamino and ethylamino, N,N-di-lower (C$_{1-4}$) alkylamino such as dimethylamino and diethylamino, etc.), lower (C$_{1-4}$) alkylthio (e.g. methylthio, ethylthio, etc.), lower (C$_{1-4}$) alkyl (e.g. methyl, ethyl, etc.), or the like.

X shows that the adjacent ring W is bonded to the $R^3$ group directly or through a spacer with an atomic chain of 2 or less. As the spacer, any one can be used, so long as it is a divalent chain in which the number of atoms constituting the straight chain is 1 or 2, and it may have a side chain.

Examples of such spacers include lower (C$_{1-4}$) alkylene,

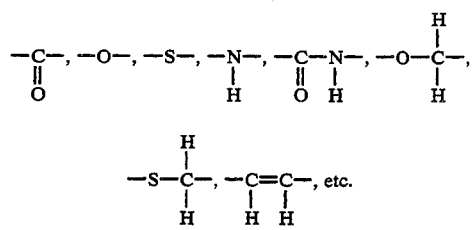

The most preferred X is a chemical bond between the W ring and the $R^3$ group. n is an integer of 1 or 2 Among the groups of the formula:

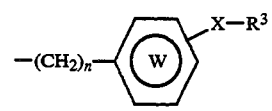

wherein $R^3$, W, X and n are of the same meaning as defined above, preferred examples are

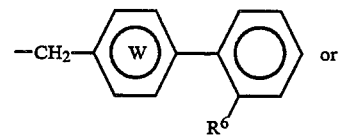

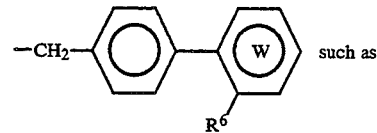

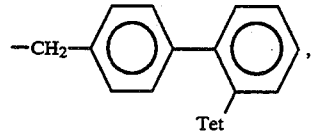

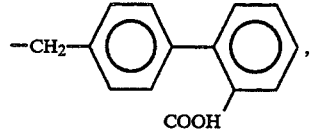

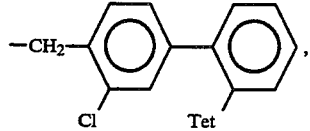

-continued
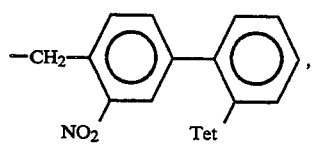
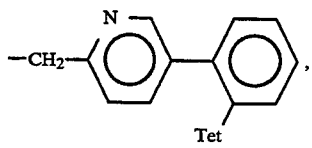
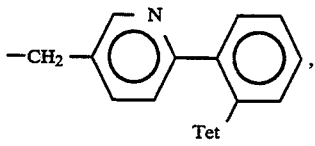
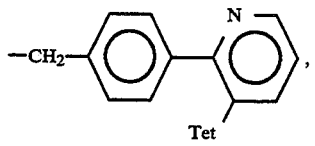
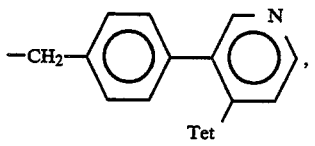
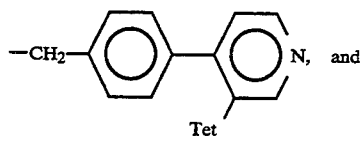 and
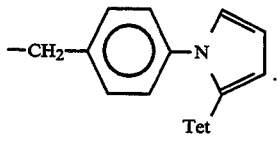
In an embodiment of the present invention, representative examples of the heterocyclic group represented by the following formula:
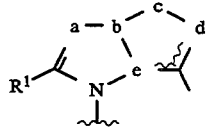   II
may include:
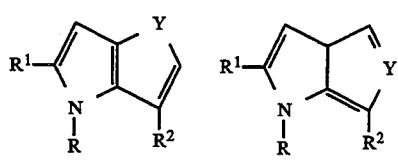
-continued
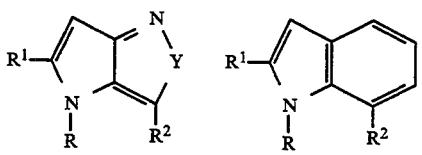
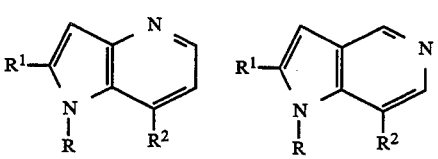
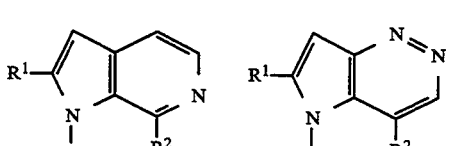
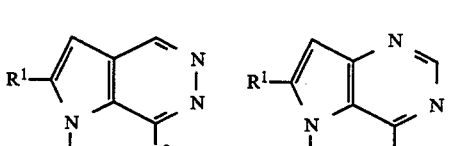
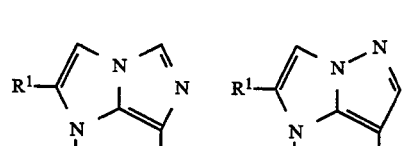
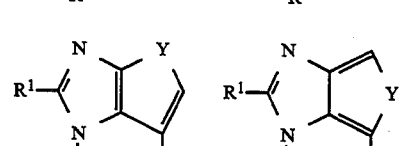
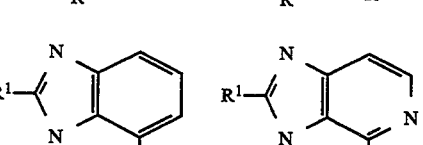
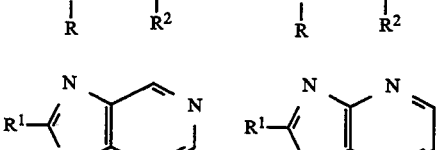
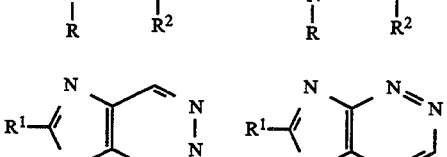
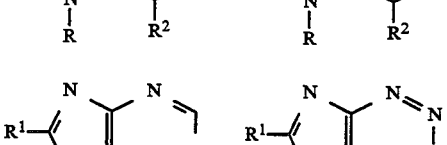

-continued
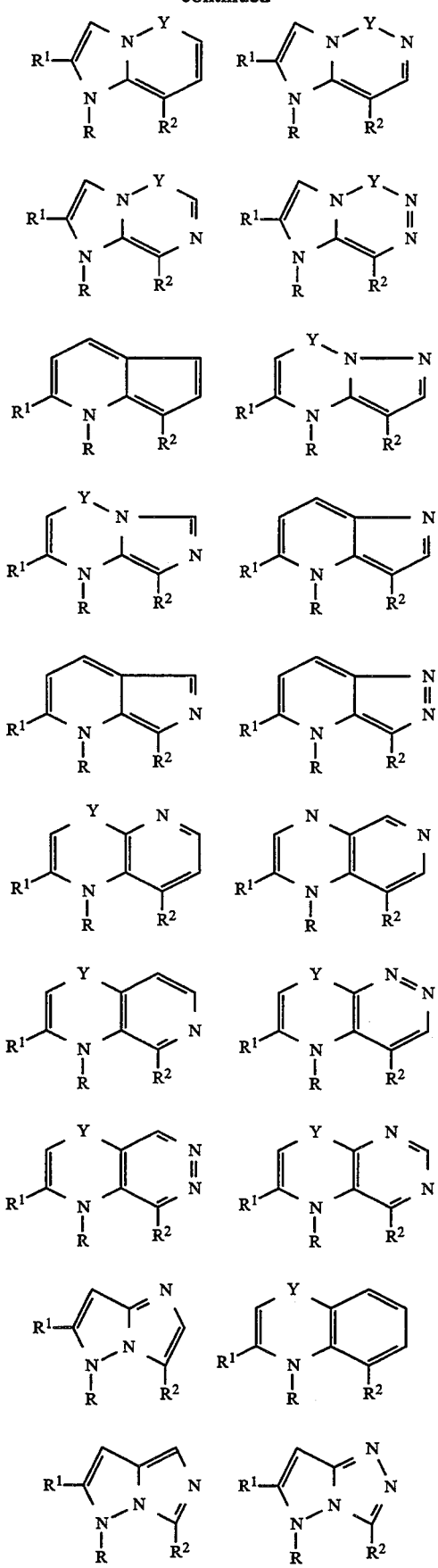
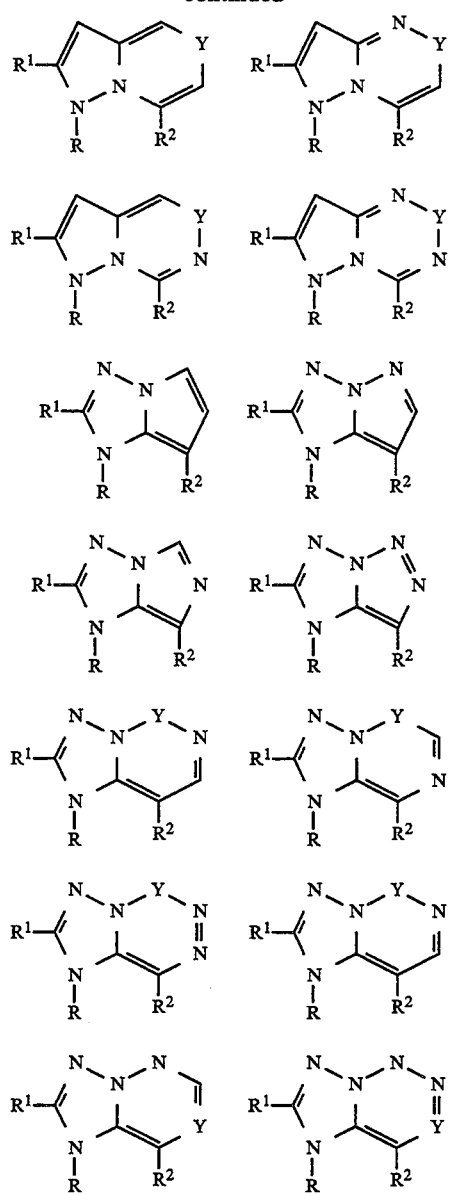
In the above-mentioned formulas, $R^1$ and $R^2$ are of the same meaning as described above, R is of the same meaning as described in the above-mentioned formula:
, and
Y is —CH$_2$—, —CO—, —O—, —S— or —NR$^{11}$— wherein R$^{11}$ is hydrogen or C$_{1-4}$ lower alkyl.
The group:
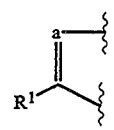

may form a fused heterocyclic ring. Examples of such resulting tricyclic fused heterocyclic rings represented by the formula:

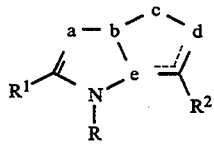

may include:

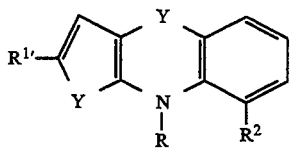

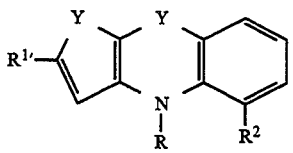

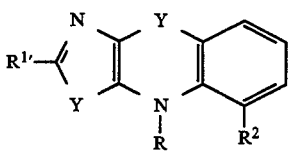

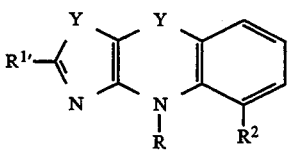

When $R^1 =H$, the compounds having the formula (I) [Compound (I)] may exist in two tautomeric forms.

When the compounds of the present invention have several asymetric carbon atoms, they can thus exist in several stereochemical forms. The invention includes the mixture of isomers and the individual stereoisomers. It is intended that the present invention includes geometrical isomers, rotational isomers, enantiomers, racemates, and diastereomers.

The compounds of the present invention can exist in any prodrug form of those wherein $R^2$ is carboxyl or the anion therefrom.

Among the compounds represented by the above formula (I), a preferred embodiment of the invention is a compound of the formula:

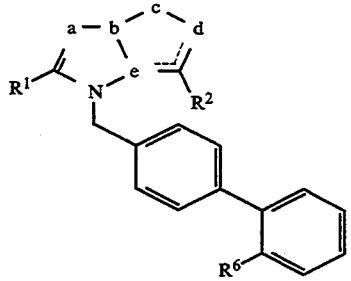

I' wherein $R^1$ is an optionally substituted lower ($C_{1-5}$) alkyl group (inter alia lower ($C_{2-4}$) alkyl wherein the methylene group may be replaced with a hetero atom (e.g. O, N, S, etc.); $R^2$ is —CO—D' wherein D' is hydroxyl, amino, N-lower ($C_{1-4}$) alkylamino, N,N-dilower ($C_{1-4}$) alkyl amino, or lower ($C_{1-4}$) alkoxy optionally substituted with hydroxyl, amino, halogen, lower ($C_{1-4}$) alkoxy, lower ($C_{2-6}$) alkanoyloxy (e.g. acetyloxy, pivaloyloxy, etc.) or 1-lower ($C_{1-6}$) alkoxycarbonyloxy (e.g. methoxycarbonyloxy, ethoxycarbonyloxy, cyclohexyloxycarbonyloxy, etc.) on the alkyl moiety, or tetrazolyl optionally protected with an optionally substituted lower ($C_{1-4}$) alkyl or acyl group (e.g. lower ($C_{2-5}$) alkanoyl, benzoyl, etc.); $R^6$ is tetrazolyl optionally protected with an optionally substituted lower ($C_{1-4}$) alkyl (e.g. methyl, triphenylmethyl (trityl), methoxymethyl, ethoxymethyl, p-methoxybenzyl, p-nitrobenzyl, etc.) or acyl group (e.g. lower ($C_{2-5}$) alkanoyl, benzoyl, etc.), or carboxyl optionally protected with an optionally substituted lower ($C_{1-4}$) alkyl group (e.g. methyl, triphenylmethyl (trityl), methoxymethyl, ethoxymethyl, p-methoxybenzyl, p-nitrobenzyl, etc.); the fused heterocyclic ring of the formula:

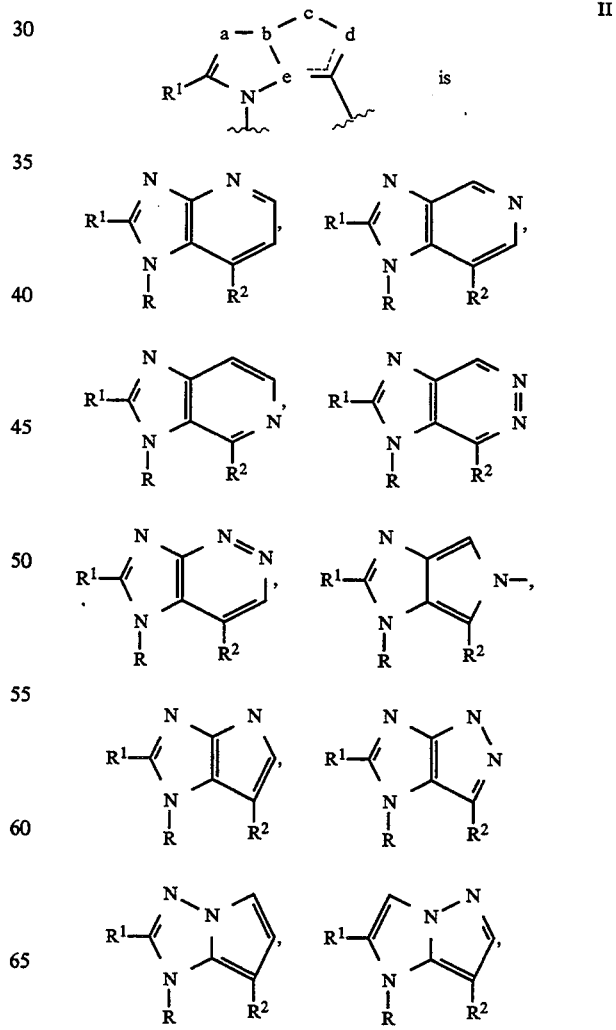

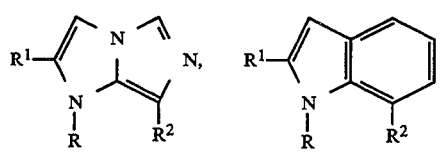 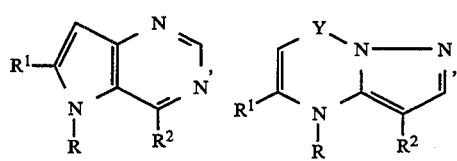 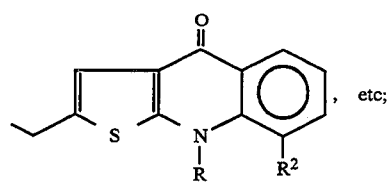

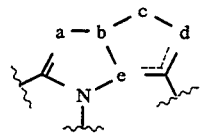, etc;

and the pharmaceutically acceptable salt thereof.
When the group of the formula:

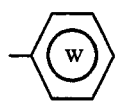

is a benzimidazole, thieno[3,4-d]imidazole, or thieno[2,3-d]imidazole ring, at least one of the group:

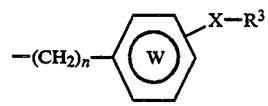

and $R^3$ is an optionally substituted heterocyclic residue; and preferred examples of the groups of the formula:

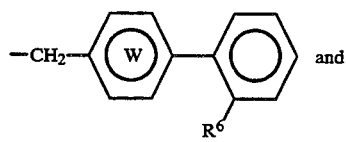

in the compound of the formula (I), are

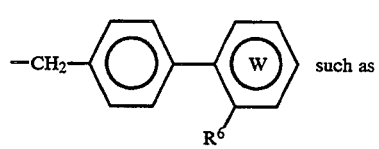 and such as

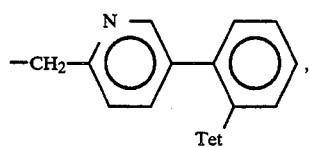,

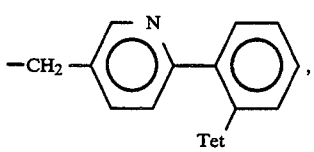,

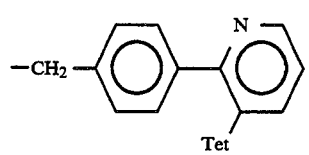,

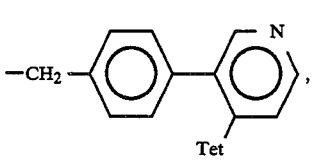,

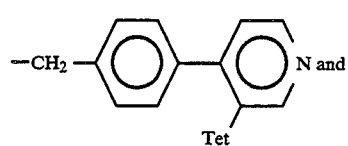 N and

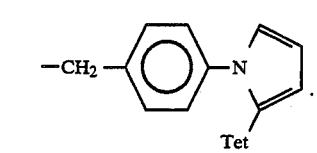.

The compounds (I) of the present invention may be prepared by several reaction schemes, as illustrated below for a preferred compound.

Scheme A

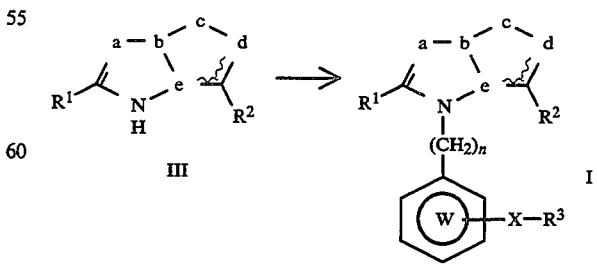

wherein $R^1$, $R^2$, $R^3$, W, X, a, b, c, d, e and n have the above-defined meanings.

Scheme B

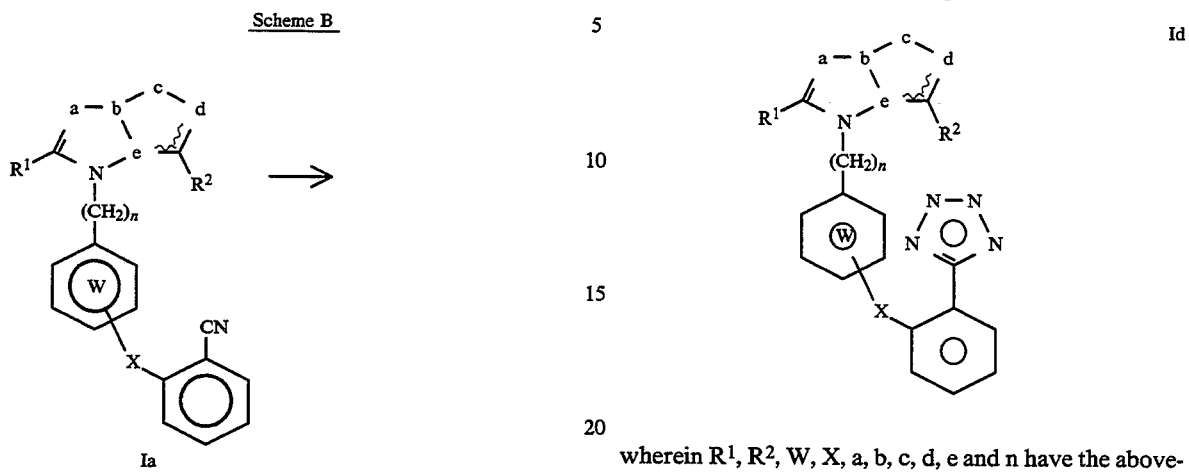

wherein $R^1$, $R^2$, W, X, a, b, c, d, e and n have the above-defined meanings.

Scheme C

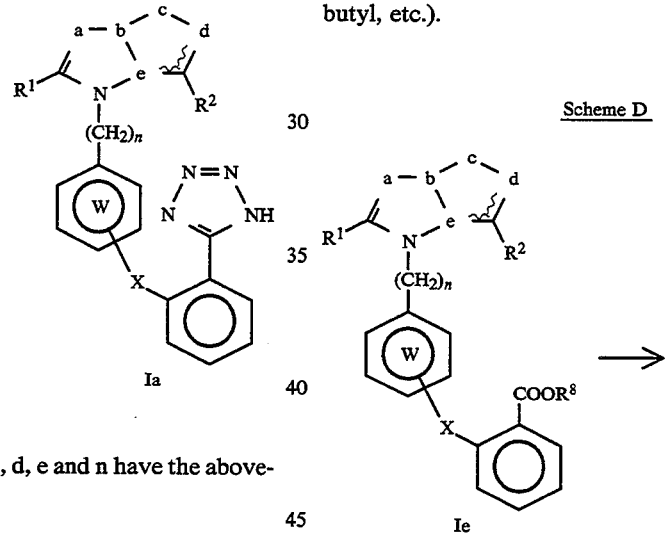

-continued
Scheme C

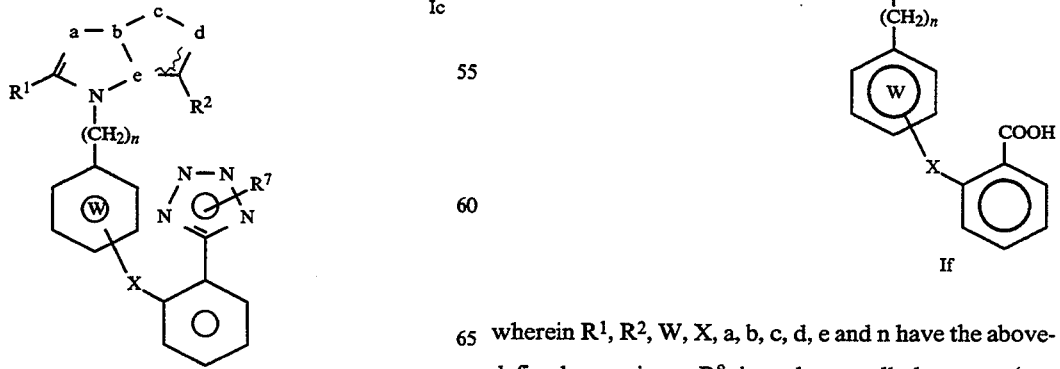

wherein $R^1$, $R^2$, W, X, a, b, c, d, e and n have the above-defined meanings, $R^7$ is a protective group (e.g. triphenylmethyl, 2-tetrahydropyranyl, methoxymethyl, tert-butyl, etc.).

Scheme D wherein $R^1$, $R^2$, W, X, a, b, c, d, e and n have the above-defined meanings, $R^8$ is a lower alkyl group (e.g. methyl, ethyl, isopropyl, tert-butyl, etc.).

Scheme E

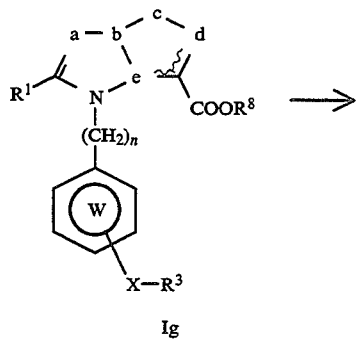

Ig

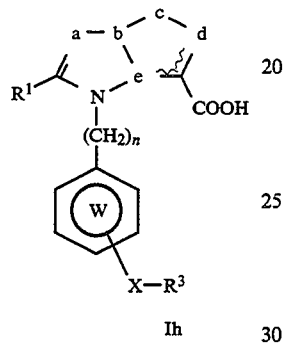

Ih wherein $R^1$, $R^3$, $R^5$, $R^8$, W, X, a, b, c, d, e and n have the above-defined meanings.

Scheme F

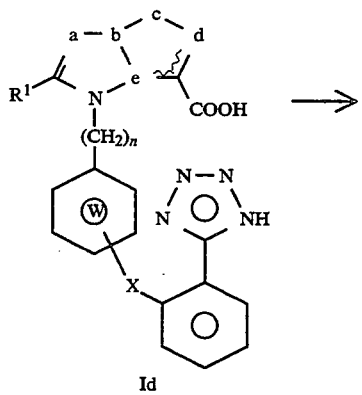

Id

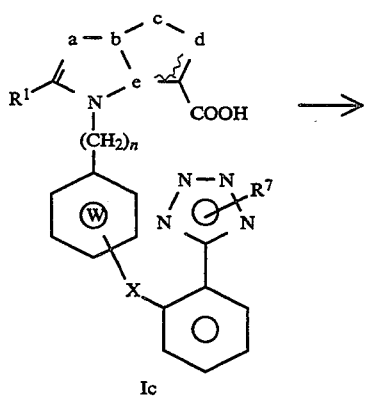

Ic

-continued
Scheme F

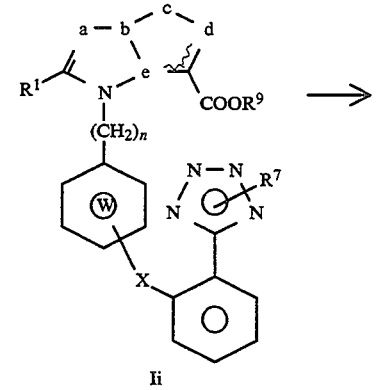

Ii

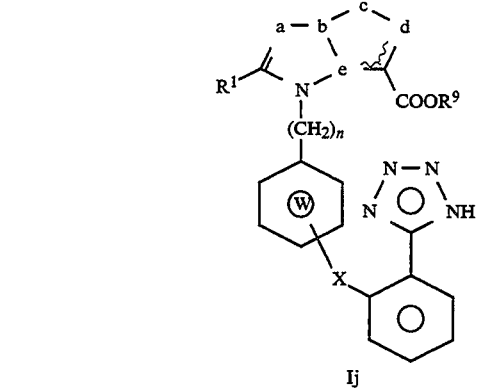

Ij wherein $R^1$, $R^7$, W, X, a, b, c, d, e and n have the above-defined meanings, $R^9$ is —CH($R^4$)OCOR$^5$ wherein each group has the above-defined meaning.

The reaction as illustrated in Scheme A is an alkylation using an alkylating agent in the presence of a base. One molar portion of the compound (III) is employed with approximately 1 to 3 moles of the base and 1–3 moles of the alkylating agent. The reaction is conventionally conducted in solvents such as dimethylformamide, dimethylacetamide, dimethylsulfoxide, acetonitrile, acetone, ethylmethylketone, and the like. Examples of such bases include sodium hydride, potassium t-butoxide, potassium carbonate, sodium carbonate, and the like. Examples of such alkylating agents include substituted halides (e.g. chlorides, bromides, iodides, and the like), substituted sulfonate esters (e.g. p-toluenesulfonate esters, and the like), etc. The reaction conditions may vary depending on the combination of the base and the alkylating agent. Advantageously, the reaction is carried out at ice-cooling to room temperature for about 1–10 hours.

In the said alkylation, a mixture of plural isomers, is usually obtained depending on the position of the N atom to be alkylated. While the production ratio of resultant compounds varies with the reaction conditions employed and the substituents on the fused heterocyclic ring, these compounds can be obtained easily as pure products respectively by conventional isolation and/or purification methods (e.g. recrystallization, column chromatography and the like).

The nitrile compound (Ia) is reacted with various azides to form the tetrazole compound (Ib) as illustrated in Scheme B. One molar portion of the compound (Ia) is employed with 1–5 moles of the azide. The reaction is conventionally conducted in solvents such as dimethylformamide, dimethylacetamide, toluene, benzene, and the like. Examples of such azides include trialkyltin azide (e.g. trimethyltin azide, tributyltin azide, triphenyltin azide, etc.), hydrogen azide and ammonium salts thereof, and the like. In the case where the organotin azide compound is employed, 1–4 moles of the azide are employed per compound (Ia) and the reaction is carried out in toluene or benzene by heating under reflux for a period of 1–4 days. When the hydrogen azide or its ammonium salt is used, 1–5 moles of sodium azide and ammonium chloride or tertiary amine (e.g. triethylamine, tributylamine, etc.) are employed per compound (Ia) and the reaction is conducted in dimethylformamide at about 100° C.–120° C. for about 1–4 days. During this reaction, it is preferable to facilitate the reaction by adding an appropriate amount of sodium azide and ammonium chloride. In this case, improvement may sometimes be observed in reaction time and yield by the addition of the azide compound in suitable fractions.

The protected tetrazole derivative (Ic) is deprotected to give Compound (Id) as depicted in Scheme C. Conditions of the deprotection depend on the protective group ($R^7$) used. When $R^7$ is triphenylmethyl, 2-tetrahydropyranyl, methoxymethyl, ethoxymethyl or the like, it is convenient to conduct the reaction in an aqueous alcohol (e.g. methanol, ethanol, etc.) containing about 0.5N to 2N hydrochloric acid or acetic acid at about room temperatures for about 1 to 10 hours.

The ester (Ie) is hydrolyzed in the presence of alkali to give the carboxylic acid (If) as illustrated in Scheme D. This reaction is conducted usually in a solvent such as aqueous alcohol (e.g. methanol, ethanol, methyl cellosolve, etc.) by using alkali in an amount of about 1 to 3 mol. relative to 1 mol. of Compound (Ie). Examples of such alkalis include sodium hydroxide, potassium hydroxide, etc. The reaction is conducted at temperatures ranging from room temperature to about 100° C. for about 1 to 10 hours, preferably around the boiling point of the solvent for about 2 to 5 hours.

The carboxylic ester (Ig) is hydrolyzed in the presence of alkali to give the carboxylic acid (Ih) as illustrated in Scheme E. This reaction is conducted usually in a solvent such as aqueous alcohol (e.g. methanol, ethanol, methyl cellosolve, etc.) by using alkali in an amount of about 1 to 3 mol. relative to 1 mol. of Compound (Ig). Examples of such alkalis include sodium hydroxide, potassium hydroxide, etc. The reaction is conducted at temperatures ranging from room temperature to about 100° C. for about 1 to 10 hours, preferably around the boiling point of the solvent for about 2 to 5 hours.

The compound (Ij) is prepared by protecting the tetrazole group in the presence of a base, and then the carboxyl group to give the ester compound (Ii), followed by removing the protective group under acid conditions as illustrated in Scheme F. In the reaction to obtain Compound (Ic) from Compound (Id), an alkylating agent is used in an amount of about 1 to 1.5 mol. relative to 1 mol. of Compound (In). Examples of the solvents to be used for the reaction include halogenated hydrocarbons such as chloroform, methylene chloride and ethylene chloride, ethers such as dioxane and tetrahydrofuran, acetonitrile, pyridine, etc. Examples of such bases include potassium carbonate, sodium carbonate, triethylamine, pyridine, etc. Examples of such alkylating agents include halides such as triphenylmethyl chloride and methoxymethyl chloride, etc. While reaction conditions vary with combinations of the base and the alkylating agent employed, it is preferable to conduct the reaction by using triphenylmethyl chloride at temperatures ranging from ice-cooling to room temperature for about 1 to 3 hours in methylene chloride in the presence of triethylamine. In the reaction for producing Compound (Ii) from Compound (Ic) thus obtained, the alkylating agent is used in an amount of about 1 to 3 mol. relative to 1 mol. of Compound (Ic). Examples of the reaction solvent include amides such as dimethylformamide and dimethylacetamide, acetonitrile, dimethylsulfoxide, acetone, ethyl methyl ketone, etc. Examples of the base include potassium carbonate, sodium carbonate, sodium hydride, potassium t-butoxide, etc. Examples of such alkylating agents include halides such as cyclohexyl 1-iodoethyl carbonate, ethyl 1-iodoethyl carbonate, pivaloyloxymethyl iodide, etc. While reaction conditions vary with combinations of the base and the alkylating agent employed, it is preferable to subject Compound (Ii) to reaction in DMF, by adding the alkylating agent in the presence of potassium carbonate, at about room temperatures for about 30 minutes to one hour.

The reaction for deprotecting Compound (Ii) thus obtained is conducted preferably in a manner similar to the reaction (C). When a trityl group is used as the protecting group of the tetrazole group, it is preferable to conduct the reaction in methanol or ethanol, while adding 1N-HCl, at about room temperatures for about 30 minutes to one hour.

The reaction products obtained as above by the reaction processes (A) to (F), can be easily isolated and/or purified by or according to conventional methods such as, for example, evaporation of solvents, extraction by water or organic solvents, concentration, neutralization, recrystallization, distillation, column chromatography and the like. The compounds (I) thus produced via the reaction processes as depicted in Schemes A to F can be isolated and/or purified from the reaction mixture according to conventional methods such as, for example, recrystallization and column chromatography, to obtain a crystalline product.

The compounds obtained as above by the reaction processes (A) to (F), may be in the form of solvates or salts (including addition salts) derived from pharmaceutically or physiologically acceptable acids or bases. These salts include but are not limited to the following: salts with inorganic acids such as hydrochloric acid, hydrobromic acid, hydroiodic acid, sulphuric acid, nitric acid, phosphoric acid and, as the case may be, such organic acids as acetic acid, oxalic acid, succinic acid, citric acid, ascorbic acid, lactic acid, p-toluenesulfonic acid, methanesulfonic acid, fumaric acid, tartaric acid and maleic acid. Other salts include salts with ammonium, alkali metals or alkaline earth metals, such as sodium, potassium, calcium or magnesium or with organic bases (e.g. trialkylamines, dibenzylamine, ethanolamine, triethanolamine, N-methylmorpholine, etc).

And, by conventional means, the compounds (I) can be formed as salts with non-toxic, physiologically or pharmaceutically acceptable acids or bases, for example salts with an inorganic acid such as hydrochloride, sulfate or nitrate, and, depending on compounds, salts with an organic acid such as acetate, oxalate, succinate or maleate, salts with an alkali metal such as sodium salt or potassium salt, or salts with an alkaline earth metal such as calcium salt.

Among the starting compounds (IV), the compound (IV) wherein n denotes 1, i.e. the compound (IVa) is commercially available, or can be readily obtained also by subjecting Compound (V) to halogenomethylation in accordance with the methods described in literature references, for example;
1) J. R. E. Hoover, A. W. Chow, R. J. Stedman, N. M. Hall, H. S. Greenberg, M. M. Dolan and R. J. Feriauto, J. Med. Chem., 7, 245 (1964),
2) R. J. Stedman, J. R. E. Hoover, A. W. Chow, M. M. Dolan, N. M. Hall and R. J. Feriauto, J. Med. Chem., 7, 251 (1964),
3) H. Gilman and R. D. Gorsich, J. Am. Chem. Soc., 78, 2217 (1956),
4) M. Orebin and E. Oscar Woolfolk, J. Am. Chem. Soc., 67, 122 (1945), etc.

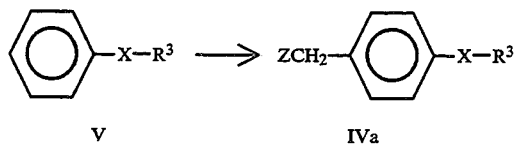

[wherein each group is of the same meaning as defined above].

Further, among the starting compounds (IV), the compound (IV) wherein n denotes 2, i.e. the compound (IVb) can be obtained from the compound (IVa) in accordance with the reaction (G).

Scheme G

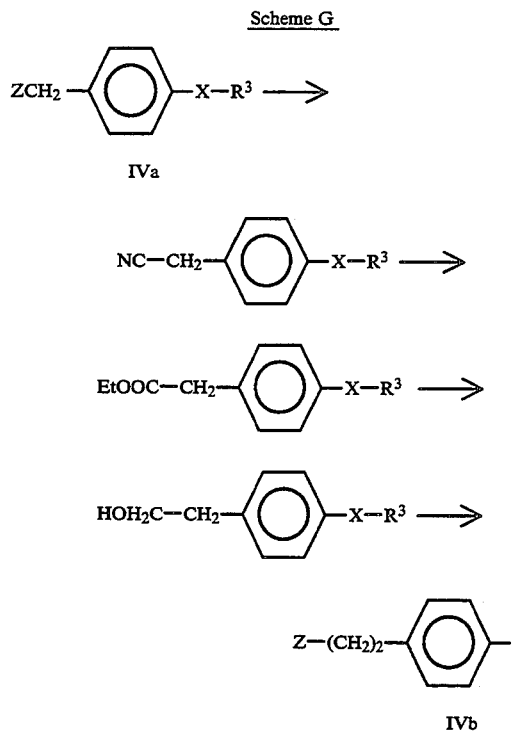

[wherein each group is of the same meaning as defined above].

The compounds and the salts thereof thus produced are less toxic, strongly inhibit the vasoconstrictive and hypertensive actions of angiotensin II, exert a hypotensive effect in animals, in particular mammals (e.g. human, dog, rabbit, rat, etc.), and therefore they are useful as therapeutics for not only hypertension but also circulatory diseases such as heart failure (hypertrophy of the heart, cardiac insufficiency, cardiac infarction or the like), strokes, cerebral apoplexy, nephropathy and nephritis. The compounds (I) and salts thereof according to the present invention strongly inhibit vasoconstriction and hypertension derived by angiotensin II and therefore possess potent anti-hypertensive activity in animals, more specifically mammals (e.g. humans, dogs, pigs, rabbits, rats, etc.). Further, the compounds (I) and salts thereof according to the present invention are of quite low toxicity and clinically useful in treating not only hypertension but also circulatory system diseases such as heart and brain diseases, strokes, renal failures, nephritis and the like.

For therapeutic use, the compounds (I) and salts thereof can be orally, parenterally, by inhalation spray, rectally, or topically administered as pharmaceutical compositions or formulations (e.g. powders, granules, tablets, pills, capsules, injections, syrups, emulsions, elixirs, suspensions, solutions and the like) comprising at least one such compound alone or in admixture with pharmaceutically acceptable carriers, adjuvants, vehicles, excipients and/or diluents. The pharmaceutical compositions can be formulated in accordance with conventional methods. The term parenteral as used herein includes subcutaneous injections, intravenous, intramuscular, intraperitoneal injections, or infusion techniques. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a non-toxic parenterally acceptable diluent or solvent, for example, as a solution in water. Among the acceptable vehicles or solvents that may be employed are water, Ringer's solution, and isotonic sodium chloride solution. In addition, sterile, fixed oils are conventionally employed as a solvent or suspending medium. For this purpose any bland fixed oil or fatty acid may be employed including natural, synthetic, or semi-synthetic fatty oils or acids, and natural, synthetic, or semi-synthetic mono-, di-, or triglycerides.

Suppositories for rectal administration of the drug can be prepared by mixing the drug with a suitable non-irritating excipient such as cocoa butter and polyethylene glycols which are solid at ordinary temperatures but liquid at the rectal temperature and will therefore melt in the rectum and release the drug. Solid dosage forms for oral administration may include powders, granules, tablets, pills, and capsules as mentioned above. In such solid dosage forms, the active compound may be admixed with at least one additive such as sucrose, lactose, celluloses, mannitol, maltitol, dextran, starches, agars, alginates, chitins, chitosans, pectins, tragacanth gums, arabic gums, gelatins, collagens, casein, albumin, and synthetic or semi-synthetic polymers or glycerides. Such dosage forms may also comprise, as is normal practice, additional substances other than inert diluents, e.g., lubricating agents as magnesium stearate, preservatives such as parabens and sorbic acid, antioxidants such as ascorbic acid, α-tocopherol and cysteine, disintegrants, binders, thickening, buffering, sweetening, flavoring, and perfuming agents. Tablets and pills can additionally be prepared with enteric coatings. Liquid dosage forms for oral administration may include pharmaceutically acceptable emulsions, syrups, elixirs, suspensions, solutions containing inert diluents commonly used in the art, such as water.

Specific dose levels for any particular patient will be employed depending upon a variety of factors including the activity of specific compounds employed, the age, body weight, general health, sex, diet, time of administration, route of administration, rate of excretion, drug combination, and the severity of the particular disease undergoing therapy. The dose varies with the diseases to be treated, symptoms, subjects and administration routes, and it is desirable that a daily dose of 1 to 50 mg for oral administration or 1 to 30 mg for intravenous injection can be administered in single or divided into 2 to 3 administrations when used as an agent for the therapy in adults. For example, when used for treating adult essential hypertension, the active ingredient will preferably be administered in an appropriate amount, for example, about 1 mg to 50 mg a day orally and about 1 mg to 30 mg a day intravenously. The active ingredient will preferably be administered in equal doses two or three times a day.

The foregoing is merely illustrative of the invention and is not intended to limit the invention to the disclosed compounds.

EXAMPLES

By the following formulation examples, working examples, experimental examples and reference examples, the present invention will be explained more concretely, but they should not be interpreted as limiting the invention in any manner.

Examples of abbreviations in this specification are as follows:

Me: methyl, Et: ethyl, Tet: tetrazolyl, Pr: propyl, Bu: butyl, tBu: tert-butyl, Ph: phenyl, DMF: dimethylformamide, and THF: tetrahydrofuran.

WORKING EXAMPLE 1

2-Butyl-7-methyl-3-[[2'-(1H-tetrazol-5-yl)biphenyl-4-yl]methyl]-3H-imidazo[4,5-c]pyridine-4-carboxylic acid 1a) 3-Methyl-4,5-diaminopyridine 3-Methyl-4,5-diaminopyridine was prepared according to the methods by B. Brekiesz-Lewandowska et al. [Rocz. Chem., 41, 1887 (1967); C.A. 69, 2911w (1968)].

1b) 2-Butyl-7-methylimidazo[4,5-c]pyridine

The compound obtained in Example 1a) (0.87 g) and valeric acid (1.1 ml) were mixed with polyphosphoric acid (16 g) and the mixture was heated at 140° C. for 4 hours. The reaction mixture was dissolved in water and the resulting solution was made basic with aqueous ammonia. The resulting insoluble materials were extracted with chloroform and the extract was washed with water, dried and evaporated. The residue was purified by column chromatography on silica gel to give crude crystals. Recrystallization from ethyl acetate-isopropyl ether afforded pale brown crystals (1.26 g, 94%), m.p. 111°–124° C. $^1$H-NMR(200 MHz, CDCl$_3$) δ: 0.90(3H,t), 1.31–1.50(2H,m), 1.79–1.92(2H,m), 2.53(3H,s), 2.99(2H,t), 8.19(1H,s), 8.77(1H,s)

1c) 2-Butyl-7-methylimidazo[4,5-c]pyridine-5-oxide

A solution of the compound obtained in Example 1b) (1.25 g) in a mixture of acetic acid (0.61 g) and aqueous hydrogen peroxide (30%, 1.28 ml) was heated at 115° C. for 14 hours. The reaction mixture was concentrated to dryness and the resulting residue was purified by column chromatography on silica gel to give a yellow syrup (0.8 g, 59%).

$^1$H-NMR(200 MHz, CDCl$_3$) δ: 0.89(3H,t), 1.30–1.49(2H,m), 1.72–1.89(2H,m), 2.52(3H,s), 2.93(2H,t), 7.92(1H,s), 8.43(1H,s)

1d) 2-Butyl-4-cyano-7-methylimidazo[4,5-c]pyridine

To a solution of the compound obtained in Example 1c) (0.8 g) in a mixture of chloroform (4 ml) and acetonitrile (10 ml) were added trimethylsilyl cyanide (1.63 g) and trimethylamine (0.79 g) and the mixture was heated under reflux for 2 hours. The reaction mixture was concentrated to dryness. To the resulting residue was added ethyl acetate to give brown powders (0.7 g, 84%), m.p. 197°–198° C.

$^1$H-NMR(200 MHz, CDCl$_3$) δ: 0.93(3H,t), 1.30–1.48(2H,m), 1.73–1.89(2H,m), 2.55(3H,s), 2.93(2H,t), 8.25(1H,s), 8.77(1H,s)

1e) Methyl 2-butyl-7-methylimidazo[4,5-c]pyridine-4-carboxylate

A solution of the compound obtained in Example 1d) in 20% hydrochloride-methanol (20 ml) was heated under reflux for 1 hour. The reaction mixture was concentrated to dryness. The resulting residue was dissolved in methylene chloride-water. The aqueous layer was neutralized with aqueous ammonia, followed by extraction with methylene chloride. The extract was washed, dried and concentrated to dryness. The resulting residue was purified by column chromatography on silica gel to give crude crystals. Recrystallization from isopropyl ether-hexane afforded colorless prisms (0.54 g, 67%), m.p. 126°–127° C.

$^1$H-NMR(200 MHz, CDCl$_3$) δ: 0.97(3H,t), 1.39–1.56(2H,m), 1.80–1.95(2H,m), 2.70(3H,s), 3.02(2H,t), 4.07(3H,s), 8.36(1H,s)

1f) Methyl 2-butyl-7-methyl-3-[[2'-(N-trityltetrazol-5-yl)biphenyl-4-yl]methyl]-3H-imidazo[4,5-c]pyridine-4-carboxylate (1f)

To a stirred solution of the compound obtained in Example 1e) in DMF (15 ml) was added sodium hydride (60% dispersion in mineral oil, 0.11 g) under ice-cooling and the reaction mixture was stirred for 30 minutes. To the reaction mixture was added N-triphenylmethyl-5-[2'-(4-bromomethyl)biphenyl]tetrazole (2.0 g), followed by stirring at room temperature for 16 hours. The reaction mixture was concentrated to dryness and the residue was extracted with ethyl acetate-water. The organic layer was washed with water, dried and concentrated to dryness. The concentrate was purified by column chromatography on silica gel to yield methyl 2-butyl-7-methyl-3-[[2'-(N-trityltetrazol-5-yl)biphenyl-4-yl]methyl]-3H-imidazo[4,5-c]pyridine-4-carboxylate as pale yellow powders (0.38 g, 24%).

$^1$H-NMR(300 MHz,CDCl$_3$) δ: 0.92(3H,t), 1.31–1.49(2H,m), 1.73–1.89(2H,m), 2.71(3H,s), 2.86(2H,t), 3.71(3H,s), 5.70(2H,s), 6.62(2H,d), 6.86–7.00(6H,m), 7.02(2H,d), 7.09–7.51(12H,m), 7.89–7.91(1H,m), 8.31(1H,s)

1g) Methyl 2-butyl-7-methyl-3-[[2'-(1H-tetrazol-5-yl)biphenyl-4-yl]methyl]-3H-imidazo[4,5-c]pyridine-4-carboxylate (1f)

To a solution of the compound obtained in Example 1f) in methanol (15 ml) was added 1N aqueous solution of hydrochloric acid (0.65 ml) and the reaction mixture was stirred at room temperature for 1 hour. The reaction mixture was concentrated to dryness and the residue was extracted with ethyl acetate-water. The organic layer was washed with water, dried and concentrated to dryness. The concentrate was purified by column chromatography on silica gel to yield white powders (0.2 g, 79%), m.p. 149°–151° C.

| Elemental Analysis for C<sub>27</sub>H<sub>27</sub>N<sub>7</sub>O<sub>2</sub>: | | | |
|---|---|---|---|
| | C (%) | H (%) | N (%) |
| Calcd.: | 67.34; | 5.65; | 20.36 |
| Found: | 67.51; | 5.38; | 20.43 |

$^1$H-NMR(200 MHz,CDCl$_3$) δ: 0.89(3H,t), 1.30–1.47(2H,m), 1.62–1.79(2H,m), 2.32(3H,s), 2.67(2H,t), 3.65(3H,s), 5.77(2H,s), 6.71(2H,d), 6.79(2H,d), 7.20–7.30(1H,m), 7.48–7.59(2H,m), 7.68(1H,s), 7.80–7.89(1H,m)

1h) 2-Butyl-7-methyl-3-[[2'-(1H-tetrazol-5-yl)biphenyl-4-yl]methyl]-3H-imidazo[4,5-c]pyridine-4-carboxylic acid To a solution of the compound obtained in Example 1g) in methanol (15 ml) was added 1N aqueous solution of sodium hydroxide (0.75 ml) and the reaction mixture was heated under a reflux for 6 hours. The reaction mixture was concentrated to dryness and the residue was dissolved in water. The insoluble was removed and the filtrate was acidified with 1N aqueous solution of hydrochloric acid to precipitate crystals as colorless powders (0.1 g, 64%), m.p. 159°–161° C.

| Elemental Analysis for C<sub>26</sub>H<sub>25</sub>N<sub>7</sub>O<sub>2</sub>: | | | |
|---|---|---|---|
| | C (%) | H (%) | N (%) |
| Calcd.: | 65.53; | 5.50; | 20.57 |
| Found: | 65.25; | 5.52; | 20.60 |

$^1$H-NMR(200 MHz, DMSO-d$_6$) δ: 0.85(3H,t), 1.25–1.42(2H,m), 1.60–1.75(2H,m), 2.60(3H,s), 2.87(2H,t), 6.23(2H,s), 6.91(2H,d), 7.02(2H,d), 7.47–7.70(4H,m), 8.23(1H,s)

Working Example 2

2-Propyl-7-methyl-3-[[2'-(1H-tetrazol-5-yl)biphenyl-4-yl]methyl]-3H-imidazo[4,5-c]pyridine-4-carboxylic acid 2a) The title compound was synthesized in the substantially same manner as in Example 1 (1a–1h). The processes are illustrated below.

2b) 7-Methyl-2-propylimidazo[4,5-c]pyridine

The title compound was synthesized as brown prisms (0.42 g, 26%) from the compound obtained in Example 1a) (1.15 g), in the substantially same manner as in Example 1b). m.p. 173°–175° C.

$^1$H-NMR(200 MHz, CDCl$_3$) δ: 0.97(3H,t), 1.81–2.00(2H,m), 2.51(3H,t), 2.97(2H,t), 8.16(1H,s), 8.76(1H,s)

2c) 7-Methyl-2-propylimidazo[4,5-c]pyridine-5-oxide

The title compound was synthesized as yellow powders (0.33 g, 55%) from the compound obtained in Example 2b) (0.55 g), in the substantially same manner as in Example 1c).

$^1$H-NMR(200 MHz, CDCl$_3$) δ: 0.96(3H,t), 1.76–1.94(2H,m), 2.49(3H,s), 2.89(2H,t), 7.91(1H,s), 8.49(1H,s)

2d) 4-Cyano-7-methyl-2-propylimidazo[4,5-c]pyridine

The title compound was synthesized as white powders (0.33 g, 95%) from the compound obtained in Example 2c) (0.33 g), in the substantially same manner as in Example 1d). m.p. 239°–242° C.

$^1$H-NMR(200 MHz, DMSO-d$_6$) δ: 0.97(3H,t), 1.75–1.93(2H,m), 2.55(3H,s), 2.90(2H,t), 8.24(1H,s)

2e) Methyl 7-methyl-2-propylimidazo[4,5-c]pyridine-4-carboxylate

The title compound was synthesized as a brown syrup (0.27 g, 70%) from the compound obtained in Example 2d) (0.33 g), in the substantially same manner as in Example 1e).

$^1$H-NMR(200 MHz, CDCl$_3$) δ: 1.06(3H,t), 1.86–2.03(2H,m), 2.70(3H,t), 3.00(2H,t), 4.06(3H,t), 8.35(1H,s)

2f) Methyl 7-methyl-2-propyl-3-[[2'-(N-trityltetrazol-5-yl)biphenyl-4-yl]methyl]-3H-imidazo[4,5-c]pyridine-4-carboxylate The title compound was synthesized as pale brown powders (0.13 g, 16%) from the compound obtained in Example 2e) (0.27 g), in the substantially same manner as in Example 1f).

$^1$H-NMR(200 MHz, CDCl$_3$) δ: 0.99(3H,t), 1.76–1.94(2H,m), 2.71(3H,s), 2.83(2H,t), 3.71(3H,s), 5.69(2H,s) 6.61(2H,d), 6.86–7.04(8H,m), 7.10–7.51(12H,m), 7.86–7.91(1H,m), 8.30(1H,s)

2g) Methyl 7-methyl-2-propyl-3-[[2'-(1H-tetrazol-5-yl)biphenyl-4-yl]methyl]-3H-imidazo[4,5-c]pyridine-4-carboxylate The title compound was synthesized as pale yellow powders (0.07 g, 82%) from the compound obtained in Example 2f) (0.13 g), in the substantially same manner as in Example 1g). m.p. 239°–242° C.

$^1$H-NMR(200 MHz, CDCl$_3$) δ: 1.00(3H,t), 1.70–1.91(2H,m), 2.40(3H,s), 2.74(2H,t), 3.64(3H,s), 5.70(2H,s) 6.61(2H,d), 6.78(2H,d), 7.20–7.30(1H,m), 7.38–7.54(2H,m), 7.65–7.75(1H,m), 7.85(1H,s)

2h) 7-Methyl-2-propyl-3-[[2'-(1H-tetrazol-5-yl)biphenyl-4-yl]methyl]-3H-imidazo[4,5-c]pyridine-4-carboxylic acid The title compound was synthesized as colorless powders (0.037 g, 73%) from the compound obtained in Example 2g) (0.05 g), in the substantially same manner as in Example 1h). m.p. 161°–163° C.

| Elemental Analysis for C<sub>25</sub>H<sub>23</sub>N<sub>7</sub>O<sub>2</sub>.H<sub>2</sub>O: | | | |
|---|---|---|---|
| | C (%) | H (%) | N (%) |
| Calcd.: | 63.68; | 5.34; | 20.79 |
| Found: | 63.76; | 5.29; | 21.03 |

$^1$H-NMR(200 MHz, DMSO-d$_6$) δ: 0.93(3H,t), 1.64–1.82(2H,m), 2.60(3H,s), 2.84(2H,t), 6.22(2H,s), 6.90(2H,d) 7.01(2H,d), 7.47–7.70(4H,m), 8.22(1H,s)

Working Example 3

2-Ethyl-4-oxo-9-[[2'-(1H-tetrazol-5-yl)biphenyl-4-yl]methyl]-4,9-dihydrothieno[2,3-b]quinoline-8-carboxylic acid 3a) Isopropyl 3-(cyanomethylcarbonyl)-2-fluorobenzoate The title compound was prepared according to the methods by D. N. Ridge et al. [J. Med. Chem., 22, (1979)].

3b) Methyl 3-(cyanomethylcarbonyl)-2-fluorobenzoate

A solution of the compound obtained in Example 3a) (0.45 g) and NaOMe (0.45 g) in methanol (40 ml) was reacted at 60°–70° C. for 3 hours. To the reaction mixture was added ethyl acetate and the mixture was washed with dilute hydrochloric acid and then water, dried and concentrated to dryness. The residue was purified by column chromatography on silica gel to afford white powders (0.28 g, 70%).

$^1$H-NMR(200 MHz, CDCl$_3$) δ: 3.98(3H,s), 4.14(2H,d), 7.14(1H,t), 8.1–8.3(2H,m)

3c) Methyl 3-[(2-amino-5-ethylthiophen-3-yl)carbonyl]-2-fluorobenzoate

The title compound was prepared according to the methods by M. Nakanishi et al. [J. Med. Chem., 16, 214 (1979)].

To a mixture of the compound obtained in Example 3b) (0.77 g), sulfur (0.11 g) and triethylamine (0.49 ml) in DMF (5 ml) was added butyraldehyde (0.31 ml) and the reaction mixture was reacted at room temperature for 20 minutes and then at 50° C. for 1 hour. To the mixture was added ethyl acetate and the resulting mixture was washed successively with dilute hydrochloric acid, aqueous sodium bicarbonate and water, dried and concentrated to dryness. The resulting residue was purified by column chromatography on silica gel to give pale yellow syrup (0.8 g, 74%).

$^1$H-NMR(200 MHz, CDCl$_3$) δ: 1.16(2H,q), 3.95(3H,s), 6.18(1H,s), 7.18(2H,br s), 7.28(1H,dd), 7.5–7.7(1H,m), 7.9–8.1(1H,m)

3d) Methyl 2-ethyl-4-oxo-9-[(2'-cyanobiphenyl-4-yl)methyl]-4,9-dihydrothieno[2,3-b]quinoline-8-carboxylic acid To a solution of the compound obtained in Example 3c) (0.8 g) and (2'-cyanobiphenyl-4-yl)methyl bromide (0.71 g) in DMF (15 ml) was added sodium hydride (60% dispersion in mineral oil, 0.24 g) and the reaction mixture was stirred at room temperature for 40 minutes. To the reaction mixture was added ethyl acetate and the mixture was washed with dilute hydrochloric acid and water, dried and concentrated to dryness. The resulting brown syrup was purified by column chromatography on silica gel to give pale yellow powders (0.28 g, 22%), m.p. 203°–205° C.

$^1$H-NMR(200 MHz, CDCl$_3$) δ: 1.33(3H,t), 2.81(2H,q), 3.64(3H,s), 5.56(2H,s), 7.14(2H,d), 7.3–7.8(8H,m), 7.85(1H,dd), 8.79(1H,dd)

3e) Methyl 2-ethyl-4-oxo-9-[[2'-(1H-tetrazol-5-yl)biphenyl-4-yl]methyl]-4,9-dihydrothieno[2,3-b]quinoline-8-carboxylate A solution of the compound obtained in Example 3d) (0.29 g) and trimethyltin azide (0.55 g) in toluene (18 ml) was heated under reflux for 60 hours. The reaction mixture was concentrated to dryness followed by addition of methanol (20 ml) and 1N aqueous solution of hydrochloric acid (20 ml) to the residue. The mixture was stirred at room temperature for 2 hours and evaporated. The residue was dissolved in chloroform, washed with water, dried and concentrated. The resulting yellow syrup was purified by column chromatography on silica gel to yield yellow powders (0.12 g, 36%), m.p. 228°–231° C.

Elemental Analysis for C$_{29}$H$_{23}$N$_5$O$_3$S.0.5H$_2$O:

|  | C (%) | H (%) | N (%) |
|---|---|---|---|
| Calcd.: | 65.65; | 4.56; | 13.20 |
| Found: | 65.48; | 4.38; | 12.80 |

$^1$H-NMR(200 MHz, CDCl$_3$) δ: 1.33(3H,t), 2.83(2H,q), 3.73(3H,s), 5.48(2H,s), 6.96(2H,d), 7.08(2H,d), 7.28(1H,s), 7.3–7.7(4H,m), 7.78(1H,dd), 7.89(1H,dd), 8.75(1H,dd)

3f) 2-Ethyl-4-oxo-9-[[2'-(1H-tetrazol-5-yl)biphenyl-4-yl]methyl]-4,9-dihydrothieno[2,3-b]quinoline-8-carboxylic acid A solution of the compound obtained in Example 3e) in methanol (3 ml) and 1N aqueous solution of sodium hydroxide (3 ml) was stirred at 70° C. for 3 hours. The reaction mixture was neutralized with dilute hydrochloric acid and extracted with chloroform. The extract was washed with water, dried and concentrated to dryness. The resulting brown syrup was purified by column chromatography on silica gel to yield pale yellow crystalline powders (0.054 g, 55%), m.p. about 290° C. (decomp.).

Elemental Analysis for C$_{28}$H$_{21}$N$_5$O$_3$S:

|  | C (%) | H (%) | N (%) |
|---|---|---|---|
| Calcd.: | 66.26; | 4.17; | 13.80 |
| Found: | 65.83; | 4.50; | 13.62 |

$^1$H-NMR(200 MHz, DMSO-d$_6$) δ: 1.25(3H,t), 2.78(2H,q), 5.78(3H,s), 6.83(2H,d), 6.94(2H,d), 7.11(1H,s), 7.1–7.6(5H,m), 7.83(1H,dd), 8.30(1H,dd) IR(KBr) cm$^{-3}$: 16.10, 1580, 1515 SIMS: 508 (M+)

Working Example 4

Ethyl 3-ethoxycarbonyl-7-isopropyl-4,7-dihydro-5-propyl-4-[[2'-(1H-tetrazol-5-yl)biphenyl-4-yl]methyl]-pyrazolo[1,5-a]pyrimidine-6-carboxylate 4a) Ethyl 3-ethoxycarbonyl-7-isopropyl-5-propyl-4,7-dihydropyrazolo[1,5-a]pyrimidine-6-carboxylate The title compound can be prepared according to the methods as disclosed in Japanese Patent Application Laid Open Nos. 218306/1985, 270584/1987, 243209/1988, etc.

A solution of ethyl 2-butyryl-4-methyl-2-pentenoate (1.27 g) and 3-amino-3-carboethoxypyrazole (0.78 g) in DMF (15 ml) was heated at at 120° C. for 10 hours. The reaction mixture was concentrated to dryness. The resulting residue was purified by column chromatography on silica gel to yield a colorless syrup (0.63 g, 36%).

$^1$H-NMR(200 MHz, CDCl$_3$) δ: 0.63(3H,d), 1.04(3H,d), 1.05(3H,d), 1.31(3H,t), 1.37(3H,t), 1.70(2H,m), 1.96–2.13(1H,m), 2.65–2.99(2H,m), 4.20(2H,q), 4.30(2H,q), 5.36(1H,d), 7.57(1H,br s), 7.70(1H,s)

4b) Ethyl 3-ethoxycarbonyl-7-isopropyl-5-propyl-4-[[2'-(N-trityltetrazol-5-yl)biphenyl-4-yl]methyl]-4,7-dihydropyrazolo[1,5-a]pyrimidine-6-carboxylate To a solution of the compound obtained in Example 4a) (0.63 g) in DMF (15 ml) was added sodium hydride (60% dispersion in mineral oil, 94 mg) and the reaction mixture was stirred for 10 minutes. To the reaction mixture was added 2'-(N-trityltetrazol-5-yl)biphenyl-4-yl]methyl bromide (1.50 g) and the mixture was stirred at 70° C. for 3 hours. After addition of water, the mixture was extracted with ethyl acetate. The extract was washed with water, dried and evaporated. The resulting residue was purified by column chromatography on silica gel to give a colorless syrup (0.76 g, 52%).

$^1$H-NMR(200 MHz, CDCl$_3$) δ: 0.57(3H,d), 0.75(3H,d), 1.00(3H,t), 1.28(3H,t), 1.35(3H,t), 1.39–1.78(2H,m), 2.60–2.80(1H,m), 3.38–3.53(1H,m), 4.17(2H,q), 4.19(2H,q), 4.90(1H,d), 5.07(1H,d), 5.83(1H,d), 6.83–7.55(26H,m), 7.85(1H,s), 7.88–7.98(1H,m)

4c) Ethyl 3-ethoxycarbonyl-7-isopropyl-5-propyl-4-[[2'-(1H-tetrazol-5-yl)biphenyl-4-yl]methyl]-4,7-dihydropyrazolo[1,5-a]pyrimidine-6-carboxylate To a solution of the compound obtained in Example 4b) (0.70 g) in a mixture of methylene chloride (2 ml) and methanol (10 ml) was added 1N aqueous solution of hydrochloric acid (5 ml) and the reaction mixture was stirred at room temperature for 3 hours. After addition of water, the mixture was extracted with chloroform. The extract was washed with water, dried and concentrated to dryness. The resulting residue was purified by column chromatography on silica gel to give a syrup. Recrystallization from ethyl acetate afforded colorless prisms (0.26 g, 51%), m.p. 183°–184° C.

| Elemental Analysis for $C_{32}H_{37}N_7O_4.0.5H_2O$: | | | |
|---|---|---|---|
| | C (%) | H (%) | N (%) |
| Calcd.: | 64.85; | 6.46; | 16.54 |
| Found: | 64.65; | 6.00; | 16.48 |

$^1$H-NMR(200 MHz, CDCl$_3$) δ: 0.60(3H,d), 0.83(3H,d), 0.98(3H,t), 1.30(3H,t), 1.33(3H,t), 1.40–1.78(2H,m), 2.78–2.94(1H,m), 3.09–3.28(1H,m), 4.18(2H,q), 4.19(2H,q), 4.24(2H,q), 5.18(1H,d), 5.19(1H,d), 5.79(1H,d), 7.13(2H,d), 7.19(2H,d), 7.35–7.66(3H,m), 7.83(1H,s), 8.07(1H,m)

Working Example 5

2-Ethyl-5-propyl-4-[[2'-(1H-tetrazol-5-yl)biphenyl-4-yl]methyl]-4,7-dihydropyrazolo[1,5-a]pyrimidine-3-carboxylic acid 5a) Tert-butyl 3-ethoxycarbonyl-7-ethyl-5-propyl-4,7-dihydropyrazolo[1,5-a]pyrimidine-6-carboxylate In substantially the same manner as Working Example 4a), the title compound was obtained as colorless prisms (7.92 g, 45%), m.p. 87°–88° C.

$^1$H-NMR(200 MHz,CDCl$_3$) δ: 0.72(3H,t), 1.37(3H,t), 1.52(9H,s), 1.46–1.86(3H,m), 1.94–2.16(1H,m), 2.84(2H,q), 4.30(2H,q), 5.45(1H,t), 7.50(1H,br s), 7.72(1H,s)

5b) 3-Ethoxycarbonyl-7-ethyl-5-propyl-4,7-dihydropyrazolo[1,5-a]-pyrimidine-6-carboxylic acid To a mixture of trifluoroacetic acid (20 ml), methylene chloride (2 ml) and water (2 ml) was added the compound obtained in Working Example 5a) (5.3 g) and the mixture was stirred at 0° C. for 3 hours. The reaction mixture was extracted with chloroform and the extract was washed with water, dried and concentrated to dryness. The resulting residue was recrystallized from ether to afford colorless prisms (2.62 g, 59%), m.p. 160°–161° C.

$^1$H-NMR(200 MHz,CDCl$_3$) δ: 0.71(3H,t), 1.30(3H,t), 1.37(3H,t), 1.76–2.27(3H,m), 2.92(2H,q), 2.93(2H,q), 4.31(2H,q), 5.12(1H,t), 7.74(1H,s), 7.76(1H,br s)

5c) Ethyl 7-ethyl-5-propyl-4,7-dihydropyrazolo[1,5-a]-pyrimidine-3-carboxylate

A mixture of the compound obtained in Working Example 5b) (2.59 g) in ethylene glycol (15 ml) was heated at 185°–190° C. for 30 minutes. The reaction mixture was partitioned between ether and water. The organic layer was washed with 1N aqueous NaOH and water, dried and concentrated to dryness. The resulting residue was purified by column chromatography on silica gel to give a syrup (1.74 g, 78%).

$^1$H-NMR(200 MHz,CDCl$_3$) δ: 0.88–1.04(1H,m), 1.17(3H,t), 1.27–1.52(2H,m), 1.35(3H,t), 1.65–1.88(2H,m), 1.89–2.15(1H,m), 2.23(2H,q), 4.27(2H,q), 4.37–4.47(1H,m), 4.96–5.04(1H,m), 3.98(1H,br s), 7.68(1H,s)

5d) Ethyl 7-ethyl-5-propyl-4-[[2'-(N-trityltetrazol-5-yl)biphenyl-4-yl]methyl]-4,7-dihydropyrazolo[1,5-a]pyrimidine-3-carboxylate To a solution of the compound obtained in Working Example 5c) (1.7 g) in DMF (30 ml) was added sodium hydride (60% dispersion in mineral oil, 0.31 g) and the mixture was stirred at room temperature for 10 minutes. To the reaction mixture was added [(2'-N-trityltetrazol-5-yl)biphenyl-4-yl]methyl bromide (4.5 g) and the mixture was stirred at room temperature for 3 hours. After addition of water, the mixture was extracted with ether. The extract was washed with water, dried and concentrated to dryness. The residue was purified by column chromatography on silica gel to give a colorless syrup (1.54 g, 32%).

$^1$H-NMR(200 MHz,CDCl$_3$) δ: 0.74(3H,t), 0.88(3H,t), 1.34(3H,t), 1.56–1.84(2H,m), 2.14–2.29(2H,m), 4.22(2H,q), 4.74–4.85(1H,m), 4.89(1H,d), 5.43(1H,d), 6.17–7.56(22H,m), 7.87(1H,s), 7.83–7.96(1H,m) IR(neat) cm$^{-1}$: 1740, 1700, 1595

5e) Ethyl 7-ethyl-5-propyl-4-[[2'-(1H-tetrazol-5-yl)biphenyl-4-yl]methyl]-4,7-dihydropyrazolo[1,5-a]pyrimidine-3-carboxylate To a solution of the compound obtained in Working Example 5d) (1.5 g) in a mixture of acetone (10 ml) and methanol (10 ml) was added 1N HCl (10 ml) and the mixture was stirred at room temperature for 3 hours. After extraction with chloroform, the extract was washed with water, dried and concentrated to dryness. The residue was purified by column chromatography on silica gel to give white powders (0.5 g, 50%).

| Elemental Analysis for $C_{28}H_{31}N_7O_2.0.5H_2O$: | | | |
|---|---|---|---|
| | C (%) | H (%) | N (%) |
| Calcd.: | 66.38; | 6.37; | 19.35 |
| Found: | 66.07; | 6.05; | 19.86 |

$^1$H-NMR(200 MHz,CDCl$_3$) δ: 0.73(3H,t), 1.16(3H,t), 1.33(3H,t), 1.62–1.89(3H,m), 2.32(2H,q), 4.23(2H,q), 4.76–4.88(1H,m), 4.83(1H,s), 5.14& 5.49(2H,ABq), 7.08(2H,d), 7.15(2H,d), 7.27(1H,s), 7.32–7.66(3H,m), 7.79(1H,s), 8.03–8.11(1H,m), 7.60(1H,dd), 7.73–7.82(2H,m) IR(neat) cm$^{-1}$: 1700, 1600

5 5f) 7-Ethyl-5-propyl-4-[[2'-(1H-tetrazol-5-yl)biphenyl-4-yl]methyl]-4,7-dihydropyrazolo[1,5-a]pyrimidine-3-carboxylic acid In substantially the same manner as Working Example 1h), the compound obtained in Working Example 5e) was hydrolyzed with alkaline to afford the above compound.

Working Example 6

5-Propyl-4-[[2'-(1H-tetrazol-5-yl)biphenyl-4-yl]methyl]-imidazo[1,2-b]pyrazol-3-carboxylic acid 6a) Ethyl 3-amino-2-(2-oxopentyl)pyrazol-4-carboxylate To a mixture of sodium hydride (60% dispersion in mineral oil, 0.8 g) in DMF (50 ml) was added ethyl 3-amino-pyrazol-4-carboxylate (2.0 g) and the reaction mixture was stirred at room temperature for 15 minutes. After addition of 1-bromo-2-pentanone (4.0 g), the mixture was stirred at room temperature for 13 hours. The reaction mixture was concentrated to dryness, and the residue was dissolved in ethyl acetate-water. The organic layer was washed with water, dried and concentrated to dryness. The resulting yellow syrup was purified by column chromatography on silica gel to give pale yellow prisms (1.4 g, 45%).

$^1$H-NMR(200 MHz,CDCl$_3$) δ: 0.93(3H,t), 1.35(3H,t), 1.65(2H,m), 2.47(2H,t), 4.28(2H,q), 4.73(2H,s), 5.05(2H,br s), 7.66(1H,s)

6b) Ethyl 5-propylimidazo[1,2-b]pyrazol-3-carboxylate

A mixture of the compound obtained in Working Example 6a) (1.0 g) and p-toluenesulfonic acid (0.75 g) in toluene (500 ml) was heated under reflux for 3 days. The reaction mixture was washed with aqueous sodium bicarbonate and water, and concentrated in vacuo to dryness. The resulting pale yellow powders were recrystallized from methanol-isopropyl ether to afford white crystalline powders (0.9 g, 92%), m.p. 160°–161° C.

| Elemental Analysis for C$_{11}$H$_{15}$N$_3$O$_2$: | | |
|---|---|---|
| C (%) | H (%) | N (%) |
| Calcd.: 59.71; | 6.83; | 18.99 |
| Found: 59.61; | 6.55; | 19.0 |

$^1$H-NMR(200 MHz,CDCl$_3$) δ: 0.97(3H,t), 1.35(3H,t), 1.67(2H,m), 2.61(2H,t), 4.32(2H,q), 7.19(1H,s), 7.99(1H,s), 9.82(1H,br s)

6c) Ethyl 5-propyl-4-[[2'-(N-trityltetrazol-5-yl)biphenyl-4-yl]methyl]-imidazo[1,2-b]pyrazol-3-carboxylate To a solution of ethyl 5-propylimidazo[1,2-b]pyrazol-3-carboxylate (0.5 g) in DMF (30 ml) was added sodium hydride (60% dispersion in mineral oil, 0.14 g) and the mixture was stirred at room temperature for 15 minutes. To the reaction mixture was added [(2'-N-trityltetrazol-5-yl)biphenyl-4-yl]methyl bromide (1.90 g) and the mixture was stirred at room temperature for 65 hours. After the reaction mixture was concentrated to dryness, the residue was dissolved in ethyl acetate. The organic layer was washed with water, dried and concentrated to dryness. The resulting brown powders were purified by column chromatography on silica gel to give white powders (1.0 g, 63%).

$^1$H-NMR(200 MHz,CDCl$_3$) δ: 0.87(3H,t), 1.23(3H,t), 1.52(2H,m), 2.31(2H,t), 4.15(2H,q), 5.65(2H,s), 6.8–7.5(23H,m), 7.86(1H,dd), 8.01(1H,s)

6d) Ethyl 5-propyl-4-[[2'-(1H-tetrazol-5-yl)biphenyl-4-yl]methyl]-imidazo[1,2-b]pyrazol-3-carboxylate To a solution of the compound obtained in Working Example 6c) (0.9 g) in methanol (10 ml) and THF (15 ml) was added 1N aqueous HCl (5 ml) and the mixture was stirred at room temperature for 5 hours. After evaporation of the solvent, the residue was extracted with methylene chloride. The extract was washed with water, dried and concentrated to dryness. The residue was purified by column chromatography on silica gel to give crystals which were recrystallized from methanol to afford colorless prisms (0.41 g, 70%), m.p. 208°–209° C.

| Elemental Analysis for C$_{25}$H$_{25}$N$_7$O$_2$: | | |
|---|---|---|
| C (%) | H (%) | N (%) |
| Calcd.: 65.92; | 5.53; | 21.52 |
| Found: 65.86; | 5.61; | 21.42 |

6e) 5-Propyl-4-[[2'-(1H-tetrazol-5-yl)biphenyl-4-yl]methyl]imidazo[1,2-b]pyrazol-3-carboxylic acid To a solution of the compound obtained in Working Example 6d) (0.26 g) in THF (30 ml) was added 1.2N aqueous lithium hydroxide (13 ml) and the mixture was heated under reflux for 8 hours. The reaction mixture was neutralized with 2N hydrochloric acid to precipitate pale yellow crystalline powders which were recrystallized from methanol to afford colorless prisms (0.15 g), m.p. 198°–199° C.

| Elemental Analysis for C$_{23}$H$_{21}$N$_7$O$_2$: | | |
|---|---|---|
| C (%) | H (%) | N (%) |
| Calcd.: 64.63; | 4.95; | 22.94 |
| Found: 64.25; | 4.88; | 22.68 |

$^1$H-NMR(200MHz,CDCl$_3$) δ: 0.89(3H,t,J=7.4 Hz), 1.50(2H,m), 2.44(2H,t,J=7.4 Hz), 5.74(2H,s), 7.50(4H,s), 7.50–7.70(5H,m), 7.86(1H,s), 11.87(1H,br s)

Working Example 7

2-Butyl-1-[[4-[2'-(1H-tetrazol-5-yl)-1-pyrrolyl]phenyl]methyl]benzimidazole-7-carboxylic acid 7a) 1-(4-Methylphenyl)pyrrole The title compound was obtained as yellow crystals (10.5 g, 66%, m.p. 82°–83° C.) from 4-methylaniline (10.7 g) and 2,5-dimethoxytetrahydrofuran (13.2 g) according to the known methods (R. Jones, C. F. Candy and P. H. Wright, J. Chem. Soc., 1970, 2563).

7b) 1-(4-Methylphenyl)pyrrole-2-(and -3-)carboaldehyde

The title 2-carbaldehyde compound (9.9 g, 80%) and 3-carboaldehyde compound (1.3 g, 10%) were obtained as pale yellow syrup from 1-(4-methylphenyl)pyrrole (10.5 g) according to the known methods (M. Artico, R. Giuliano, G. C. Porretta and M. Scalzo, Farmaco, Ed. Sci., 27, 60 (1972)).

7c) 1-(4-Methylphenyl)pyrrole-2-carbonitrile

The title 2-carbonitrile compound was obtained a a colorless prism (4.9 g, quantitatively) from 1-(4-methylphenyl)-pyrrole-2-carbaldehyde according to the known methods (M. Artico, R. Giuliano, G. C. Porretta and M. Scalzo, Farmaco, Ed. Sci., 27, 60 (1972)).

7d) 1-(4-Bromomethylphenyl)pyrrole-2-carbonitrile

A solution of 1-(4-methylphenyl)pyrrole-2-carbonitrile (4.9 g), N-bromosuccinimide (5.5 g) and perbenzoic acid (65 mg) in carbon tetrachloride was heated under reflux in light radiation for 2 hours. After removal of insoluble materials by filtration, the filtrate was concentrated to dryness. The residue was purified by column chromatography on silica gel to afford a colorless syrup (6.6 g, 93%).

$^1$H-NMR(200 MHz,CDCl$_3$) δ: 4.53(2H,s), 6.37(1H,dd), 7.01(1H,dd), 7.09(1H,dd), 7.44(2H,d), 7.54(2H,d) IR(neat) cm$^{-1}$: 2210, 1600, 1515, 1445, 1410, 1350, 1320, 1220, 1170, 1090, 1030, 840, 730

7e) Methyl 2-[N-[4-(2-cyano-1-pyrrolyl)phenyl]methyl-N-valeryl]amino-3-nitrobenzoate A solution of methyl 3-nitro-2-valerylaminobenzoate (2.2 g), 1-(4-bromomethylphenyl)pyrrole-2-carbonitrile (2.6 g) and K$_2$CO$_3$ (1.7 g) in acetonitrile (30 ml) was heated under reflux for 23 hours. After addition of water, the reaction mixture was extracted with ethyl acetate. The extract was washed with water, dried and concentrated to dryness. The residue was purified by column chromatography on silica gel to give a colorless syrup (3.6 g, 97%). $^1$H-NMR(200 MHz,CDCl$_3$) δ: 0.85(3H,t), 1.17–1.36(2H,m), 1.59–1.75(2H,m), 2.05–2.15(2H,m), 3.70(3H,s), 4.71(1H,d), 4.87(1H,d), 6.34(1H,dd), 6.99(1H,dd), 7.06(1H,dd), 7.21–7.33(4H,m), 7.62(1H,t), 7.97(1H,dd), 8.11(1H,d)IR(neat) cm$^{-1}$: 2210, 1740, 1680, 1600, 1535, 1520, 1460, 1430, 1425, 1090, 850, 825, 750, 700

7f) Methyl 2-butyl-1-[[4-(2-cyano-1-pyrrolyl)phenyl]-methyl]benzimidazole-7-carboxylate A solution of methyl 2-[N-[4-(2-cyano-1-pyrrolyl)-phenyl]methyl-N-valeryl]amino-3-nitrobenzoate (3.6 g), iron powders (1.4 g) and conc. hydrochloric acid (4.2 ml) in methanol (40 ml) was heated under reflux for 2.5 hours. After removal of insoluble materials by filtration, the filtrate was concentrated. After addition of water, the mixture was extracted with ethyl acetate. The extract was washed with water, dried and concentrated to dryness. The residue was purified by column chromatography on silica gel to give crystals which were recrystallized from ethyl acetate-hexane to afford pale purple prisms (2.2 g, 69%), m.p. 128°–129° C.

$^1$H-NMR(200 MHz,CDCl$_3$) δ: 0.96(3H,t), 1.39–1.56(2H,m), 1.81–1.96(2H,m), 2.90(2H,t), 3.73(3H,s), 5.83(2H,s), 6.33(1H,dd), 6.96–7.03(2H,m), 7.23–7.37(5H,m), 7.67(1H,d), 7.96(1H,d) IR(KBr) cm$^{-1}$: 2200, 1720, 1520, 1445, 1420, 1400, 1355, 1320, 1280, 1260, 1195, 1115, 750

7g) Methyl 2-butyl-1-[[4-[2-(1H-tetrazol-5-yl)-1-pyrrolyl]phenyl]methyl]benzimidazole-7-carboxylate A solution of methyl 2-butyl-1-[[4-(2-cyano-1-pyrrolyl)phenyl]methyl]benzimidazole-7-carboxylate (2.2 g) and trimethyltin azide (3.3 g) in toluene (35 ml) was heated under reflux for 3 days. After concentration, the residue was dissolved in methanol (40 ml) and 1N hydrochloric acid (20 ml) and the mixture was stirred at room temperature for 15 minutes. The reaction mixture was concentrated to dryness and the residue was extracted with ethyl acetate. The extract was washed with water, dried and evaporated. The residue was purified by column chromatography on silica gel to give crystals which were recrystallized from ethyl acetate to afford colorless crystals (1.8 g, 75%), m.p. 186°–187° C.

| Elemental Analysis for C$_{25}$H$_{25}$N$_7$O$_2$.0.2H$_2$O: | | | |
|---|---|---|---|
| | C (%) | H (%) | N (%) |
| Calcd.: | 65.40; | 5.53; | 21.36 |
| Found: | 65.30; | 5.41; | 21.41 |

$^1$H-NMR(200 MHz,CDCl$_3$) δ: 0.89(3H,t), 1.29–1.47(2H,m), 1.62–1.77(2H,m), 2.64(2H,t), 3.68(3H,s), 5.61(2H,s), 6.48(1H,t), 6.68(2H,d), 6.92–6.97(3H,m), 7.08(1H,dd), 7.20(1H,t), 7.47(1H,dd),7.59(1H,dd) IR(KBr) cm$^{-1}$: 1715, 1600, 1510, 1450, 1430, 1410, 1375, 1310, 1280, 1260, 1200, 1190, 1120, 1020, 940, 810, 750, 730

7h) 2-Butyl-1-[[4-[2-(1H-tetrazol-5-yl)-1-pyrrolyl]-phenyl]methyl]benzimidazole-7-carboxylic acid A solution of methyl 2-butyl-1-[[4-[2-(1H-tetrazol-5-yl)-1-pyrrolyl]phenyl]methyl]benzimidazole-7-carboxylate (0.85 g) in methanol (10 ml) containing 1N aqueous NaOH (5.7 ml) was heated under reflux for 2 hours. After evaporation of methanol, the residue was neutralized with 1N aqueous hydrochloric acid to precipitate crystals. Recrystallization from chloroform-methanol afforded colorless prisms (0.71 g, 78%), m.p. 165°–167° C.

| Elemental Analysis for C$_{24}$H$_{23}$N$_7$O$_2$.CH$_3$OH.0.2H$_2$O: | | | |
|---|---|---|---|
| | C (%) | H (%) | N (%) |
| Calcd.: | 62.93; | 5.79; | 20.55 |
| Found: | 62.60; | 5.76; | 20.89 |

$^1$H-NMR(200 MHz,DMSO-d$_6$) δ: 0.89(3H,t), 1.29–1.48(2H,m), 1.68–1.83(2H,m), 2.87(2H,t), 5.91(2H,s), 6.40(1H,dd), 6.87–6.91(2H,m), 7.17–7.28(5H,m), 7.63(1H,dd), 7.85(1H,dd) IR(KBr) cm$^{-1}$: 1700, 1610, 1515, 1360, 1315, 730

Working Example 8

2-Butyl-1-[[[4-[3-(1H-tetrazol-5-yl)-1-pyrrolyl]phenyl]-methyl]benzimidazole-7-carboxylic acid 8a) 1-(4-Methylphenyl)pyrrole-3-carbonitrile In substantially the same manner as Working Example 7c), the above 3-carbonitrile compound was obtained as colorless crystals (1.3 g, quantitatively, m.p. 71°–72° C.) from 1-(4-methylphenyl)pyrrole-3-carboaldehyde obtained in Working Example 7b).

$^1$H-NMR(200 MHz,CDCl$_3$) δ: 2.04(3H,s), 6.58(1H,dd), 6.99(1H,dd), 7.26(4H,s), 7.47(1H,dd)

8b) 1-(4-Bromomethylphenyl)pyrrole-3-carbonitrile

In substantially the same manner as Working Example 7d), the above bromo compound was obtained as colorless crystals (1.0 g, 53%, m.p. 100°–101° C.) from 1-(4-methylphenyl)pyrrole-3-carbonitrile (1.3 g).

$^1$H-NMR(200 MHz,CDCl$_3$) δ: 4.52(2H,s), 6.61(1H,dd), 7.03(1H,dd), 7.23–7.38(2H,m), 7.53–7.48(3H,m) IR(KBr) cm$^{-1}$: 2220, 1600, 1520, 1350, 1205, 1040, 800, 690

8c) Methyl 2-[N-[4-(3-cyano-1-pyrrolyl)phenyl]methyl-N-vareloyl]amino-3-nitrobenzoate In substantially the same manner as Working Example 7e), the above compound was obtained as a yellow syrup (1.3 g, 76%) from methyl 3-nitro-2-vareloylaminobenzoate (1.1 g) and 1-(4-bromomethyl-phenyl)pyrrole-3-carbonitrile (1.0 g).

$^1$H-NMR(200 MHz,CDCl$_3$) δ: 0.85(3H,t), 1.17–1.34(2H,m), 1.60–1.76(2H,m), 2.06–2.18(2H,m), 3.72(3H,s), 4.63(1H,d), 4.91(1H,d), 6.58(1H,dd), 7.00(1H,dd), 7.21(4H,s), 7.48(1H,m), 7.62(1H,t), 7.94(1H,dd), 8.12(1H,dd) IR(neat) cm$^{-1}$: 2225, 1740, 1680, 1540, 1450, 1360, 1290, 1265, 1205, 1130, 810, 770, 760, 700

8d) Methyl 2-butyl-1-[[4-(3-cyano-1-pyrrolyl)phenyl]-methyl]benzimidazole-7-carboxylate In substantially the same manner as Working Example 7f), the above compound was obtained as yellow needles (0.27 g, 23%, m.p. 174°–175° C.) from methyl 2-[N-[4-(3-cyano-1-pyrrolyl)phenyl]methyl-N-vareloyl-]amino-3-nitrobenzoate (1.3 g).

$^1$H-NMR(200 MHz,CDCl$_3$) δ: 0.95(3H,t), 1.37–1.55(2H,m), 1.80–1.95(2H,m), 2.89(2H,t), 3.74(3H,s), 5.82(2H,s), 6.57(1H,dd), 6.94–6.98(2H,m), 7.23–7.32(4H,m), 7.45(1H,t), 7.70(1H,dd), 7.98(1H,dd) IR(KBr) cm$^{-1}$: 2220, 1720, 1520, 1280, 1250, 1190, 1110, 800, 740

8e) Methyl 2-butyl-1-[[4-[3-(1H-tetrazol-5-yl)-1-pyrrolyl]phenyl]methyl]benzimidazole-7-carboxylate In substantially the same manner as Working Example 7g), the above compound was obtained as colorless crystals (0.3 g, quantitatively, m.p. 229°–230° C. (decomp.)) from methyl 2-butyl-1-[[4-(3-cyano-1-pyrrolyl)-phenyl]methyl]benzimidazole-7-carboxylate (0.27 g).

| Elemental Analysis for C$_{25}$H$_{25}$N$_7$O$_2$: | | | |
|---|---|---|---|
| | C (%) | H (%) | N (%) |
| Calcd.: | 65.92; | 5.53; | 21.52 |
| Found: | 65.66; | 5.46; | 21.77 |

¹H-NMR(200 MHz,DMSO-d₆) δ: 0.90(3H,t), 1.31–1.49(2H,m), 1.70–1.85(2H,m), 2.92(2H,t), 3.69(3H,s), 5.72(2H,s), 6.79(1H,dd), 6.94(2H,d), 7.26(1H,t), 7.51–7.55(2H,m), 7.59(2H,d), 7.88(1H,dd), 7.99(1H,m) IR(KBr) cm⁻¹: 1705, 1615, 1600, 1520, 1445, 1420, 1400, 1310, 1280, 1255, 1215, 1190, 1110, 750, 740

8f) 2-Butyl-1-[[4-[3-(1H-tetrazol-5-yl)-1-pyrrolyl]-phenyl]methyl]benzimidazole-7-carboxylic acid In substantially the same manner as Working Example 7h), the above compound was obtained as colorless prisms (0.11 g, 55%, m.p. 278°–280° C. (decomp.)) from methyl 2-butyl-1-[[4-[3-(1H-tetrazol-5-yl)-1-pyrrolyl]-phenyl]methyl]benzimidazole-7-carboxylate (0.2 g).

| Elemental Analysis for $C_{24}H_{23}N_7O_2 \cdot 0.3H_2O$: | | |
|---|---|---|
| C (%) | H (%) | N (%) |
| Calcd.: 64.50; | 5.32; | 21.94 |
| Found: 64.35; | 5.19; | 21.87 |

¹H-NMR(200 MHz,DMSO-d₆) δ: 0.89(3H,t), 1.30–1.47(2H,m), 1.69–1.84(2H,m), 2.89(2H,t), 5.87(2H,s), 6.79(1H,m), 6.95(2H,d), 7.25(1H,t), 7.52(1H,m), 7.59(2H,d), 7.61(1H,dd), 7.86(1H,dd), 7.99(1H,m) IR(KBr) cm⁻¹: 1690, 1600, 1520, 1420, 1405, 1310, 1280, 1240, 740

Working Example 9

2-Butyl-1-[[4-[2-(1H-tetrazol-5-yl)benzo[b]furan-3-yl]phenyl]methyl]benzimidazole-7-carboxylic acid a) 2'-cyanomethoxy-4-methylbenzophenone To a stirred solution of 2'-hydroxy-4-methylbenzophenone (9 g), potassium iodide (8.46 g) and potassium carbonate (8.79 g) in DMF (200 ml) was added chloroacetonitrile (3.85 g) and the mixture was stirred at room temperature for 2 days. The reaction mixture was concentrated to dryness. After the addition of water, the mixture was neutralized with 1N hydrochloric acid and extracted with ethyl acetate. The extract was washed with water, dried and concentrated to dryness. The residue was purified by column chromatography on silica gel to give pale brown syrup (8.9 g, 84%).

¹H-NMR(200 MHz,CDCl₃) δ: 2.43(3H,s), 4.71(3H,s), 7.14(2H,q), 7.2–7.3(2H,m), 7.4–7.1(1H,dd), 7.54(1H,dt), 7.70(2H,q)

9b) 2-cyano-3-(4-tolyl)benzo[b]furan

To a solution of 2'-cyanomethoxy-4-methylbenzophenone (8.9 g) in methanol (750 ml) was added CH₃ONa (2.0 g) and molecular sieves (3A, 5 g) and the mixture was heated under reflux for 30 hours. After removal of insoluble materials by filtration, the filtrate was concentrated to dryness. The residue was dissolved in ethyl acetate, followed by removal of insoluble materials by filtration and concentration of the filtrate. The residue was purified by column chromatography on silica gel to afford pale yellow powders (3.34 g, 40%).

¹H-NMR(200 MHz,CDCl₃) δ: 2.46(3H,s), 7.35–7.45(1H,m), 7.38(2H,q), 7.55–7.70(2H,m), 7.66(2H,q), 7.84(1H,dd)

9c) 2-cyano-3-(4-bromomethyl)benzo[b]furan

A solution of 2-cyano-3-(4-tolyl)benzo[b]furan (3.3 g), N-bromosuccinimide (2.77 g) and benzoyl peroxide (catalytic amount) in carbon tetrachloride (120 ml) was heated under reflux in light radiation for 1 hour. After removal of insoluble materials by filtration, the filtrate was concentrated. The resulting brown syrup was used for the next step without further purification.

9d) Methyl 2-[N-[4-(2-cyanobenzo[b]furan-3-yl)benzyl]-N-valeryl]amino-3-nitrobenzoate A solution of methyl 3-nitro-2-valerylaminobenzoate (2.8 g), 2-cyano-3-(4-bromomethyl)benzo[b]furan (6.5 g) and K₂CO₃ (2.5 g) in acetonitrile (200 ml) was stirred at 70° C. for 40 hours. After addition of water, the reaction mixture was neutralized with 1N hydrochloric acid and extracted with ethyl acetate. The extract was washed with water, dried and concentrated to dryness. The residue was purified by column chromatography on silica gel to give a pale yellow syrup (3.4 g, 67%).

¹H-NMR(200 MHz,CDCl₃) δ: 0.86(3H,t), 1.28(2H,m), 1.68(2H,m), 2.13(2H,dt), 3.68(3H,s), 4.71(1H,q), 4.96(1H,q), 7.30(2H,q), 7.35–7.65(6H,m), 7.80(1H,dd), 7.98(1H,dd), 8.11(1H,dd)

9e) Methyl 2-butyl-1-[[4-(2-cyanobenzo[b]furan-3-yl)phenyl]methyl]benzimidazole-7-carboxylate A solution of methyl 2-[N-[4-(2-cyanobenzo[b]furan-3-yl)benzyl]-N-vareloyl]amino-3-nitrobenzoate (3.4 g), iron powders (1.2 g) and conc. hydrochloric acid (2.2 ml) in methanol (18 ml) was heated under reflux for 30 minutes. After addition of ethyl acetate (150 ml) and removal of insoluble materials by filtration, the filtrate was washed with water, dried and concentrated to dryness. The residue was purified by column chromatography on silica gel to give crystals, which were recrystallized from methanol to afford colorless crystals (1.76 g, 57%).

¹H-NMR(200 MHz,CDCl₃) δ: 0.96(3H,t), 1.49(2H,m), 1.91(2H,m), 2.98(2H,t), 3.75(3H,s), 5.89(2H,s), 7.06(2H,q), 7.30–7.80(8H,m), 8.02(1H,dd)

9f) Methyl 2-butyl-1-[[4-[2-(1H-tetrazol-5-yl)benzo[b]furan-3-yl]phenyl]methyl]benzimidazole-7-carboxylate A solution of methyl 2-butyl-1-[[4-(2-cyanobenzo[b]furan-3-yl)phenyl]methyl]benzimidazole-7-carboxylate (1.3 g) and trimethyltin azide (2.9 g) in toluene (125 ml) was heated under reflux for 2 days. After concentration to dryness, the residue was dissolved in a mixture of methanol (150 ml) and 1N hydrochloric acid (25 ml) and the mixture was stirred at room temperature for 3 hours. The reaction mixture was concentrated to dryness and the residue was dissolved in methylene chloride. The resulting solution was washed with water, dried and concentrated to dryness. The residue was purified by column chromatography on silica gel to give pale yellow powders (1.3 g).

| Elemental Analysis for $C_{29}H_{26}N_6O_3 \cdot CH_3OH \cdot 1.5H_2O$: | | |
|---|---|---|
| C (%) | H (%) | N (%) |
| Calcd.: 63.71; | 5.88; | 14.86 |
| Found: 63.42; | 5.20; | 14.60 |

¹H-NMR(200 MHz,CDCl₃) δ: 0.84(3H,t), 1.40(2H,m), 1.85(2H,m), 3.10(2H,t), 3.79(3H,s), 5.86(2H,s), 6.96(2H,q), 7.20–7.65(5H,m), 7.58(2H,q), 7.71(1H,dd), 8.06(1H,dd)

9g) 2-Butyl-1-[[4-[2-(1H-tetrazol-5-yl)benzo[b]furan-3-yl]phenyl]methyl]benzimidazole-7-carboxylic acid A solution of methyl 2-butyl-1-[[4-[2-(1H-tetrazol-5-yl)benzo[b]furan-3-yl]phenyl]methyl]benzimidazole-7-carboxylate (1.1 g) 1N aqueous NaOH (12 ml) in methanol (50 ml) was stirred at room temperature for 24 hours. After evaporation of methanol, the residue was neutralized with 1N aqueous hydrochloric acid to precipitate crystals. Recrystallization from DMF-methanol afforded colorless crystals (0.82 g, 77%), m.p. 194°–195° C.

| Elemental Analysis for C$_{28}$H$_{24}$N$_6$O$_3$·½H$_2$O: | | | |
|---|---|---|---|
| | C (%) | H (%) | N (%) |
| Calcd.: | 67.66; | 4.97; | 17.04 |
| Found: | 67.62; | 4.95; | 17.00 |

$^1$H-NMR(200 MHz,DMSO-d$_6$) δ: 0.89(3H,t), 1.40(2H,sext), 1.78(1H,quint), 2.94(2H,t), 5.97(2H,s), 7.02(2H,q), 7.28(1H,t), 7.39(1H,t), 7.53(1H,dt), 7.64(2H,q), 7.6–7.7(2H,m), 7.78(1H,d), 7.87(1H,dd)

Working Example 10

2-Methyl-1-[[2'-(1H-tetrazol-5-yl)biphenyl-4-yl]methyl]indole-7-carboxylic acid

10a) Methyl 2-nitro-3-(2-oxo-n-propyl)benzoate

A solution of methyl 3-methyl-2-nitrobenzoate (1.5 g) and N,N-dimethylacetamide dimethyl acetal (3 ml) in dimethylacetamide (5 ml) was heated at 140° C. for 3 hours. After evaporation of the solvent, the resulting brown syrup was dissolved in ethyl acetate. The solution was washed with water, dried and concentrated to dryness. The residue was purified by column chromatography on silica gel to give a pale brown syrup (0.42 g, 23%).

$^1$H-NMR(200 MHz,CDCl$_3$) δ: 2.26(3H,s), 3.78(2H,s), 3.90(3H,s), 7.4–7.7(2H,m), 7.91(1H,dd)

10b) Methyl 2-methyl-1-[[2'-(N-trityltetrazol-5-yl)biphenyl-4-yl]methyl]indole-7-carboxylate A mixed solution of methyl 2-nitro-3-(2-oxo-n-propyl)benzoate (0.33 g) and 10% Pd/C (50% wet, 0.33 g) in THF (20 ml) was stirred under H$_2$ atmosphere at room temperature for 2.5 hours. After removal of insoluble materials by filtration, the filtrate was concentrated to dryness. The residue was purified by column chromatography on silica gel to give methyl 2-methylindole-7-carboxylate as a pale yellow syrup (0.225 g).

To a mixture of the resulting syrup and N-triphenylmethyl-5-[2-(bromomethylbiphenyl)tetrazole (0.33 g) in hexamethylphosphoric triamide (10 ml) was added sodium hydride (60% dispersion in mineral oil, 0.06 g) under nitrogen atmosphere and the mixture was stirred at room temperature for 1.5 hours. The reaction mixture was poured into dilute hydrochloric acid and extracted with ethyl acetate. The extract was washed with water, dried and concentrated to dryness. The residue was purified by column chromatography on silica gel to give pale yellow syrup. Recrystallization from ether-hexane afforded colorless crystals (0.48 g, 51%), m.p. 170°–173° C.

$^1$H-NMR(200 MHz,CDCl$_3$) δ: 2.27(3H,s), 3.53(3H,s), 5.48(2H,s), 6.43(1H,s), 6.57(2H,d), 6.8–7.6(22H,m), 7.71(1H,d), 7.83(1H,dd) IR(KBr) cm$^{-1}$: 1715, 1595, 1560

10c) Methyl 2-methyl-1-[[2'-(1H-tetrazol-5-yl)biphenyl-4-yl]methyl]indole-7-carboxylate A mixture of the N-trityltetrazole compound obtained in Working Example 10b) (0.57 g) in a mixture of 2N aqueous HCl (8 ml), methanol (4 ml) and THF (20 ml) was stirred at room temperature for 3.5 hours. After evaporation of the solvent, the residue was dissolved in chloroform. The solution was washed with water, dried and concentrated to dryness. The residue was purified by column chromatography on silica gel to give a pale yellow syrup. Recrystallization from chloroform-ether afforded pale yellow crystals (0.24 g, 66%), m.p. 180°–182° C.

| Elemental Analysis for C$_{25}$H$_{21}$N$_5$O$_2$·1.4H$_2$O: | | | |
|---|---|---|---|
| | C (%) | H (%) | N (%) |
| Calcd.: | 66.92; | 5.35; | 15.61 |
| Found: | 66.96; | 4.92; | 15.25 |

$^1$H-NMR(200 MHz,CDCl$_3$) δ: 2.52(3H,s), 3.80(3H,s), 5.57(2H,s), 6.47(1H,s), 6.78(2H,d), 7.0–7.6(7H,m), 7.72(1H,d), 8.22(1H,dd), 11.96(1H,brs)

10d) 2-Methyl-1-[[2'-(1H-tetrazol-5-yl)biphenyl-4-yl]methyl]indole-7-carboxylic acid A solution of the methyl ester compound obtained in Working Example 10c) (0.155 g) in a mixture of 1N aqueous lithium hydroxide (1.6 ml), methanol (2 ml) and THF (4 ml) was stirred at 70° C. for 5 hours. After evaporation of the solvent, the residue was poured into dilute hydrochloric acid and extracted with chloroform. The extract was washed with water, dried and concentrated to dryness. The residue was recrystallized from chloroform-ether to afford pale red crystals (0.112 g, 74%), m.p. 259°–261° C. (decomp.).

| Elemental Analysis for C$_{24}$H$_{19}$N$_5$O$_2$·0.5H$_2$O: | | | |
|---|---|---|---|
| | C (%) | H (%) | N (%) |
| Calcd.: | 68.89; | 4.82; | 16.74 |
| Found: | 69.22; | 4.63; | 16.73 |

$^1$H-NMR(200 MHz,DMSO-d$_6$) δ: 2.36(3H,s), 5.69(2H,s), 6.49(1H,s), 6.68(2H,d), 6.96(2H,d), 7.05(1H,t), 7.3–7.8(6H,m), IR(KBr) cm$^{-1}$: 1675, 1605, 1565

Working Example 11

2-Propyl-1-[[2'-(1H-tetrazol-5-yl)biphenyl-4-yl]methyl]-1H-pyrazolo[1,5-b][1,2,4]triazole-7-carboxylic acid 11a) Ethyl N-(4-ethoxycarbonylpyrazol-3-yl)butyroimidate A solution of ethyl 3-aminopyrazole-4-carboxylate (120 g) and 1,1,1-triethoxybutane (18.4 ml) in carbon tetrachloride (150 ml) was stirred at 80°–90° C. for 3 hours. After evaporation of the solvent, the residue was purified by column chromatography on silica gel to give a colorless syrup (19.2 g, 98%).

$^1$H-NMR(200 MHz,CDCl$_3$) δ: 0.84(3H,t), 1.30(3H,t), 1.36(3H,t), 1.46–1.65(2H,m), 2.22(2H,t), 4.23(2H,q), 4.30(2H,q), 5.80(1H,brs), 7.91(1H,s) IR(neat) cm$^{-1}$: 3175, 2975, 1710, 1665, 1568, 1552, 1502

11b) Ethyl 2-propylpyrazolo[1,5-b][1,2,4]triazole-7-carboxylate

The title compound was prepared according to the method as disclosed in Japanese Patent Application Laid Open No. 149582/1990.

A solution of the imidate compound obtained in Working Example 11a) (19.6 g) and hydroxylamine hydrochloride (53.8 g) in DMF (250 ml) was stirred at room temperature for 17 hours. The reaction mixture was concentrated to dryness. The resulting residue was extracted with ethyl acetate. The extract was washed with water, dried and concentrated to dryness.

To a stirred solution of the resulting residue and p-toluenesulfonic chloride (14.8 g) in DMF (150 ml) was added pyridine (12.6 g) under ice-cooling and the mixture was stirred at room temperature for 2.5 hours followed by concentration to dryness. The resulting residue was extracted with ethyl acetate. The extract was washed with water, dried and concentrated to dryness. The residue was purified by column chromatography on silica gel to afford the tosyl derivative as a colorless syrup (5.7 g).

A solution of the syrup and pyridine (1.3 ml) in ethanol (100 ml) was heated under reflux for 3 hours. The reaction mixture was concentrated to dryness. The resulting residue was dissolved in ethyl acetate, washed with water, dried and concentrated to dryness. The residue was purified by column chromatography on silica gel to afford crystals. Recrystallization from dichloromethane afforded colorless crystals (2.3 g, 13%), m.p. 214°–215° C.

$^1$H-NMR(200 MHz,CDCl$_3$) δ: 1.04(3H,t), 1.38(3H,t), 1.76–1.95(2H,m), 2.85(2H,t), 4.33(2H,q), 7.98(1H,s), 11.12(1H,brs) IR(KBr) cm$^{-1}$: 2970, 2800–2200, 1700, 1630, 1550, 1483

11c) Ethyl 2-propyl-1-[[2'-(N-trityltetrazol-5-yl)biphenyl-4-yl]methyl]-1H-pyrazolo[1,5-b][1,2,4]triazole-7-carboxylate To an ice-cooled, stirred solution of the resulting pyrazolotriazole (0.5 g) in DMF (8 ml) was added sodium hydride (60% dispersion in mineral oil, 0.09 g) under nitrogen atmosphere and the mixture was stirred for 30 minutes. To the reaction mixture was added a solution of 5-(4'-bromomethylbiphenyl-2-yl)-N-trityltetrazole (1.4 g) in DMF (15 ml) and the reaction mixture was stirred under ice-cooling for 1 hour and then at room temperature for 18 hours. The reaction mixture was concentrated to dryness. The resulting residue was dissolved in ethyl acetate, washed with water, dried and concentrated to dryness. The residue was purified by column chromatography on silica gel to afford crude crystals. Recrystallization from ethyl acetate-hexane afforded colorless crystals (1.35 g, 86%), m.p. 106°–108° C.

$^1$H-NMR(200 MHz,CDCl$_3$) δ: 0.91(3H,t), 1.25(3H,t), 1.61–1.80(2H,m), 2.52(2H,t), 4.21(2H,q), 5.61(2H,s), 6.90–6.95(8H,m), 7.13(2H,d), 7.19–7.36(10H,m), 7.45–7.51(2H,m), 7.89–7.94(1H,m), 8.02(1H,s) IR(KBr) cm$^{-1}$: 2970, 1700, 1595, 1538, 1470

11d) Ethyl 2-propyl-1-[[2'-(1H-tetrazol-5-yl)biphenyl-4-yl]methyl]-1H-pyrazolo[1,5-b][1,2,4]triazole-7-carboxylate A solution of the N-trityltetrazol compound obtained in Working Example 11c) (1.42 g) and 2N aqueous HCl (10 ml) in THF (60 ml) was stirred at room temperature for 20 hours. After evaporation of the solvent, the dry residue was dissolved in ethyl acetate. The solution was washed with water, dried and concentrated to dryness. The residue was purified by column chromatography on silica gel to give crude crystals. Recrystallization from ethyl acetate-hexane afforded colorless crystals (0.68 g, 73%), m.p. 221°–223° C.

$^1$H-NMR(200 MHz,DMSO-d$_6$) δ: 0.91(3H,t), 1.15(3H,t), 1.52–1.70(2H,m), 2.70(2H,t), 4.16(2H,q), 5.70(2H,s), 7.09(2H,d), 7.15(2H,d), 7.50–7.72(4H,m), 7.96(1H,s) IR(KBr) cm$^{-1}$: 2975, 2800–2200, 1705, 1607, 1540, 1479

11e) 2-Propyl-1-[[2'-(1H-tetrazol-5-yl)biphenyl-4-yl]methyl]-1H-pyrazolo[1,5-b][1,2,4]triazole-7-carboxylic acid In substantially the same manner as Working Example 10d), the ethyl ester compound obtained in Working Example 11d) was hydrolyzed with alkali to afford the above compound.

Working Example 12

2-Propyl-1-[[2'-(1H-tetrazol-5-yl)biphenyl-4-yl]methyl]-1H-imidazo[1,2-c]imidazole-7-carboxamide 12a) 2-Propylimidazo[1,2-c]imidazole-7-carboxamide A solution of 4-aminoimidazole-5-carboxamide hydrochloride (10 g) and sodium hydride (3.7 g) in DMF (200 ml) was stirred at room temperature for 15 minutes followed by addition of 1-bromo-2-pentane (20 g) and stirring at room temperature for 40 hours.

After removal of the solvent, the residue was mixed with ethyl acetate-isopropyl ether and the resulting precipitate was separated by filtration. The resultant powders were washed with water and recrystallized from ethanol-isopropyl ether to afford pale yellow crystals (5.7 g, 48%).

$^1$H-NMR(200 MHz,DMSO-d$_6$) δ: 0.91(3H,t), 1.64(2H,m), 2.51(2H,t), 6.70(2H,brs), 7.12(1H,s), 7.49(1H,s), 11.44(1H,s)

12b) 2-Propylimidazo[1,2-c]imidazole-7-carbonitrile

A solution of the carboxamide compound obtained in Working Example 12a) (5.0 g) in phosphorous oxychloride (50 ml) was stirred at room temperature for 4 days. After concentration of the reaction mixture, the resulting syrup was poured into ice-water followed by neutralization with 2N NaOH. The mixture was extracted with ethyl acetate and the extract was washed with water, dried and concentrated to dryness. The residue was purified by column chromatography on silica gel to give pale brown powders. Recrystallization from ethyl acetate-dichloromethane afforded crystalline powders (2.2 g, 49%), m.p. 221°–223° C.

$^1$H-NMR(200 MHz,DMSO-d$_6$) δ: 0.92(3H,t), 1.64(2H,m), 2.54(2H,t), 7.28(1H,s), 7.65(1H,s), 11.90(1H,s)

12c) 2-Propyl-1-[[2'-(N-trityltetrazol-5-yl)biphenyl-4-yl]methyl]-1H-imidazo[1,2-c]imidazole-7-carbonitrile A solution of the carbonitrile compound obtained in Working Example 12b) (0.5 g) and sodium hydride (60% dispersion in mineral oil, 0.17 g) in DMF (25 ml) was stirred at room temperature for 30 minutes. To the reaction mixture was added 5-(4'-bromomethylbiphenyl-2-yl]-N-trityltetrazole (2.1 g) and the reaction mixture was stirred at room temperature for 18 hours. The reaction mixture was concentrated to dryness. To the resulting residue was added ethyl acetate and water, and the organic layers were washed with water, dried and concentrated to dryness. The residue was purified by column chromatography on silica gel to afford pale brown powders (0.76 g, 41%).

$^1$H-NMR(200 MHz,CDCl$_3$) δ: 0.94(3H,t), 1.58(2H,m), 2.39(2H,t), 5.08(2H,s), 6.8–7.2(24H,m), 7.85–7.95(1H,m)

12d) 2-Propyl-1-[[2'-(1H-tetrazol-5-yl)biphenyl-4-yl]methyl]-1H-imidazo[1,2-c]imidazole-7-carbonitrile To a solution of the trityl compound obtained in Working Example 12c) (0.4 g) in a mixture of methanol (10 ml) and tetrahydrofuran (10 ml) was added 1N aqueous HCl (5 ml) and the reaction mixture was stirred at room temperature for 4 hours. The reaction mixture was concentrated to dryness. To the resulting residue was added water, and the mixture was extracted with ethyl acetate. The extract was washed with water, dried and concentrated to dryness. The residue was purified by column chromatography on silica gel to give a pale brown syrup (0.19 g, 74%).

12e) 2-Propyl-1-[[2'-(1H-tetrazol-5-yl)biphenyl-4-yl]methyl]-1H-imidazo[1,2-c]imidazole-7-carboxamide.-sodium salt A solution of the carbonitrile compound obtained in Working Example 12d) (0.18 g) in a mixture of methanol (2 ml) and 2.5N aqueous NaOH (10 ml) was heated under reflux for 3 hours. The reaction mixture was cooled and allowed to stand. Recrystallization of the resulting precipitate from aqueous methanol afforded pale yellow prisms (0.13 g, 64%), m.p.>300° C.

| Elemental Analysis for $C_{23}H_{21}N_8NaO \cdot H_2O$: | | | |
|---|---|---|---|
| | C (%) | H (%) | N (%) |
| Calcd.: | 59.22; | 4.97; | 24.02 |
| Found: | 59.40; | 4.71; | 24.08 |

$^1$H-NHR(200 MHz,DMSO-d$_6$) δ: 0.93(3H,t), 6.92(1H,brs), 6.95(2H,q), 7.04(2H,q), 7.25–7.40(3H,m), 7.50–7.60(1H,m)

Working Example 13

2,8-Diethoxy-7-[[2'-(1H-tetrazol-5-yl)biphenyl-4-yl]methyl]purine-6-carboxylic acid 13a) 5-Nitro-2,6-dioxo-1,2,3,6-tetrahydropyrimidine-4-carboxylic acid A solution of 6-methyl-5-nitrouracil (1.0 g) in fuming nitric acid (3.0 ml) was stirred at 90°–95° C. for 4hours. After cooling, the precipitated crystals were collected by filtration and washed with acetic acid and ether to afford pale yellow crystals (0.87 g, 74%), m.p.>300° C.

IR(Nujol) cm$^{-1}$: 3160, 1720, 1670

13b) Methyl 5-nitro-2,6-dioxo-1,2,3,6-tetrahydropyrimidine-4-carboxylate

A solution of the carboxylic acid compound obtained in Working Example 13a) (7.9 g) in methanol (40 ml) containing conc. sulfuric acid (3.0 ml) was heated under reflux for 15 hours. The reaction mixture was poured into ice-water and the resulting precipitated crystals were collected by filtration (6.94 g, 84%), m.p. 229°–230° C.

IR(Nujol) cm$^{-1}$: 3150, 1760, 1720, 1685 $^1$H-NMR(200 MHz,DMSO-d$_6$) δ: 3.89(3H,s)

13c) Methyl 2,6-dichloro-5-nitropyrimidine-4-carboxylate

To a stirred solution of the ester compound obtained in Working Example 13c) (15 g) and N,N-diethylaniline (2 ml) was added phosphorous oxychloride (6 ml) dropwise and the mixture was heated under reflux for 40 minutes followed by concentration to dryness. The resulting syrup was poured into ice-water and extracted with ether. The extract was washed succesively with 1N hydrochloric acid, aqueous sodium bicarbonate and water, dried and evaporated. To the residue was added hexane and the resulting precipitated crystals (1.1 g, 62%) were collected by filtration.

$^1$H-NMR(200MHz,CDCl$_3$) δ: 4.05(3H,s) IR(Nujol) cm$^{-1}$: 1775, 1725, 1550, 1525

13d) Methyl 6-amino-2-chloro-5-nitropyrimidine-4-carboxylate

To a stirred solution of the chloro compound obtained in Working Example 13d) (1.0 g) in chloroform (20 ml) under ice-cooling was added 2.4N solution of ammonia in methanol (5 ml) dropwise and the mixture was stirred at the same temperature for 30 minutes, followed by addition of water and extraction with chloroform. The extract was washed with water, dried and concentrated to dryness. To the residue was added isopropyl ether and the resulting precipitated crystals (0.74 g, 80%) were collected by filtration.

$^1$H-NMR(200MHz,CDCl$_3$) δ: 4.02(3H,s), 6.54(1H,brs), 8.06(1H,brs) IR(Nujol) cm$^{-1}$: 3200, 3280, 3170, 1735, 1630

13e) Methyl 6-amino-2-ethoxy-5-nitropyrimidine-4-carboxylate

A solution of the chloro compound obtained in Working Example 13d) (0.96 g) in pyridine (1.0 ml) and ethanol (20 ml) was heated under reflux for 3 hours. The reaction mixture was acidified with 1N hydrochloric acid followed by addition of water. Recrystallization of the resulting precipitated crystals from ethyl acetate-hexane afforded colorless prisms (0.8 g, 80%), m.p. 173°–17° C.

$^1$H-NMR(200 MHz,CDCl$_3$) δ: 1.42(3H,t), 4.00(3H,s), 4.45(2H,q), 6.19(2H,brs), 8.06(2H,brs) IR(Nujol) cm$^{-1}$: 3460, 3320

13f) Methyl 5,6-diamino-2-ethoxypyrimidine-4-carboxylate

To a stirred solution of the nitro compound obtained in Working Example 13e) (1.0 g) in acetone (20 ml) was added NaHCO$_3$ (4.5 g) and water (20 ml) followed by dropwise addition of sodium dithionate under stirring at room temperature. The reaction mixture was stirred at room temperature for 1 hour and extracted with chloroform. The extract was washed with water, dried and concentrated to dryness to afford a crude product (0.86 g, 91%).

$^1$H-NMR(200 MHz,DMSO-d$_6$) δ: 1.34(3H,t), 3.89(3H,s), 4.26(2H,q), 5.91(2H,brs), 6.34(2H,brs) IR(Nujol) cm$^{-1}$: 3430, 3400, 3350, 3275, 3220, 3160, 1695, 1660, 1620

13g) Methyl 2,8-diethoxypurine-6-carboxylate

A solution of the diamino compound obtained in Working Example 13f) (0.285 g), tetraethoxymethane (0.52 g) and acetic acid (0.09 g) in dioxane (3 ml) was stirred at 110° C. for 2.5 hours. The reaction mixture was concentrated to dryness. To the resulting residue was added isopropyl ether to give pale yellow prisms (0.328 g, 92%), m.p. 100°–101° C.

$^1$H-NMR(200 MHz,CDCl$_3$) δ: 1.44(3H,t), 1.51(3H,t), 4.04(3H,s), 4.50(2H,q), 4.75(2H,q), 9.40(1H,brs) IR(Nujol) cm$^{-1}$: 3270, 1695, 1590

13h) Methyl 2,8-diethoxy-7-[[2'-(N-trityltetrazol-5-yl)biphenyl-4-yl]methyl]purine-6-carboxylate A solution of the purine derivative obtained in Working Example 13g) (0.3 g) and sodium hydride (60% dispersion in mineral oil, 0.059 g) in DMF (15 ml) was stirred under ice-cooling for 15 minutes. To the reaction mixture was added 5-(4'-bromomethylbiphenyl-2-yl]-N-trityltetrazole (1.0 g) and the reaction mixture was stirred at 60° C. for 1.5 hours. To the reaction mixture was added water, and it was extracted with ethyl acetate. The extract was washed with water, dried and evaporated. The residue was purified by column chromatography on silica gel to give the title 7-substituted derivative as a powder (0.3 g, 36%).

$^1$H-NMR(200 MHz,CDCl$_3$) δ: 1.43(3H,t), 1.47(3H,t), 3.76(3H,s), 7.04(2H,d), 7.19–7.53(12H,m), 7.86–7.94(1H,m)

13i) Methyl 2,8-diethoxy-7-[[2'-(1H-tetrazol-5-yl)biphenyl-4-yl]methyl]purine-6-carboxylate A solution of the trityl compound obtained in Working Example 13h) (0.3 g) and 1N aqueous HCl (3 ml) in a mixture of methanol (10 ml) and dichlorometane (5 ml) was stirred at room temperature for 2 hours. The reaction mixture was extracted with chloroform. The extract was washed with water, dried and concentrated to dryness. The residue was purified by column chromatography on silica gel to afford crystals. Recrystallization from ethyl acetate afforded colorless prisms (0.24 g, 81%), m.p. 198°–199° C.

| Elemental Analysis for $C_{25}H_{24}N_8O_4$: | | | |
|---|---|---|---|
| | C (%) | H (%) | N (%) |
| Calcd.: | 59.99; | 4.83; | 22.39 |
| Found: | 60.00; | 4.70; | 21.90 |

13j) 2,8-Diethoxy-7-[[2'-(1H-tetrazol-5-yl)biphenyl-4-yl]methyl]purine-6-carboxylic acid A solution of the tetrazol compound obtained in Working Example 13i) (0.124 g) in a mixture of 1N aqueous NaOH (0.8 ml) and methanol (5 ml) was stirred at room temperature for 1 hour. To the reaction mixture was was added water, and the mixture was acidified with 1N aqueous HCl (1.5 ml). Recrystallization of the resulting crystals from aqueous methanol afforded colorless prisms (0.08 g, 69%), m.p. 140°–141° C.

| Elemental Analysis for $C_{24}H_{22}N_8O_4 \cdot 0.5H_2O$: | | | |
|---|---|---|---|
| | C (%) | H (%) | N (%) |
| Calcd.: | 58.18; | 4.68; | 22.61 |
| Found: | 58.04; | 4.77; | 22.45 |

$^1$H-NMR(200 MHz,DMSO-d$_6$) δ: 1.34(3H,t), 1.40(3H,t), 4.36(2H,q), 4.67(2H,q), 5.48(2H,s), 7.03(4H,s), 7.46–7.72(4H,m) IR(Nujol) cm$^{-1}$: 1690, 1640, 1605, 1590

Working Example 14

Pivaloyloxymethyl 2-ethyl-4-oxo-9-[[2'-(1H-tetrazol-5-yl)biphenyl-4-yl]methyl]-4,9-dihydrothieno[2,3-b]quinoline-8-carboxylate 14a) 2-ethyl-4-oxo-9-[[2'-(N-trityltetrazol-5-yl)biphenyl-4-yl]methyl]-4,9-dihydrothieno[2,3-b]quinoline-8-carboxylic acid A solution of the 2-ethyl-4-oxo-9-[[2'-(1H-tetrazol-5-yl)biphenyl-4-yl]methyl]-4,9-dihydrothieno[2,3-b]quinoline-8-carboxylic acid obtained in Working Example 3) (0.25 g), triphenylmethyl chloride (0.143 g) and triethylamine (0.073 ml) in DMF (10 ml) was stirred at room temperature for 20 hours under N$_2$. The reaction mixture was concentrated to dryness and the residue was dissolved in chloroform, washed with water, dried and evaporated. The brown syrup was purified by column chromatography on silica gel to afford pale yellow crystals (0.23 g, 62%), m.p.>290° C.

$^1$H-NMR(200 MHz,CDCl$_3$) δ: 1.24(3H,t), 3.71(2H,q), 5.0–9.0(29H,m), IR(KBr) cm$^{-1}$: 1605, 1575, 1560, 1510

14b) Pivaloyloxymethyl 2-ethyl-4-oxo-9-[[2'-(N-trityl-tetrazol-5-yl)biphenyl-4-yl]methyl]-4,9-dihydrothieno[2,3-b]quinoline-8-carboxylate To a solution of the trityl compound obtained in Working Example 14a) (0.216 g) in DMF (9 ml) was added K$_2$CO$_3$ (0.05 g) and pivaloyloxymethyl iodide (0.1 g) and the reaction mixture was stirred at room temperature for 2.5 hours. The reaction mixture was poured into ice-water and extracted with ethyl acetate. The extract was washed with water, dried and evaporated. The brown syrup was purified by column chromatography on silica gel to afford pale yellow powders (0.204 g, 82%).

$^1$H-NMR(200 MHz,CDCl$_3$) δ: 1.20(9H,s), 1.24(3H,t), 2.66(2H,q), 5.37(2H,s), 5.77(2H,s), 6.64(2H,d), 6.8–7.5(22H,m), 7.87(2H,dt), 8.79(1H,dd) IR(KBr) cm$^{-1}$: 1750, 1735, 1625, 1585, 1510

14c) Pivaloyloxymethyl 2-ethyl-4-oxo-9-[[2'-(1H-tetrazol-5-yl)biphenyl-4-yl]methyl]-4,9-dihydrothieno[2,3-b]quinoline-8-carboxylate A solution of the pivaloyloxymethyl ester obtained in Working Example 14b) (0.1 g) in a mixture of 1N hydrochloric acid (2.0 ml), methanol (5.0 ml) and THF (1.0 ml) was stirred at room temperature for 6.5 hours. The reaction mixture was extracted with chloroform. The extract was washed with water, dried and concentrated to dryness. The syrup was purified by column chromatography on silica gel to afford pale yellow powders (0.026 g, 34%), m.p. 146°–152° C.

$^1$H-NMR(200 MHz,CDCl$_3$) δ: 1.22(9H,s), 1.30(3H,t), 2.80(2H,q), 5.44(2H,s), 5.84(2H,s), 6.83(2H,d), 6.96(2H,d), 7.22(1H,s), 7.3–7.6(4H,m), 7.69(1H,d), 7.90(1H,dd), 8.73(1H,dd) IR(KBr) cm$^{-1}$: 1750, 1735, 1610, 1580, 1550, 1510

Working Example 15

1-(Cyclohexyloxycarbonyloxy)ethyl 2-ethyl-4-oxo-9-[[2'-(1H-tetrazol-5-yl)biphenyl-4-yl]methyl]-4,9-dihydrothieno[2,3-b]quinoline-8-carboxylate 15a) 1-(Cyclohexyloxycarbonyloxy)ethyl 2-ethyl-4-oxo-9-[[2'-(N-trityltetrazol-5-yl)biphenyl-4-yl]methyl]-4,9-dihydrothieno[2,3-b]quinoline-8-carboxylate To a solution of the trityl compound obtained in Working Example 14a) (0.25 g) in DMF (10 ml) was added K$_2$CO$_3$ (0.07 g) and cyclohexyl 1-iodoethyl carbonate (0.15 g) and the reaction mixture was stirred at room temperature for 6 hours. The reaction mixture was poured into iced water and extracted with ethyl acetate. The extract was washed with water, dried and concentrated to dryness. The brown syrup was purified by column chromatography on silica gel to afford pale yellow powders (0.13 g, 42%).

$^1$H-NMR(200 MHz,CDCl$_3$) δ: 1.24(3H,t), 1.1–2.1(10H,m), 1.52(3H,d), 2.64(2H,q), 4.5–4.8(1H,m), 5.43(2H,q), 6.63(2H,d), 6.8–8.0(25H,m), 8.79(1H,dd) IR(KBr) cm$^{-1}$: 1750, 1730, 1630, 1585, 1510

15b) 1-(Cyclohexyloxycarbonyloxy)ethyl 2-ethyl-4-oxo-9-[[2'-(1H-tetrazol-5-yl)biphenyl-4-yl]methyl]-4,9-dihydrothieno[2,3-b]quinoline-8-carboxylate A solution of the ester obtained in Working Example 15a) (0.128 g) in a mixture of 1N hydrochloric acid (9 ml), methanol (1 ml) and THF (7 ml) was stirred at room temperature for 3 hours. The reaction mixture was extracted with chloroform. The extract was washed with water, dried and concentrated to dryness. The residue was purified by column chromatography on silica gel to afford pale yellow crystalline powders (0.026 g, 72%), m.p. 143°–147° C. (decomp.).

| Elemental Analysis for $C_{37}H_{35}N_5O_6S \cdot 0.5H_2O$: | | | |
|---|---|---|---|
| | C (%) | H (%) | N (%) |
| Calcd.: | 64.71; | 5.28; | 10.20 |
| Found: | 64.75; | 5.38; | 10.28 |

$^1$H-NMR(200 MHz,CDCl$_3$) δ: 1.28(3H,T), 1.63(3H,D), 1.1–2.0(10H,M), 2.77(2H,q), 4.5–4.7(1H,m), 5.53(2H,q), 6.85(2H,q), 6.97(2H,d), 7.06(2H,d), 7.11(1H,s), 7.2–7.6(4H,m), 7.90(1H,dd), 8.04(1H,dd), 8.63(1H,dd)

Working Example 16

2-Ethyl-1-[[2'-(1H-tetrazol-5-yl)biphenyl-4-yl]methyl]indole-7-carboxylic acid

16a) Ethyl 2-nitro-3-(2-oxobutyl)benzoate

A stirred mixture of ethyl 3-methyl-2-nitrobenzoate (0.96 g) and N,N-dimethylpropionamide diethyl acetal (2.3 g) was heated at 145° C. for 36 hours. The reaction mixture was dissolved in ethyl acetate. The solution was washed with dilute hydrochloric acid and then water, dried and concentrated to dryness. The residue was purified by column chromatography on silica gel to give a pale brown syrup (0.36 g, 33%).

$^1$H-NMR(200 MHz,CDCl$_3$) δ: 1.09(3H,t), 1.35(3H,t), 2.55(2H,q), 3.75(2H,s), 4.36(2H,q), 7.4–7.7(2H,m), 7.90(1H,dd) IR(Neat) cm$^{-1}$: 1735, 1720, 1540

16b) Ethyl 2-ethyl-1-[[2'-(N-triphenylmethyltetrazol-5-yl)biphenyl-4-yl]methyl]indole-7-carboxylate A mixture of the compound obtained in Working Example 16a) (0.57 g) and 10% Pd/C (0.3 g) in THF (15 ml) was stirred under H$_2$ atmosphere for 3 hours. After removal of the catalyst by filtration, the filtrate was concentrated to dryness to give a pale yellow syrup (0.33 g).

To a mixture of the resulting syrup and N-triphenylmethyl 5-[4'-bromomethylbiphenyl-2-yl)tetrazole (1.8 g) in hexamethylphosphoric triamide (10 ml) was added sodium hydride (60% dispersion in mineral oil, 0.11 g) under nitrogen atmosphere and the mixture was stirred at room temperature for 2 hours. To the reaction mixture was added ethyl acetate. The mixture was washed with water, dried and concentrated to dryness. The pale brown syrup was purified by column chromatography on silica gel to give the title compound as pale yellow powders (876 mg, 58%).

$^1$H-NMR(200 MHz,CDCl$_3$) δ: 1.07(3H,t), 1.25(3H,t), 2.55(2H,q), 4.06(2H,q), 5.49(2H,s), 6.44(2H,s), 6.51(2H,d), 6.8–7.5(22H,m), 7.71(1H,d), 7.8–7.9(1H,m) IR(KBr) cm$^{-1}$: 1710, 1600, 1585, 1555

16c) Ethyl 2-ethyl-1-[[2'-(1H-tetrazol-5-yl)biphenyl-4-yl]methyl]indole-7-carboxylate A mixed solution of the compound obtained in Working Example 16b) (0.63 g) and 2N aqueous HCl (5 ml) in a mixture of methanol (2 ml) and THF (16 ml) was stirred at room temperature for 3.5 hours. After evaporation of the solvent, the residue was dissolved in chloroform. The solution was washed with water, dried and concentrated to dryness. The syrup was purified by column chromatography on silica gel to give crude crystals. Recrystallization from chloroform-ethyl acetate-hexane afforded pale yellow crystals (0.265 g, 64%), m.p. 146°–148° C.

Elemental Analysis for C$_{27}$H$_{25}$N$_5$O$_2$.0.8H$_2$O:

|  | C (%) | H (%) | N (%) |
|---|---|---|---|
| Calcd.: | 69.60; | 5.75; | 15.03 |
| Found: | 69.62; | 5.54; | 14.95 |

$^1$H-NMR(200 MHz,CDCl$_3$) δ: 1.33(3H,t), 1.42(3H,t), 2.84(2H,q), 4.25(2H,q), 5.59(2H,s), 6.49(1H,s), 6.76(2H,d), 7.0–7.6(7H,m), 7.74(1H,dd), 8.1–8.3(1H,m) IR(KBr) cm$^{-1}$: 1700, 1600, 1580, 1565, 1555

16d) 2-Ethyl-1-[[2'-(1H-tetrazol-5-yl)biphenyl-4-yl]methyl]indole-7-carboxylic acid A solution of the ethyl ester compound obtained in Working Example 16c) (0.15 g) and 2N aqueous lithium hydroxide (4.0 ml) in methanol (3 ml) was stirred at 80° C. for 6 hours. After evaporation of methanol, dilute hydrochloric acid was added to the residue. The mixture was extracted with chloroform. The extract was washed with water, dried and concentrated to dryness. The residue was washed with ethyl acetate to afford pale yellow crystals (0.007 g, 50%), m.p. 248°–249° C.

Elemental Analysis for C$_{25}$H$_{21}$N$_5$O$_2$.0.2H$_2$O:

|  | C (%) | H (%) | N (%) |
|---|---|---|---|
| Calcd.: | 70.31; | 5.05; | 16.40 |
| Found: | 70.38; | 5.17; | 16.31 |

$^1$H-NMR(200 MHz,DMSO-d$_6$) δ: 1.27(3H,t), 2.68(2H,q), 5.69(2H,s), 6.49(1H,s), 6.65(2H,d), 6.94(2H,d), 7.05(1H,t), 7.4–7.7(5H,m), 7.71(1H,d) IR(KBr) cm$^{-1}$: 1670, 1600, 1585, 1555

Working Example 17

2-Propyl-1-[[2'-(1H-tetrazol-5-yl)biphenyl-4-yl]methyl]indole-7-carboxylic acid

17a) Ethyl 2-nitro-3-(2-oxopentyl)benzoate

In substantially the same manner as Working Example 16a), the above compound (0.22 g, 27%) was obtained from ethyl 3-methyl-2-nitrobenzoate (0.6 g) and N,N-dimethylbutyrylamide diethyl acetal (1.3 g).

$^1$H-NMR(200 MHz,CDCl$_3$) δ: 0.93(3H,t), 1.35(3H,t), 1.5–1.7(2H,m), 2.50(2H,t), 3.74(2H,s), 4.36(2H,q), 7.47(1H,dd), 7.55(1H,t), 7.90(1H,dd) IR(Neat) cm$^{-1}$: 1735, 1720, 1605, 1580, 1540

17b) Ethyl 2-propylindole-7-carboxylate

A mixture of the compound obtained in Working Example 17a) (0.43 g) and 10% Pd/C (0.2 g) in THF (15 ml) was stirred under H$_2$ atmosphere for 2 hours. After removal of the catalyst by filtration, the filtrate was concentrated to dryness to give a syrup which was purified by column chromatography on silica gel to give a pale yellow syrup (0.3 g, 83%).

$^1$H-NMR(200 MHz,CDCl$_3$) δ: 1.02(3H,t), 1.45(3H,t), 1.7–1.9(2H,m), 2.78(2H,t), 4.45(2H,q), 6.28(1H,s), 7.09(1H,t), 7.73(1H,d), 7.80(1H,d), 9.6(1H,brs)

17c) Ethyl 2-propyl-1-[[2'-(N-triphenylmethyltetrazol-5-yl)biphenyl-4-yl]methyl]indole-7-carboxylate A mixture of the compound obtained in Working Example 17b) (0.3 g), N-triphenylmethyl-5-[4'-bromomethylbiphenyl-2-yl)tetrazole (1.1 g) and sodium hydride (60% dispersion in mineral oil, 0.07 g) in hexamethylphosphoric triamide (HMPA) (6 ml) was stirred at room temperature for 2.5 hours. To the reaction mixture was added ethyl acetate. The mixture was washed with water, dried and concentrated to dryness. The residue was purified by column chromatography on silica gel to give pale yellow powders (0.59 g, 64%).

$^1$H-NMR(200 MHz,CDCl$_3$) δ: 0.93(3H,t), 1.08(3H,t), 1.6–1.8(2H,m), 2.56(2H,t), 4.05(2H,q), 5.50(2H,s), 6.45(1H,s), 6.49(2H,d), 6.8–7.5(22H,m), 7.72(1H,d), 7.83(1H,dd) IR(KBr) cm$^{-1}$: 1710, 1600, 1560

17d) Ethyl 2-propyl-1-[[2'-(1H-tetrazol-5-yl)biphenyl-4-yl]methyl]indole-7-carboxylate A mixture of the compound obtained in Working Example 17c) (0.57 g) in a mixture of 2N aqueous HCl (8 ml), methanol (4 ml) and THF (10 ml) was stirred at room temperature for 4.5 hours. After evaporation of the solvent, the residue was dissolved in chloroform.

The solution was washed with water, dried and concentrated to dryness. The residue was purified by column chromatography on silica gel to give crystals which were recrystallized from chloroform-hexane to afford colorless crystals (0.27 g, 72%), m.p. 142°–143° C.

| Elemental Analysis for $C_{28}H_{27}N_5O_2$: | | | |
|---|---|---|---|
| | C (%) | H (%) | N (%) |
| Calcd.: | 72.24; | 5.85; | 15.04 |
| Found: | 72.21; | 5.87; | 14.80 |

$^1$H-NMR(200 MHz,CDCl$_3$) δ: 1.08(3H,t), 1.33(3H,t), 1.7–2.0(2H,m), 2.80(2H,t), 4.24(2H,q), 5.58(2H,s), 6.48(1H,s), 6.74(2H,d), 7.0–7.6(7H,m), 7.73(1H,dd), 8.22(1H,dd)

17e) 2-Propyl-1-[[2'-(1H-tetrazol-5-yl)biphenyl-4-yl]methyl]indole-7-carboxylic acid A solution of the compound obtained in Working Example 17d) (0.17 g) and 1N aqueous lithium hydroxide (2.0 ml) in a mixture of THF (4 ml) and methanol (2 ml) was stirred at 75° C. for 6.5 hours. After evaporation of the solvent, dilute hydrochloric acid was added to the residue. The mixture was extracted with chloroform. The extract was washed with water, dried and concentrated to dryness. The residue was recrystallized from methanol-chloroform-ether to afford pale red crystals (0.11 g, 69%), m.p. 221°–222° C.

| Elemental Analysis for $C_{26}H_{23}N_5O_2.0.4H_2O$: | | | |
|---|---|---|---|
| | C (%) | H (%) | N (%) |
| Calcd.: | 70.22; | 5.39; | 15.75 |
| Found: | 70.32; | 5.15; | 15.53 |

$^1$H-NMR(200 MHz,DMSO-d$_6$) δ: 0.97(3H,t), 1.5–1.8(2H,m), 2.65(2H,t), 5.69(2H,s), 6.49(1H,s), 6.64(2H,d), 6.94(2H,d), 7.0–7.8(9H,m) IR(KBr) cm$^{-1}$: 1675, 1600, 1560

Working Example 18

Pivaloyloxymethyl 2-propyl-1-[[2'-(1H-tetrazol-5-yl)biphenyl-4-yl]methyl]indole-7-carboxylate 18a) Pivaloyloxymethyl 2-propyl-1-[[2'-(N-triphenylmethyltetrazol-5-yl)biphenyl-4-yl]methyl]indole-7-carboxylate A mixture of the compound obtained in Working Example 17e) (0.123 g), triphenylmethyl chloride (0.086 g) and triethylamine (0.043 ml) in DMF (5 ml) was stirred at room temperature for 20 hours. After evaporation of the solvent, the syrup was dissolved in chloroform. The solution was washed with dilute hydrochloric acid and then water, dried and concentrated to dryness. The syrup was purified by column chromatography on silica gel to give white powders (125 mg).

A mixture of the white powder, pivaloyloxymethyl iodide (0.12 ml) and K$_2$CO$_3$ (0.08 g) in DMF (5 ml) was stirred at room temperature for 20 hours. The reaction mixture was extracted with ethyl acetate and the extract was washed with water, dried and concentrated to dryness. The syrup was purified by column chromatography on silica gel to afford pale yellow powders (126 mg, 55%).

$^1$H-NMR(200 MHz,CDCl$_3$) δ: 0.93(3H,t), 1.17(9H,s), 1.6–1.8(2H,m), 2.57(2H,t), 5.53(2H,s), 5.68(2H,s), 6.46(1H,s), 6.48(2H,d), 6.8–7.5(22H,m), 7.77(1H,d), 7.8–7.9(1H,m) IR(KBr) cm$^{-1}$: 1750, 1725, 1600, 1555

18b) Pivaloyloxymethyl 2-propyl-1-[[2'-(1H-tetrazol-5-yl)biphenyl-4-yl]methyl]indole-7-carboxylate A solution of the pivaloyloxymethyl ester obtained in Working Example 18a) (0.12 g) in a mixture of 2N hydrochloric acid (4 ml), methanol (2 ml) and THF (4 ml) was stirred at room temperature for 4 hours. To the reaction mixture was added dilute hydrochloric acid and the mixture was extracted with chloroform. The extract was washed with water, dried and concentrated to dryness. The residue was purified by column chromatography on silica gel to afford a syrup. Crystallization from ether-hexane afforded colorless crystals (61 mg, 73%), m.p. 101°–103° C.

| Elemental Analysis for $C_{32}H_{33}N_5O_4.0.2H_2O$: | | | |
|---|---|---|---|
| | C (%) | H (%) | N (%) |
| Calcd.: | 69.22; | 6.06; | 12.61 |
| Found: | 69.26; | 6.00; | 12.50 |

$^1$H-NMR(200 MHz,CDCl$_3$) δ: 1.04(3H,t), 1.18(9H,s), 1.7–1.9(2H,m), 2.72(2H,t), 5.56(2H,s), 5.79(2H,s), 6.48(1H,s), 6.79(2H,d), 7.0–7.6(7H,m), 7.76(1H,d), 8.09(1H,dd) IR(KBr) cm$^{-1}$: 1750, 1730, 1605, 1555

Working Example 19

2-Butyl-1-[[2-(2-carboxyphenyl)pyridin-5-yl]methyl]-benzimidazole-7-carboxylic acid 19a) 2-cyanophenyl trifluoromethanesulfonate To a stirred solution of 2-cyanophenol (4.0 g) and diisopropylethylamine (4.8 g) in methylene chloride (40 ml) was added trifluoromethanesulfonic anhydride (9.7 g) dropwise under ice-cooling. The reaction mixture was stirred for 1 hour and washed with aqueous sodium bicarbonate and water, dried and concentrated to dryness. The residue was purified by column chromatography on silica gel to give a pale yellow syrup (7.4 g, 87%).

$^1$H-NMR(200 MHz,CDCl$_3$) δ: 7.50–7.58(2H,m), 7.71–7.82(2H,m) IR(neat) cm$^{-1}$: 2230, 1600, 1485, 1430, 1250, 1220, 1160, 1135, 1090, 890, 785, 770, 755, 700

19b) 2-(5-Methyl-2-pyridyl)benzonitrile

To a stirred solution of 2-bromo-5-methylpyridine (1.2 g) in THF (15 ml) at −78° C. under argon atmosphere was added 1.65M solution of butyl lithium in hexane (4.4 ml) dropwise and the reaction mixture was stirred for 10 minutes followed by addition of zinc chloride (1M ether solution, 7.2 ml) and then stirring at 0° C. for 30 minutes. The resulting zinc compound was poured into an ice-cooled, stirred mixture of 2-cyanophenyl trifluoromethanesulfonate (1.2 g) and tetrakistriphenylphosphine paladium (Pd(PPh$_3$)$_4$, 0.42 g) in THF (15 ml) under argon atmosphere and the mixture was stirred for 15 hours and concentrated to dryness. The residue was purified by column chromatography on silica gel to give crystals. Recrystallization from hexane afforded colorless needles (0.4 g, 29%), m.p. 80°–81° C.

$^1$H-NMR(200 MHz,CDCl$_3$) δ: 2.43(3H,s), 7.49(1H,dt), 7.63–7.86(5H,m), 8.61(1H,s) IR(KBr) cm$^{-1}$: 2210, 1465, 1375, 825, 765, 740, 725

19c) 2-(5-Bromomethyl-2-pyridyl)benzonitrile

A solution of the compound obtained in Working Example 19b) (0.39 g), N-bromosuccinimide (0.51 g) and benzoyl peroxide (5 mg) in carbon tetrachloride (10 ml) was heated under reflux in light radiation for 2 hours. After removal of insoluble materials by filtration, the filtrate was concentrated. The residue was purified by column chromatography on silica gel to afford colorless crystals (0.37 g, 67%).

$^1$H-NMR(200 MHz,CDCl$_3$) δ: 4.55(2H,s), 7.53(1H,dt), 7.67–7.92(5H,m), 8.79(5H,d)

19d) Methyl 2-[N-[2-(2-cyanophenyl)pyridin-5-yl]methyl-N-valeryl]amino-3-nitrobenzoate A solution of methyl 3-nitro-2-valerylaminobenzoate (0.37 g) and sodium hydride (60% dispersion in mineral oil, 0.06 g) in DMF (4 ml) was stirred under ice-cooling for 10 minutes. To the reaction mixture was added 2-(5-bromomethyl-2-pyridyl)benzonitrile (0.37 g) and the mixture was stirred at room temperature for 2 hours. To the reaction mixture was added water, and the mixture was extracted with ethyl acetate. The extract was washed with water, dried and concentrated to dryness. The residue was purified by column chromatography on silica gel to give a pale yellow syrup (0.55 g, 86%).

$^1$H-NMR(200 MHz,CDCl$_3$) δ: 0.85(3H,t), 1.17–1.36(2H,m), 1.59–1.75(2H,m), 2.05–2.15(2H,m), 3.70(3H,s), 4.75(1H,d), 4.94(1H,d), 7.51(1H,dt), 7.60–7.85(6H,m), 8.00(1H,dd), 8.13(1H,dd), 8.35(1H,m)

19e) Methyl 2-butyl-1-[[2-(2-methoxycarbonylphenyl)-pyridin-5-yl]methyl]benzimidazole-7-carboxylate A solution of the compound obtained in Working Example 19d) (0.55 g) and iron powders (0.45 g) in a mixture of conc. hydrochloric acid (1.4 ml) and methanol (10 ml) was heated under reflux for 22 hours. After removal of insoluble materials by filtration, the filtrate was neutralized with 1N aqueous NaOH and extracted with ethyl acetate. The extract was washed with water, dried and concentrated to dryness. The residue was purified by column chromatography on silica gel to give crystals. Recrystallization from ethyl acetate-hexane afforded pale blue crystals (0.25 g, 45%), m.p. 117°–118° C.

$^1$H-NMR(200 MHz,CDCl$_3$) δ: 0.97(3H,s), 1.39–1.58(2H,m), 1.82–1.98(2H,m), 2.94(2H,t), 3.62(3H,s), 3.77(3H,s), 5.84(2H,s), 7.11(1H,dd), 7.23–7.35(2H,m), 7.40–7.58(3H,m), 7.69(1H,dd), 7.79(1H,d), 7.97(1H,dd), 8.37(1H,d) IR(neat) cm$^{-1}$: 1720, 1440, 1420, 1390, 1280, 1260, 1190, 1115, 1100, 760, 750

19f) 2-Butyl-1-[[2-(2-carboxyphenyl)pyridin-5-yl]methyl]benzimidazole-7-carboxylic acid A solution of the compound obtained in Working Example 19e) (0.13 g), 1N aqueous NaOH (1.7 ml) in methanol (6 ml) was heated under reflux for 3 hours. The reaction mixture was neutralized with 1N aqueous hydrochloric acid (1.7 ml) and concentrated to dryness. Recrystallization of the resulting crystals from methanol-ethyl acetate afforded colorless needles (0.05 g, 42%), m.p. 257°–258° C. (decomp.).

| Elemental Analysis for C$_{25}$H$_{23}$N$_3$O$_4$: | | | |
|---|---|---|---|
| | C (%) | H (%) | N (%) |
| Calcd.: | 69.92; | 5.40; | 9.78 |
| Found: | 69.63; | 5.30; | 9.43 |

$^1$H-NMR(200 MHz,DMSO-d$_6$) δ: 0.89(3H,t), 1.29–1.48(2H,m), 1.68–1.83(2H,m), 2.90(2H,t), 5.92(2H,s), 7.22–7.30(2H,m), 7.44–7.57(4H,m), 7.63–7.68(2H,m), 7.86(1H,dd), 8.19(1H,d) IR (KBr) cm$^{-1}$: 1690, 1240, 1200

Working Example 20

Pivaloyloxymethyl 2-propyl-1-[[2'-(1H-tetrazol-5-yl)biphenyl-4-yl]methyl]-1H-pyrazolo[1,5-b][1,2,4]triazole-7-carboxylate 20a) Pivaloyloxymethyl 2-propyl-1-[[2'-(N-trityltetrazol-5-yl)-biphenyl-4-yl]methyl]-1H-pyrazolo[1,5-b][1,2,4]triazole-7-carboxylate A solution of the compound obtained in Working Example 11) (0.1 g), triphenylmethyl chloride (0.08 g) and triethylamine (0.04 ml) in DMF (2 ml) was stirred at room temperature for 4 hours. The reaction mixture was concentrated to dryness and the residue was dissolved in chloroform, washed with water, dried and evaporated.

To a solution of the white powders thus obtained (0.16 g), K$_2$CO$_3$ (0.05 g) and pivaloyloxymethyl iodide (0.085 g) in DMF (4 ml) was stirred at room temperature for 14 hours. The reaction mixture was concentrated to dryness and the residue was dissolved in ethyl acetate. The solution was washed with water, dried and concentrated to dryness. The residue was purified by column chromatography on silica gel to afford the title compound as white powders (0.14 g, 76%).

$^1$H-NMR(200 MHz,CDCl$_3$) δ: 0.92(3H,t), 1.17(9H,s), 1.62–1.80(2H,m), 2.53(2H,t), 5.58(2H,s), 5.80(2H,s), 6.90–6.94(8H,m), 7.12(2H,d), 7.19–7.36(10H,m), 7.42–7.53(2H,m), 7.89–7.94(1H,m), 8.05(1H,s) IR(KBr) cm$^{-1}$: 2970, 1748, 1713, 1600, 1538, 1473

20b) Pivaloyloxymethyl 2-propyl-1-[[2'-(1H-tetrazol-5-yl)biphenyl-4-yl]methyl]-1H-pyrazolo[1,5-b][1,2,4]triazole-7-carboxylate A solution of the compound obtained in Working Example 20a) (0.14 g) in a mixture of 2N hydrochloric acid (1.5 ml), methanol (4 ml) and THF (3 ml) was stirred at room temperature for 3 hours. The reaction mixture was concentrated to dryness and the residue was dissolved in ethyl acetate. The solution was washed with water, dried and evaporated. The residue was purified by column chromatography on silica gel to afford crude crystals. Recrystallization from ethyl acetate-hexane afforded colorless crystals (0.07 g, 71%), m.p. 157°–158° C.

| Elemental Analysis for C$_{28}$H$_{30}$N$_8$O$_4$: | | | |
|---|---|---|---|
| | C (%) | H (%) | N (%) |
| Calcd.: | 61.98; | 5.57; | 20.65 |
| Found: | 61.81; | 5.78; | 20.62 |

$^1$H-NMR(200 MHz,CDCl$_3$) δ: 1.01(3H,t), 1.11(9H,s), 1.70–1.89(2H,m), 2.70(2H,t), 5.62(2H,s), 5.84(2H,s), 7.15(2H,d), 7.21(2H,d), 7.41–7.46(1H,m), 7.51–7.66(2H,m), 8.08(1H,s), 8.08–8.13(1H,m) IR(KBr) cm$^{-1}$: 2980, 2800–2200, 1760, 1602, 1540, 1480

Working Example 21

2-Butyl-1-[[2-[2-(1H-tetrazol-5-yl)phenyl]pyridin-5-yl]methyl]benzimidazole-7-carboxylic acid 21a) Methyl 2-butyl-1-[[2-(2-cyanophenyl)pyridin-5-yl]methyl]benzimidazole-7-carboxylate A solution of the compound obtained in Working Example 19d) (0.62 g), FeCl$_3$· 6H$_2$O (20 mg) and activated carbon powders (50 mg) in methanol (20 ml) was heated under reflux for 30 minutes. To the heated reaction mixture was added a solution of hydrazine · hydrate (0.2 g) in methanol (2 ml) dropwise under reflux during 30 minutes and the mixture was heated under reflux for an additional 9 hour. After removal of insoluble materials by filtration, the filtrate was concentrated to dryness. A solution of the residue and p-toluenesulfonic acid (0.1 g) in toluene (20 ml) was heated under reflux for 3 hours, then washed with aqueous sodium bicarbonate and water and concentrated to dryness. The residue was purified by column chromatography on silica gel to afford crystals. Recrystallization from ethyl acetate afforded colorless needles (0.3 g, 54%), m.p. 155°–156° C.

$^1$H-NMR(200 MHz,CDCl$_3$) δ: 0.96(3H,t), 1.39–1.57(2H,m), 1.82–1.97(2H,m), 2.92(2H,t), 3.77(3H,s), 5.89(2H,s), 7.18–7.31(2H,m), 7.50(1H,dt), 7.63–7.81(5H,m), 7.97(1H,dd), 8.49(1H,d) IR(KBr) cm$^{-1}$: 2220, 1720, 1590, 1475, 1435, 1420, 1400, 1320, 1280 1255, 1190, 1140, 1110, 1020, 770, 760, 740

21b) Methyl 2-butyl-1-[[2-[2'-(1H-tetrazol-5-yl)phenyl]-pyridin-5-yl]methyl]benzimidazole-7-carboxylate A solution of the compound obtained in Example 21a) (0.3 g) and trimethylsilyl azide (0.43 g) in toluene (10 ml) was heated under reflux for 4 hours. The reaction mixture was concentrated to dryness followed by addition of methanol (6 ml) and 1N aqueous solution of hydrochloric acid (2.5 ml) to the residue. The mixture was stirred at room temperature for 10 minutes, neutralized with 1N aqueous NaOH (2.5 ml) and extracted with ethyl acetate. The extract was washed with water, dried and concentrated to dryness. The residue was purified by column chromatography on silica gel to give crystals. Recrystallization from ethyl acetate-methanol afforded colorless crystals (0.27 g, 82%), m.p. 191°–192° C. (decomp.).

| Elemental Analysis for C$_{26}$H$_{25}$N$_7$O$_2$: | | | |
|---|---|---|---|
| | C (%) | H (%) | N (%) |
| Calcd.: | 66.79; | 5.39; | 20.97 |
| Found: | 66.39; | 5.40; | 20.83 |

$^1$H-NMR(200 MHz, CDCl$_3$) δ: 0.91(3H,t), 1.32–1.50(2H,m), 1.73–1.88(2H,m), 2.77(2H,t), 3.75(3H,s), 5.83(2H,s), 7.21–7.29(3H,m), 7.49–7.62(3H,m), 7.73(1H,dd), 7.81(1H,dd), 8.11–8.16(1H,m), 8.31(1H,s)

21c) 2-Butyl-1-[[2-[2'-(1H-tetrazol-5-yl)phenyl]pyridin-5-yl]methyl]benzimidazole-7-carboxylic acid A solution of the compound obtained in Example 21b) in a mixture of methanol (2 ml) and 1N aqueous sodium hydroxide (1 ml) was heated under reflux for 1 hour. The reaction mixture was neutralized with 1N aqueous hydrochloric acid (1 ml) and concentrated to dryness. Recrystallization of the residue from chloroform-methanol afforded the title compound as colorless needles (0.0838 g, 49%).

$^1$H-NMR(200 MHz, DMSO-d$_6$) δ: 0.89(3H,t), 1.28–1.47(2H,m), 1.66–1.81(2H,m), 2.85(2H,t), 5.86(2H,s), 7.15–7.36(3H,m), 7.60–7.70(5H,m), 7.85(1H,dd), 8.04(1H,d)

| Elemental Analysis for C$_{25}$H$_{23}$N$_7$O$_2$.0.6CHCl$_3$: | | | |
|---|---|---|---|
| | C (%) | H (%) | N (%) |
| Calcd.: | 58.55; | 4.53; | 18.67 |
| Found: | 58.90; | 4.47; | 18.94 |

Working Example 22

2-Butyl-1-[[3-chloro-4-[2-(1H-tetrazol-5-yl)pyrrol-1-yl]phenyl]methyl]benzimidazole-7-carboxylic acid 22a) 1-(2-Chloro-4-methylphenyl)pyrrole The title compound was obtained as a syrup (18.7 g, 97%) from 2-chloro-4-methylaniline (13.2 g) and 2,5-dimethoxytetrahydrofuran (14.2 g) according to known methods (R. Jones, C. F. Candy and P. H. Wright, J. Chem. Soc., (C), 1970, 2563).

$^1$H-NMR(200 MHz, CDCl$_3$) δ: 2.38(3H,s), 6.33(2H,t), 6.88(2H,t), 7.12(1H,dd), 7.23(1H,d), 7.32(1H,d) IR(neat) cm$^{-1}$: 1510, 1330, 1090, 1010, 930, 860, 820, 720

22b) 1-(2-Chloro-4-methylphenyl)pyrrole-2-carboaldehyde

To ice-cooled DMF (4.0 g) was added phosphorous oxychloride (8.4 g) dropwise and the mixture was stirred at room temperature for 15 minutes. To the stirred reaction mixture was added a solution of 1-(2-chloro-4-methylphenyl)pyrrole (9.7 g) in DMF (8 ml) dropwise and the mixture was stirred at 50° C. for 1.5 hours followed by addition of ice-water. Stirring was continued for a while and then the mixture was made basic with potassium carbonate, and extracted with ethyl acetate. The extract was washed with water, dried and evaporated. The residue was purified by column chromatography on silica gel to give crystals. Recrystallization from ethyl acetate-hexane afforded yellow prisms (7.1 g, 59%), m.p. 111°–112° C.

$^1$H-NMR(200 MHz, CDCl$_3$) δ: 2.42(3H,s), 6.43(1H,dd), 6.91(1H,m), 7.11–7.26(3H,m), 7.34(1H,s), 9.49(1H,s) IR(neat) cm$^{-1}$: 1660, 1500, 1460, 1415, 1360, 1315, 1200, 1060, 1030, 865, 825, 765, 750, 710

22c) 1-(2-Chloro-4-methylphenyl)pyrrole-2-carbonitrile

A solution of the compound obtained in Working Example 22b) (2.2 g) and hydroxylamine hydrochloride (1.2 g) in pyridine (9 ml) was stirred at room temperature for 15 minutes followed by addition of acetic anhydride (4.1 g) and then the mixture was heated under reflux for 1 hour. To the reaction mixture was added water, and the mixture was extracted with ethyl acetate. The extract was washed with water, dried and concentrated to dryness. The residue was purified by column chromatography on silica gel to give a brown syrup (2.2 g, quantitatively).

$^1$H-NMR(200 MHz,CDCl$_3$) δ: 2.42(3H,s), 6.35(1H,dd), 6.94–6.99(2H,m), 7.19(1H,d), 7.30(1H,d), 7.38(1H,s) IR(neat) cm$^{-1}$: 2200, 1500, 1440, 1405, 1340, 1320, 1170, 1060, 1020, 860, 815, 730

22d) 1-(2-Chloro-4-bromomethylphenyl)pyrrole-2-carbonitrile

A solution of the compound obtained in Working Example 22c) (2.2 g), N-bromosuccinimide (2.0 g) and benzoyl peroxide (24 mg) in carbon tetrachloride (100 ml) was heated under reflux in light radiation. After removal of insoluble materials by filtration, the filtrate was concentrated to dryness. The residue was purified by column chromatography on silica gel to afford a colorless syrup (2.7 g, 63%).

$^1$H-NMR(200 MHz,CDCl$_3$) δ: 4.49(2H,s), 6.39(1H,dd), 6.98–7.03(2H,m), 7.38–7.47(2H,m), 7.61(1H,d) IR(neat) cm$^{-1}$: 2200, 1500, 1440, 1400, 1320, 1170, 1060, 730

22e) Methyl 2-[N-[3-chloro-4-(2-cyanopyrrol-1-yl)phenyl]methyl-N-valeryl]amino-3-nitrobenzoate A solution of the compound obtained in Working Example 22d) (2.7 g), methyl 3-nitro-2- valerylaminobenzoate (2.0 g) and $K_2CO_3$ (1.4 g) in acetonitrile (35 ml) was heated under reflux for 24 hours. After addition of water, the reaction mixture was extracted with ethyl acetate. The extract was washed with water, dried and concentrated to dryness. The residue was purified by column chromatography on silica gel to give a pale brown syrup (2.5 g, 76%).

$^1$H-NMR(200 MHz,CDCl$_3$) δ: 0.85(3H,t), 1.17–1.36(2H,m), 1.59–1.75(2H,m), 2.08–2.16(2H,m), 3.76(3H,s), 4.70(1H,d), 4.85(1H,d), 6.36(1H,dd), 6.94–7.00(2H,m), 7.15(1H,dd), 7.27(1H,d), 7.36(1H,d), 7.65(1H,d), 8.00(1H,d), 8.14(1H,dd) IR(neat) cm$^{-1}$: 2200, 1730, 1670, 1600, 1535, 1505, 1450, 1390, 1350, 1290, 1260, 1210, 1130, 735, 700

22f) Methyl 2-butyl-1-[[3-chloro-4-(2-cyanopyrrol-1-yl)phenyl]methyl]benzimidazole-7-carboxylate A solution of the compound obtained in Working Example 22e) (2.5 g), iron powders (0.88 g) and conc. hydrochloric acid (2.7 ml) in methanol (30 ml) was heated under reflux for 66 hours. After removal of insoluble materials by filtration, the filtrate was concentrated to dryness. After addition of water, the mixture was extracted with ethyl acetate. The extract was washed with water, dried and evaporated. The residue was purified by column chromatography on silica gel to give crude crystals. Recrystallization from ethyl acetate-hexane afforded colorless needles (1.6 g, 70%), m.p. 115°–116° C.

$^1$H-NMR(200 MHz,CDCl$_3$) δ: 0.97(3H,t), 1.39–1.58(2H,m), 1.82–1.97(2H,m), 2.90(2H,t), 3.77(3H,s), 5.83(2H,s), 6.35(1H,dd), 6.81(1H,dd), 6.91(1H,dd), 6.97(1H,dd), 7.16(1H,d), 7.24–7.32(2H,m), 7.71(1H,dd), 7.97(1H,dd)

22g) Methyl 2-butyl-1-[[3-chloro-4-[2-(1H-tetrazol-5-yl)pyrrol-1-yl]phenyl]methyl]benzimidazole-7-carboxylate A solution of the compound obtained in Working Example 22f) (1.6 g) and trimethylsilyl azide (2.2 g) in toluene (25 ml) was heated under reflux for 21 hours. After removal of the solvent by evaporation, the residue was dissolved in methanol (30 ml) and 1N hydrochloric acid and the mixture was stirred at room temperature for 50 minutes. The reaction mixture was concentrated to dryness and the residue was extracted with ethyl acetate. The extract was washed with water, dried and evaporated. The residue was purified by column chromatography on silica gel to give crude crystals. Recrystallization from methanol-ethyl acetate afforded colorless prisms (1.4 g, 78%), m.p. 188°–190° C. (decomp.).

| Elemental Analysis for $C_{25}H_{24}ClN_7O_2$: | | | |
|---|---|---|---|
| | C (%) | H (%) | N (%) |
| Calcd.: | 61.29; | 4.94; | 20.01 |
| Found: | 61.15; | 5.09; | 19.61 |

$^1$H-NMR(200 MHz,CDCl$_3$) δ: 0.90(3H,t), 1.34–1.52(2H,m), 1.75–1.91(2H,m), 2.91(2H,t), 3.82(3H,s), 5.78(2H,s), 6.43(1H,dd), 6.78(1H,dd), 6.89(1H,dd), 7.04(1H,dd), 7.10(1H,d), 7.22–7.31(2H,m), 7.70(1H,dd), 7.91(1H,d) IR(KBr) cm$^{-1}$: 1710, 1610, 1510, 1445, 1430, 1420, 1405, 1280, 1265, 1200, 1120, 1060, 1020, 940, 750, 740, 705

22h) 2-Butyl-1-[[3-chloro-4-[2-(1H-tetrazol-5-yl)pyrrol-1-yl]phenyl]methyl]benzimidazole-7-carboxylic acid A solution of the compound obtained in Working Example 22g) (0.86 g) in a mixture of methanol (10 ml) and 1N aqueous NaOH (5.4 ml) was heated under reflux for 3.5 hours. After evaporation of methanol, the residue was neutralized with 1N aqueous hydrochloric acid (5.4 ml) to precipitate crystals. Recrystallization from chloroform-methanol afforded colorless prisms (0.71 g, 83%), m.p. 271°–272° C. (decomp.).

| Elemental Analysis for $C_{24}H_{22}ClN_7O_2$: | | | |
|---|---|---|---|
| | C (%) | H (%) | N (%) |
| Calcd.: | 60.34; | 4.68; | 20.53 |
| Found: | 60.29; | 4.65; | 20.28 |

$^1$H-NMR(200 MHz,DMSO-d$_6$) δ: 0.89(3H,t), 1.31–1.49(2H,m), 1.69–1.84(2H,m), 2.88(2H,t), 5.96(2H,s), 6.44(1H,t), 6.79(1H,dd), 6.98(1H,m), 7.09(1H,m), 7.21(1H,d), 7.28(1H,t), 7.41(1H,d), 7.68(1H,d), 7.87(1H,d) IR(KBr) cm$^{-1}$: 1635, 1600, 1500, 1410, 1375, 1340, 1310, 1280, 1120, 1080, 1010, 940, 880, 865, 755, 740, 715

Working Example 23

2-Butyl-1-[p-[4-(1H-tetrazol-5-yl)pyrimidin-5-yl]benzyl]benzimidazole-7-carboxylic acid 23a) 4-Amino-5-(p-tolyl)pyrimidine A mixture of p-methylbenzylcyanide (25 g, 0.19 mmol) and formamide (34.5 g, 0.76 mmol) was heated under reflux for 14 hours while removing produced water. After the reaction mixture was allowed to cool, precipitated crystals were collected by filtration and washed succesively with ether and water to afford yellow powders (9.35 g, 26%), m.p. 166°–167° C.

$^1$H-NMR(200 MHz) δ:2.42(3H,s), 5.12(2H,brs), 7.31(4H,s), 8.16, 8.55(each 1H,s)

Ref. J. Chem. Soc. 347, 1945

23b) 4-Hydroxy-5-(p-tolyl)pyrimidine

A mixture of 4-amino-5-(p-tolyl)pyrimidine (9.3 g, 50.3 mmol) in conc. hydrochloric acid (30 ml) was heated under reflux for 12 hours. After cooling, precipitates were collected by filtration and washed with water to afford white powders (9.05 g, 97%), m.p. 189°–192° C.

$^1$H-NMR(200 MHz) δ: 2.34(3H,s), 7.25, 7.62(each 2H,d), 8.20, 8.65(each 1H,s)

23c) 4-Chloro-5-(p-tolyl)pyrimidine

A mixture of 4-hydroxy-5-(p-tolyl)pyrimidine (9 g, 48 mmol) and phosphorous oxychloride (44 ml) was heated under reflux for 2 hours. After the reaction mixture was concentrated to dryness, the residue was poured into iced water to precipitate crystals which were extraced with methylene chloride. The extract was washed with water, dried and concentrated to dryness. The residue was purified by column chromatography on silica gel to afford colorless powders (7 g, 71%), m.p. 67°–70° C.

$^1$H-NMR(200 MHz) δ: 2.44(3H,s), 7.32, 7.38(each 2H,d), 8.66, 8.97(each 1H,s)

23d) 4-Cyano-5-(p-tolyl)pyrimidine

A mixture of 4-chloro-5-(p-tolyl)pyrimidine (7.4 g, 36 mmol), potassium cyanide (4.74 g, 72 mmol) and 18-crown-6 ether (0.48 g, 2 mmol) in acetonitrile (130 ml) was heated under reflux for 17 hours. After removal of insoluble materials by filtration from the reaction mixture, the filtrate was concentrated to dryness. The residue was purified by column chromatography on silica gel to give crystals. Recrystallization from ethyl acetate-hexane afforded pale yellow needles (4.17 g, 59%), m.p. 107°–109° C.

$^1$H-NMR(200 MHz) δ: 2.66(3H,s), 7.40, 7.51(each 2H,d), 9.02, 9.30(each 1H,s)

23e) 4-Cyano-5-(p-bromomethylphenyl)pyrimidine

A solution of 4-cyano-5-(p-tolyl)pyrimidine (1.2 g, 6 mmol), N-bromosuccinimide (1.15 g, 6 mmol) and benzoyl peroxide (catalytic amount) in carbon tetrachloride (50 ml) was refluxed under light radiation for 1 hour. After cooling, insoluble materials were removed and the filtrate was concentrated to dryness. Recrystallization from ether-isopropyl ether afforded colorless powders (1 g, 59%), m.p. 114°–116° C.

$^1$H-NMR(200 MHz) δ: 4.56(2H,s), 7.62(4H,s), 9.03, 9.34(each 1H,s)

23f) Methyl 3-nitro-2-[N-vareloyl-N-[p-(4-cyanopyrimidin-5-yl)benzyl]]aminobenzoate A solution of 4-cyano-5-(p-bromomethylphenyl)pyrimidine (1 g, 4 mmol), methyl 3-nitro-2-vareloylaminobenzoate (0.93 g, 3 mmol) and $K_2CO_3$ (0.55 g, 4 mmol) in DMF (15 ml) was stirred at room temperature for 36 hours. After the reaction mixture was concentrated to dryness, the residue was dissolved in methylene chloride. After removal of insoluble materials by filtration, the filtrate was concentrated to dryness. The residue was purified by column chromatography on silica gel to afford a yellow syrup (1.4 g, 89%).

$^1$H-NMR(200 MHz) δ: 0.86(3H,t), 1.19–1.37(2H,m), 1.60–1.76(2H,m), 2.07–2.17(2H,m), 3.73(3H,s), 4.83(2H,dd), 7.32, 7.46(each 2H,d), 7.63(1H,t), 7.98, 8.14(each 1H,dd), 9.00, 9.31(each 1H,s)

23 g) Methyl 2-butyl-1-[p-(4-cyanopyrimidin-5-yl)benzyl]benzimidazole-7-carboxylate To a solution of methyl 3-nitro-2-[N-valeryl-N-[p-(4-cyanopyrimidin-5-yl)benzyl]]aminobenzoate (1.4 g, 3 mmol) in methanol (15 ml) was added conc. hydrochloric acid (2.1 ml) followed by portionwise addition of iron powders (0.77 g, 13 mmol) and the mixture was heated under reflux for 17 hours. After the mixture was concentrated to dryness, the residue was dissolved in a mixture of 1,2-dichloroethane and 1N aqueous sodium hydroxide. After insoluble materials were filtered off through a pad of Celite, the filtrate was extracted with methylene chloride. The extract was washed with water and concentrated to dryness. The residue was purified by column chromatography on silica gel to afford colorless powders (0.18 g, 14%), m.p. 148°–149° C.

$^1$H-NMR(200 MHz,CDCl$_3$) δ: 0.96(3H,t), 1.40–1.58(2H,m), 1.82–1.97(2H,m), 2.91(2H,t), 3.73(3H,s), 5.88(2H,s), 7.07, 7.50(each 2H,d), 7.27(1H,t), 7.69, 7.97(each 1H,dd), 8.96, 9.30(each 1H,s)

23h) Methyl 2-butyl-1-[p-[4-(1H-tetrazol-5-yl)pyrimidin-5-yl]benzyl]benzimidazole-7-carboxylate A solution of methyl 2-butyl-1-[p-(4-cyanopyrimidin-5-yl)benzyl]benzimidazole-7-carboxylate (0.18 g, 0.4 mmol) and trimethyltin azide (0.27 g, 1.3 mmol) in toluene (5 ml) was heated under reflux for 28 hours. After removal of the solvent by evaporation, the residue was purified by column chromatography on silica gel. Recrystallization from ethyl acetate-isopropyl ether afforded colorless powders (40 mg, 20%), m.p. 215°–220° C.

$^1$H-NMR(200 MHz,CDCl$_3$) δ: 0.90(3H,t), 1.31–1.50(2H,m), 1.70–1.86(2H,m), 2.90(2H,t), 3.65(3H,s), 5.68(2H,s), 6.75, 7.15(each 2H,d), 7.24(1H,t), 7.51, 7.86(each 1H,d), 8.67, 9.15(each 1H,s)

23i) 2-Butyl-1-[p-[4-(1H-tetrazol-5-yl)pyrimidin-5-yl]benzyl]benzimidazole-7-carboxylic acid To a solution of methyl 2-butyl-1-[p-[4-(1H-tetrazol-5-yl)pyrimidin-5-yl]benzyl]benzimidazole-7-carboxylate (0.1 g, 0.2 mmol) in methanol (5 ml) was added 1N aqueous NaOH (0.5 ml) and the mixture was heated under reflux for 6 hours. After concentration to dryness, the residue was dissolved in water and the solution was neutralized with 1N aqueous hydrochloric acid. The resulting precipitate was collected by filtration and washed with water. Recrystallization from aqueous methanol afforded yellow powders (80 mg, 82%), m.p. 209°–212° C.

$^1$H-NMR(200 MHz,DMSO-d$_6$) δ: 0.89(3H,t), 1.31–1.48(2H,m), 1.68–1.84(2H,m), 2.88(2H,t), 5.93(2H,s), 6.90(2H,d), 7.21–7.34(3H,m), 7.64, 7.86(each 1H,d), 8.95, 9.39(each 1H,s)

| Elemental Analysis for $C_{24}H_{22}N_8O_2 \cdot H_2O \cdot \frac{1}{2}CH_3OH$: | | |
|---|---|---|
| C (%) | H (%) | N (%) |
| Calcd.: 60.24; | 5.36; | 22.94 |
| Found: 60.11; | 5.22; | 22.74 |

Working Example 24

2-Butyl-1-[4-[5-(1H-tetrazol-5-yl)pyrimidin-2-yl]benzyl]1H-benzimidazole-7-carboxylic acid 24a) 5-Bromo-4-(p-tolyl)pyrimidine To a solution of 5-bromopyrimidine (15.9 g, 0.1 mmol) in ether (200 ml) was added a Grignard reagent (prepared from p-tolyl bromide (20.52 g, 0.12 mmol), magnesium (2.92 g, 0.1 mmol) and ether (100 ml) dropwise at room temperature during 10 minutes. After the addition, the resulting suspension was heated under reflux for 1 hour and allowed to stand overnight. The reaction mixture was treated with aqueous ammonium chloride and then the ether layers were collected. The aqueous layers were extracted with methylene chloride and the extracts were combined with the ether layers and concentrated to dryness. The residue was purified by column chromatography on silica gel and then dissolved in acetone (100 ml). To the acetone solution was added a solution of potassium permanganate in acetone until red color disappeared, manganese dioxide was removed from the reaction mixture by filtration. The filtrate was concentrated to dryness and the residue was purified by column chromatography on silica gel. Recrystallization from hexane afforded colorless needles (12.8 g, 51%), m.p. 81°–82° C.

$^1$H-NMR(200 MHz,CDCl$_3$) δ: 2.44(3H,s), 7.32, 7.75(2H,d), 8.91, 9.15(1H,s)

24b) 5-Cyano-4-(p-tolyl)pyrimidine

A mixture of 5-bromo-4-(p-tolyl)pyrimidine (10 g, 40.2 mmol) and cuprous cyanide (4.4 g, 44.2 mmol) in DMF (20 ml) was heated under reflux for 3 hours. To the reaction mixture was added a solution of ferric chloride. 6 hydrate (13 g, 48.2 mmol) in a mixture of hydrochloric acid (7 ml) and water (55 ml) and the mixture was heated at 50° C. for 10 minutes. After the reaction solution was taken up in ethyl acetate and water, the mixture was extracted with ethyl acetate. The extract was washed with water and concentrated to dryness. The residue was purified by column chromatography on silica gel to give a crystalline product. Recrystallization from isopropyl ether-hexane afforded colorless needles (5 g, 64%), m.p. 127°–128° C.

¹H-NMR(200 MHz,CDCl₃) δ: 2.47(3H,s), 7.39, 8.06(2H,d), 9.03, 9.37(1H,s) IR(Nujol) cm⁻¹: 2225

24c) 4-(4-Bromomethylphenyl)-5-cyanopyrimidine

A mixture of 5-cyano-4-(p-tolyl)pyrimidine (2.5 g, 12.8 mmol), N-bromosuccinimide (2.4 g, 13.5 mmol) and benzoyl peroxide (catalytic amount) in carbon tetrachloride (100 ml) was refluxed under light radiation for 1 hour. After cooling, insoluble materials were removed and the filtrate was concentrated to dryness to afford a yellow syrup (3.7 g, 100%).

¹H-NMR(200 MHz,CDCl₃) δ: 4.55(2H,s), 7.61(2H,d), 8.13(2H,d), 9.07(1H,s), 9.40(1H,s)

24d) Methyl 2-[N-vareloyl-N-[4-(5-cyanopyrimidin-4-yl)benzyl]]amino-3-nitrobenzoate A solution of methyl 3-nitro-2-vareloylaminobenzoate (2.8 g, 10 mmol), 4-(4-bromomethylphenyl)-5-cyanopyrimidine (3.7 g, 12.8 mmol) and K₂CO₃ (1.77 g, 12.8 mmol) in DMF (50 ml) was stirred at room temperature for 19 hours. After the reaction mixture was concentrated to dryness, the residue was dissolved in methylene chloride. After removal of insoluble materials, the filtrate was concentrated to dryness. The residue was purified by column chromatography on silica gel to afford an orange syrup (2.9 g, 48%).

¹H-NMR(200 MHz,CDCl₃) δ: 0.85(3H,t), 1.19-1.36(2H,m), 1.60-1.76(2H,m), 2.08-2.17(2H,m), 3.67(3H,s), 4.70(1H,d), 4.96(1H,d), 7.29-7.34(2H,m), 7.62(1H,t), 7.95-8.01(2H,m), 8.09(1H,dd), 9.04(1H,s), 9.37(1H,s)

24e) Methyl 2-butyl-1-[4-(5-cyanopyrimidin-4-yl)benzyl]-1H-benzimidazole-7-carboxylate To a heated solution of methyl 2-[N-valeryl-N-[4-(5-cyanopyrimidin-4-yl)benzyl]amino-3-nitrobenzoate (0.5 g, 1.1 mmol), 5% Pd/C (5 mg) and triethylamine (0.46 g, 4.5 mmol) in acetonitrile (1 ml) was added formic acid (0.14 g, 3.5 mmol) dropwise under reflux and the mixture was heated under reflux for 22 hours. After the mixture was concentrated to dryness, the residue was dissolved in methylene chloride. After the catalyst was filtered off, the filtrate was concentrated to dryness and the residue was purified by column chromatography on silica gel to afford white powders (0.2 g, 45%), m.p. 131°-133° C.

¹H-NMR(200 MHz,CDCl₃) δ: 0.95(3H,t), 1.38-1.56(2H,m), 1.80-1.96(2H,m), 2.90(2H,t), 3.72(3H,s), 5.89(2H,s), 7.06(2H,d), 8.03(2H,d), 7.27(1H,t), 7.68(1H,dd), 7.98(1H,dd), 9.03(1H,s), 9.36(1H,s)

24f) Methyl 2-butyl-1-[4-[5-(1H-tetrazo-5-yl)pyrimidin-4-yl]benzyl]-1H-benzimidazole-7-carboxylate A solution of methyl 2-butyl-1-[4-(5-cyanopyrimidin-4-yl)benzyl]-1H-benzimidazole-7-carboxylate (0.53 g, 1.2 mmol) and trimethyltin azide (0.77 g, 3.7 mmol) in toluene (10 ml) was heated under reflux for 38 hours. After concentration to dryness, the residue was dissolved in methanol (10 ml). After addition of hydrochloric acid (0.6 ml), the mixture was stirred at room temperature for 1 hour and concentrated to dryness. The residue was purified by column chromatography on silica gel to afford pale yellow amorphous powders (0.53 g, 91%).

¹H-NMR(200 MHz,CDCl₃) δ: 0.89(3H,t), 1.30-1.49(2H,m), 1.69-1.82(2H,m), 2.97(2H,t), 3.61(3H,s), 5.76(2H,s), 6.91(2H,d), 7.31(2H,d), 7.37(1H,t), 7.61(1H,dd), 7.93(1H,dd), 9.09(1H,s), 9.41(1H,s)

24g) 2-Butyl-1-[4-[5-(1H-tetrazol-5-yl)pyrimidin-4-yl]benzyl]-1H-benzimidazole-7-carboxylic acid To a solution of methyl 2-butyl-1-[4-[5-(1H-tetrazol-5-yl)pyrimidin-4-yl]benzyl]-1H-benzimidazole-7-carboxylate (0.18 g, 0.4 mmol) in methanol (5 ml) was added 1N aqueous NaOH (0.9 ml) and the mixture was heated under reflux for 6 hours. After concentration to dryness, the residue was dissolved in water. After removal of insoluble materials by filtration, the filtrate was neutralized with aqueous hydrochloric acid. The resulting precipitates were collected by filtration to afford colorless powders (0.14 g, 77%), m.p. 181°-183° C.

| Elemental Analysis for $C_{24}H_{22}N_8O_2 \cdot H_2O$: | | |
| --- | --- | --- |
| C (%) | H (%) | N (%) |
| Calcd.: 60.90; | 5.09; | 22.51 |
| Found: 61.01; | 5.12; | 23.71 |

¹H-NMR(200 MHz,DMSO-d₆) δ: 0.87(3H,t), 1.28-1.45(2H,m), 1.66-1.80(2H,m), 2.84(2H,t), 5.89(2H,s), 6.87(2H,d), 7.30(2H,d), 7.26(1H,t), 7.63(1H,d), 7.85(1H,d), 9.07(1H,s) 9.40(1H,s)

Working Example 25

2-Butyl-1-[4-[3-(1H-tetrazol-5-yl)quinolin-4-yl]benzyl]benzimidazole-7-carboxylic acid 25a) 3-Cyano-4-(4-methylphenyl)quinoline A mixture of 2-amino-4'-methylbenzophenone (10 g), 3,3-dimethoxypropionitrile (10.9 g), p-toluenesulfonic acid. monohydrate (1.0 g) in toluene (120 ml) was heated under reflux for 4 hours. After addition of water, the reaction mixture was extracted with ethyl acetate and the extract was concentrated to dryness. The residue was purified by column chromatography on silica gel. Recrystallization from isopropyl ether afforded pale yellow prisms (5.67 g, 49%), m.p. 96°-97° C.

¹H-NMR(200 MHz,CDCl₃) δ: 2.49(3H,s), 7.40(4H,s), 7.54-7.64(1H,m), 7.81-7.92(2H,m), 8.20(1H,d), 9.08(1H,s)

25b) 3-Cyano-4-(4-bromomethyl)phenylquinoline

A solution of the compound obtained in Working Example 25a) (1.22 g), N-bromosuccinimide (1.0 g) and azobisisobutyronitrile (AIBN) (80 mg) in carbon tetrachloride (20 ml) was heated under stirring for 1.5 hours. After addition of water, the reaction mixture was extracted with methylene chloride and the extract was washed with water, dried and concentrated to dryness. The residue was purified by column chromatography on silica gel to afford crystals. Recrystallization from methylene chloride-ether afforded colorless prisms (1.41 g, 87%), m.p. 144°-145° C.

¹H-NMR(200 MHz,CDCl₃) δ: 4.61(2H,s), 7.50(2H,d), 7.55-7.96(3H,m), 8.24(1H,d), 9.11(1H,s)

25c) Methyl 2-[N-(4-cyanoquinolin-4-yl)benzyl-N-valeryl]amino-3-nitrobenzoate

A solution of the compound obtained in Working Example 25b) (0.66 g), methyl 3-nitro-2-valerylaminobenzoate (0.56 g), K₂CO₃ (0.42 g) and potassium iodide (50 mg) in DMF (10 ml) was stirred at 80° C. for 4 hours. After addition of water, the reaction mixture was extracted with ethyl acetate and the extract was washed with water, dried and evaporated. The residue was purified by column chromatography on silica gel to afford an oil (0.48 g, 46%).

¹H-NMR(200 MHz,CDCl₃) δ: 0.87(3H,t), 1.29(2H,m), 1.72(2H,m), 2.14(2H,m), 3.81(3H,s), 4.71(2H,d), 5.05(2H,d), 7.15-7.51(4H,m), 7.59-8.03(5H,m), 8.15-8.24(2H,m), 9.07(1H,s)

25d) Methyl 2-butyl-1-[4-(3-cyanoquinolin-4-yl)benzyl]-1H-benzimidazole-7-carboxylate To a stirred solution of the compound obtained in Working Example 25c) (2.3 g) in methanol (25 ml) containing conc. hydrochloric acid (1 ml) were added iron powders (1.23 g) and the mixture was heated under reflux for 2 hours. After insoluble materials were filtered off, the filtrate was diluted with water and extracted with chloroform. The extract was washed with water, dried and concentrated to dryness. The residue was purified by column chromatography on silica gel to afford crystals. Recrystallization from ether afforded colorless prisms (1.8 g, 86%), m.p. 103°–104° C.

$^1$H-NMR(200 MHz,CDCl$_3$) δ: 0.98(3H,t), 1.52(2H,m), 1.92(2H,m), 2.97(2H,t), 3.76(3H,s), 5.91(2H,s), 7.10(2H,d), 7.24–8.05(8H,m), 8.21(1H,d), 9.09(1H,s)

25e) Methyl 2-butyl-1-[4-[3-(1H-tetrazol-5-yl)quinolin-2-yl]benzyl]-1H-benzimidazole-7-carboxylate A solution of the compound obtained in Working Example 25d) (0.95 g) and trimethyltin azide (1.24 g) in toluene (20 ml) was heated under reflux for 2 days. To the reaction mixture was added 2N hydrochloric acid (8 ml) and methanol (10 ml) and the mixture was stirred at room temperature for 1 hour. After addition of water, the mixture was extracted with chloroform and the extract was washed with water, dried and concentrated to dryness. The residue was purified by column chromatography on silica gel to afford a syrup. Recrystallization from ethyl acetate afforded colorless prisms (0.61 g, 58%), m.p. 233°–234° C.

| Elemental Analysis for C$_{30}$H$_{27}$N$_7$O$_2$.0.5H$_2$O: | | |
|---|---|---|
| C (%) | H (%) | N (%) |
| Calcd.: 68.43; | 5.36; | 18.62 |
| Found: 68.61; | 5.24; | 18.45 |

$^1$H-NMR(200 MHz,DMSO-d$_6$) δ: 0.91(3H,t), 1.42(2H,m), 1.78(2H,m), 2.91(2H,t), 3.66(3H,s), 5.76(2H,s), 6.91(2H,d), 7.19(2H,d), 7.26(1H,t), 7.41–7.69(3H,m), 7.81–7.94(2H,m), 8.18(1H,d), 9.15(1H,s)

25f) 2-Butyl-1-[4-[3-(1H-tetrazol-5-yl)quinolin-4-yl]benzyl]-1H-benzimidazole-7-carboxylic acid To a solution of the compound obtained in Working Example 25e) (0.104 g), LiOH.H$_2$O (21 mg) and water (0.2 ml) in methanol (2 ml) was stirred at 80° C. for 3 hours. After evaporation of the solvent, the residue was diluted with 2N aqueous hydrochloric acid (0.4 ml). The resulting precipitate was collected by filtration. Recrystallization from aqueous methanol afforded colorless prisms (38 mg, 36%), m.p. 250°–251° C.

| Elemental Analysis for C$_{29}$H$_{25}$N$_7$O$_2$.H$_2$O: | | |
|---|---|---|
| C (%) | H (%) | N (%) |
| Calcd.: 66.78; | 5.22; | 18.80 |
| Found: 66.99; | 4.92; | 18.59 |

$^1$H-NMR(200 MHz,DMSO-d$_6$) δ: 0.90(3H,t), 1.39(2H,m), 1.75(2H,m), 2.88(2H,t), 5.92(2H,s), 6.95(2H,d), 7.19(2H,d), 7.24–7.95(6H,m), 8.18(1H,d), 9.14(1H,s) IR(Nujol) cm$^{-1}$: 1690, 1595

Working Example 26

2-Butyl-1-[[4-oxo-3-[2-(1H-tetrazol-5-yl)phenyl]-3,4-dihydroquinazolin-7-yl]methyl]benzimidazole-7-carboxylic acid 26a) 4-Methyl-2-nitrobenzoic acid A mixed solution of 2-nitro-4-methylbenzonitrile (15.8 g) in a mixture of 65% sulfuric acid and acetic acid (150 ml) was heated under reflux for 17 hours. After concentration, the residue was poured into ice-water and extracted with ethyl acetate. The extract was washed with water, dried and concentrated to dryness. Recrystallization of crystals from ether-hexane afforded colorless crystals (16.5 g, 94%), m.p. 156°–157° C.

$^1$H-NMR(200 MHz,DMSO-d$_6$) δ: 2.44(3H,s), 7.56–7.61(1H,m), 7.75–7.79(2H,m)

26b) N-(2-Cyanophenyl)-4-methyl-2-nitrobenzamide

To a stirred suspension of 4-methyl-2-nitrobenzoic acid (5 g) in THF (30 ml) was added dropwise a solution of oxalyl chloride (2.7 ml) in DMF (0.1 ml) and the mixture was stirred at room temperature for 17 hours and concentrated to dryness. To an ice-cooled, stirred solution of 2-aminobenzonitrile (3.26 g) and pyridine (2.5 ml) in methylene chloride (30 ml) was added dropwise a solution of the resulting acid chloride in methylene chloride (30 ml) and the mixture was stirred at room temperature for 4 hours and concentrated to dryness. The residue was extracted with a mixture of ethyl acetate-THF. The extract was washed with dilute hydrchloric acid and water, dried and evaporated. Recrystallization from ethyl acetate-ether afforded colorless needles (7.4 g, 95%), m.p. 230°–232° C.

$^1$H-NMR(200 MHz,DMSO-d$_6$) δ: 2.49(3H,s), 7.39–7.48(1H,m), 7.65–7.90(2H,m), 8.02(1H,s), 10.91(1H,s)

26c) 3-(2-Cyanophenyl)-7-methylquinazolin-4(3H)-one

A suspension of the compound obtained in Working Example 26b) (8.75 g) and 10% Pd/C (0.88 g) in a mixture of THF (450 ml)-methanol (150 ml) was stirred under H$_2$ atmosphere at room temperature for 2 hours. After removal of insoluble materials by filtration, the filtrate was concentrated to dryness. The resulting pale yellow solid was suspended with ethyl orthoformate (300 ml) and the mixture was heated under reflux for 5 hours followed by concentration to dryness. Recrystallization from ethyl acetate-hexane afforded colorless crystals (7.65 g, 94%), m.p. 223°–224° C.

$^1$H-NMR(200 MHz,CDCl$_3$) δ: 2.56(3H,s), 7.41(1H,d), 7.53–7.69(3H,m), 7.80–7.91(2H,m), 8.03(1H,s), 8.27(1H,d) IR(KBr) cm$^{-1}$: 2225, 1677, 1601

26d) 7-Bromomethyl-3-(2-cyanophenyl)quinazolin-4(3H)-one

A solution of the compound obtained in Working Example 26c) (2.62 g), N-bromosuccinimide (1.8 g) and benzoyl peroxide (40 mg) in carbon tetrachloride (700 ml) was heated under reflux in light radiation for 2 hours. After concentration to dryness, the residue was extracted with chloroform and the extract was washed with water, dried and evaporated. The residue was purified by column chromatography on silica gel to afford white powders (1.9 g, 56%), m.p. 220°–224° C. (decomp.).

$^1$H-NMR(200 MHz,CDCl$_3$) δ: 4.61(2H,s), 7.52–7.70(3H,m), 7.79–7.92(3H,m), 8.06(1H,s), 8.36(1H,d)

26e) 3-(2-Cyanophenyl)-7-[[N-methoxycarbonyl-6-nitrophenyl)-N-valeryl]aminomethyl]quinazolin-4(3H)-one A solution of the compound obtained in Working Example 26d) (1.23 g), methyl 3-nitro-2-valerylaminobenzoate (0.841 g), $K_2CO_3$ (0.63 g) and KI (50 mg) in acetonitrile (50 ml) was heated under reflux for 14 hours. In the substantially same manner as in Working Example 25c), the title compound was obtained as pale yellow powders (1.2 g, 74%).

$^1$H-NMR(200 MHz,CDCl$_3$) δ: 0.86(3H,t), 1.18–1.37(2H,m), 1.57–1.76(2H,m), 2.13(2H,t), 3.61(3H,s), 4.66(1H,d), 5.16(1H,d), 7.51–7.69(4H,m), 7.78–7.91(2H,m), 7.97–8.09(4H,m), 8.22–8.28(1H,m) IR(KBr) cm$^{-1}$: 2960, 2230, 1739, 1685, 1605, 1598, 1538

26f) Methyl 2-butyl-1-[[3-(2-cyanophenyl)-4-oxo-3,4-dihydroquinazolin-7-yl]methyl]benzimidazole-7-carboxylate In the substantially same manner as in Working Example 25d), the title compound was prepared as pale brown powders (0.86 g, 79%) from the compound obtained in Working Example 26e) (1.2 g).

$^1$H-NMR(200 MHz,CDCl$_3$) δ: 0.95(3H,t), 1.38–1.57(2H,m), 1.82–1.98(2H,m), 2.89(2H,t), 3.72(3H,s), 5.97(2H,s), 7.15–7.20(2H,m), 7.27(1H,t), 7.48–7.52(1H,m), 7.60–7.90(4H,m), 7.96–8.00(2H,m), 8.26–8.31(1H,m) IR(KBr) cm$^{-1}$: 2955, 2225, 1718, 1693, 1610, 1599, 1562, 1520

26g) Methyl 2-butyl-1-[[4-oxo-3-[2-(1H-tetrazol-5-yl)phenyl]-3,4-dihydroquinazolin-7-yl]methyl]benzimidazole-7-carboxylate In the substantially same manner as in Working Example 25e), the title compound was prepared as colorless crystals (0.48 g, 59%) from the compound obtained in Working Example 26f) (0.75 g).

| Elemental Analysis for $C_{29}H_{26}N_8O_3 \cdot 0.2H_2O$: | | |
|---|---|---|
| C (%) | H (%) | N (%) |
| Calcd.: 64.72; | 4.94; | 20.82 |
| Found: 64.59; | 4.83; | 20.90 |

$^1$H-NMR(200 MHz,DMSO-d$_6$) δ: 0.90(3H,t), 1.32–1.51(2H,m), 1.73–1.87(2H,m), 2.94(2H,t), 3.65(3H,s), 5.89(2H,s), 7.01–7.24(2H,m), 7.28(1H,t), 7.54–7.58(1H,m), 7.68–7.80(3H,m), 7.89–8.02(2H,m), 8.09–8.14(1H,m), 8.26(1H,s) IR(KBr) cm$^{-1}$: 3420, 2950, 2700–2200, 1720, 1687, 1618, 1600 1559, 1505

26h) 2-Butyl-1-[[4-oxo-3-[2-(1H-tetrazol-5-yl)phenyl]-3,4-dihydroquinazolin-7-yl]methyl]benzimidazole-7-carboxylic acid In the substantially same manner as in Working Example 25f), the title compound was prepared as white powders (0.27 g, from the compound obtained in Working Example 26g) (0.42 g), m.p. 250°–258° C. (decomp.).

| Elemental Analysis for $C_{28}H_{24}N_8O_3 \cdot 0.3C_4H_8O_2 \cdot 0.4H_2O$: | | |
|---|---|---|
| C (%) | H (%) | N (%) |
| Calcd.: 63.29; | 4.95; | 20.22 |
| Found: 63.15; | 4.94; | 20.45 |

$^1$H-NMR(200 MHz,DMSO-d$_6$) δ: 0.89(3H,t), 1.31–1.49(2H,m), 1.70–1.86(2H,m), 2.91(2H,t), 6.05(2H,s), 6.98(1H,d), 7.07–7.12(1H,m), 7.28(1H,t), 7.62–7.79(4H,m), 7.87–7.91(1H,m), 7.99(1H,d), 8.09–8.13(1H,m), 8.26(1H,s) IR(KBr) cm$^{-1}$: 3440, 2960, 2800–12200, 1695, 1620, 1561

Working Example 27

2-Butyl-1-[[5-methyl-2-(1H-tetrazol-5-yl)pyrrol-1-yl]phenyl]methyl]benzimidazole-7-carboxylic acid 27a) Methyl 4-(1-pyrrolyl)benzoate To a stirred solution of methyl 4-aminobenzoate (7.6 g) in acetic acid (25 ml) was added 2,5-dimethoxytetrahydrofuran (6.6 g) dropwise and the reaction mixture was heated under reflux for 1 hour and then diluted with water. The resulting precipitated crystals were purified by column chromatography on silica gel. Recrystallization from ethyl acetate-hexane afforded the title compound as colorless plates (7.5 g, 74%), m.p. 128°–129° C.

| Elemental Analysis for $C_{12}H_{11}NO_2$: | | |
|---|---|---|
| | C (%) | H (%) | N (%) |
| Calcd.: | 71.63; | 5.51; | 6.96 |
| Found: | 71.61; | 5.25; | 6.94 |

$^1$H-NMR(200 MHz,CDCl$_3$) δ: 3.93(3H,s), 6.38(2H,t), 7.16(2H,t), 7.45(2H,d), 8.10(2H,d) IR(KBr) cm$^{-1}$: 1720, 1600, 1520, 1465, 1430, 1330, 1280, 1180, 1100, 840, 760, 710

27b) Methyl 4-(2-formylpyrrol-1-yl)benzoate

Phosphorous oxychloride (6.3 g) was added dropwise to N,N-dimethylformamide (3.0 g) under ice-cooling and the reaction mixture was stirred at room temperature for 15 minutes. To the mixture was added dropwise a solution of the compound obtained in Working Example 27a) (7.5 g) in N,N-dimethylformamide (15 ml) and the mixture was stirred at 50°–60° C. for 1.5 hours. The reaction mixture was diluted with ice-water and made basic with potassium carbonate. The resulting crystals were collected by filtration. Recrystallization from ethyl acetate-hexane afforded the title compound as colorless pillars (2.9 g, 34%), m.p. 103°–105° C.

| Elemental Analysis for $C_{13}H_{11}NO_2$: | | |
|---|---|---|
| | C (%) | H (%) | N (%) |
| Calcd.: | 68.11; | 4.84; | 6.11 |
| Found: | 68.35; | 4.68; | 6.19 |

$^1$H-NMR(200 MHz,CDCl$_3$) δ: 3.95(3H,s), 6.45(1H,dd), 7.11(1H,m), 7.18(1H,d), 7.43(2H,d), 8.14(2H,d), 9.60(1H,s) IR(KBr) cm$^{-1}$: 1710, 1670, 1600, 1460, 1430, 1410, 1375, 1360, 1315, 1280, 1175, 1110, 1100, 860, 775, 755, 690

27c) 4-(2-formylpyrrol-1-yl)benzoic acid

To a solution of the compound obtained in Working Example 27b) (2.6 g) in methanol (50 ml) was added 1N aqueous NaOH (15 ml) and the mixture was stirred at room temperature for 5.5 hours. After evaporation of methanol, the residue was neutralized with 1N aqueous hydrochloric acid. The resulting precipitates were collected by filtration. Recrystallization from chloroform-methanol afforded the title compound as colorless flakes (2.4 g, 100%), m.p. 269°–270° C.

| Elemental Analysis for $C_{12}H_9NO_3$: | | |
|---|---|---|
| | C (%) | H (%) | N (%) |
| Calcd.: | 66.97; | 4.22; | 6.51 |

| | | | |
|---|---|---|---|
| Found: | 66.87; | 4.07; | 6.51 |

$^1$H-NMR(200 MHz,CDCl$_3$) δ: 6.51(1H,dd), 7.29(1H,dd), 7.51-7.58(3H,m), 8.04(2H,m), 9.56(1H,s) IR(KBr) cm$^{-1}$: 1660, 1600, 1460, 1430, 1420, 1380, 1360, 1320, 1295, 865, 780, 760

27d) Methyl 4-(2-methylpyrrol-1-yl)benzoate

To a mixture of anhydrous hydrazine (2.1 g) and potassium tert-butoxide (7.2 g) in toluene (120 ml) was added the compound obtained in Working Example 27c) (2.3 g) and the mixture was heated under reflux for 16 hours. After addition of water, the aqueous layers were separated and acidified with conc. hydrochloric acid. The precipitated crystals were separated by filtration and dissolved in N,N-dimethylformamide (10 ml). To the solution was added methyl iodide (1.7 g) and potassium carbonate (1.7 g) and the mixture was stirred at room temperature for 3.5 hours. The reaction mixture was diluted with water and extracted with ethyl acetate. The extract was washed with water, dried and concentrated to dryness. The residue was purified by column chromatography on silica gel to afford a colorless oil (1.4 g, 58%).

$^1$H-NMR(200 MHz,CDCl$_3$) δ: 2.26(3H,s), 3.95(3H,s), 6.08(1H,m), 6.23(1H,t), 6.80(1H,dd), 7.38(2H,m), 8.12(2H,d) IR(neat) cm$^{-1}$: 1725, 1600, 1330, 1275, 1175, 1110, 775, 700

27e) Methyl 4-(2-cyano-5-methylpyrrol-1-yl)benzoate

To a solution of the compound obtained in Working Example 27d) (1.8 g) in a mixture of acetonitrile (6.5 ml) and N,N-dimethylformamide (10 ml) was added a solution of chlorosulfonyl isocyanate (1.8 g) in acetonitrile (9.0 ml) dropwise at −78° C. and the mixture was stirred at the same temperature for 1.5 hours. After elevation to room temperature, the reaction mixture was diluted with ice-water, extracted with ethyl acetate and the extract was washed with water, dried and concentrated to dryness. The residue was purified by column chromatography on silica gel to afford crude crystals. Recrystallization from isopropyl ether afforded colorless crystals (1.1 g, 69%), m.p. 118 -119° C.

| Elemental Analysis for C$_{14}$H$_{12}$N$_2$O$_2$: | | | |
|---|---|---|---|
| | C (%) | H (%) | N (%) |
| Calcd.: | 69.99; | 5.03; | 11.66 |
| Found: | 70.12; | 5.18; | 11.61 |

$^1$H-NMR(200 MHz,CDCl$_3$) δ: 2.18(3H,s), 3.98(3H,s), 6.11(1H,d), 6.91(1H,d), 7.41(2H,d), 8.21(2H,d) IR(KBr) cm$^{-1}$: 220, 1720, 1600, 1500, 1465, 1425, 1400, 1320 1290, 1275, 1210, 1105, 855, 790, 770, 700

27f) 4-(2-Cyano-5-methylpyrrol-1-yl)benzyl alcohol

To a suspension of the compound obtained in Working Example 27e) (1.1 g) and sodium borohydride (0.46 g) in THF (20 ml) was added methanol (3.6 ml) dropwise over 30 minutes and the mixture was refluxed for 20 hours, diluted with water and extracted with ethyl acetate. The extract was washed with water, dried and concentrated to dryness. The residue was purified by column chromatography on silica gel to afford a colorless oil (1.0 g, 100%).

$^1$H-NMR(200 MHz,CDCl$_3$) δ: 2.15(3H,s), 4.78(2H,s), 6.07(1H,m), 6.87(1H,d), 7.30(2H,d), 7.52(2H,d) IR(neat) cm$^{-1}$: 3400, 2200, 1510, 1475, 1405, 1320, 1200, 1040, 820, 765

27g) Methyl 3-nitro-2-[N-[4-(2-cyano-5-methylpyrrol-1-yl)phenyl]methyl-N-valeryl]aminobenzoate To a solution of the compound obtained in Working Example 27f) (0.42 g) in chloroform (10 ml) was added N,N-dimethylaniline (0.36 g) and methanesulfonyl chloride (0.50 g). The mixture was refluxed for 4.5 hours, washed with aqueous sodium bicarbonate and dried. After removal of the solvent by evaporation, the residue was purified by column chromatography on silica gel to afford a colorless oil. The oil was dissolved in acetonitrile (10 ml) followed by addition of methyl 3-nitro-2-valerylaminobenzoate (0.56 g), potassium carbonate (0.28 g) and potassium iodide (0.33 g) and the mixture was heated under reflux for 60 hours. After dilution of water and extraction with ethyl acetate, the extract was washed with water, dried and evaporated in vacuo. The residue was purified by column chromatography on silica gel to afford a brown oil (0.47 g, 49%).

$^1$H-NMR(200 MHz,CDCl$_3$) δ: 0.85(3H,t), 1.18-1.36(2H,m), 1.59-1.75(2H,m), 2.11(2H,m), 2.16(3H,s), 3.76(3H,s), 4.69(1H,d), 4.93(1H,d), 6.06(1H,d), 6.85(1H,d), 7.14(2H,d), 7.24(2H,d), 7.61(1H,t), 7.95(1H,dd), 8.14(1H,dd) IR(neat) cm$^{-1}$: 2200, 1730, 1670, 1530, 1520, 1470, 1445, 1405, 1350, 1285, 1260, 1200, 1125, 770, 700

24e) Methyl 2-butyl-1-[[4-(2-cyano-5-methylpyrrol-1-yl)phenyl]methyl]benzimidazole-7-carboxylate To a solution of the compound obtained in Working Example 27g) (0.47 g) in methanol (10 ml) was added conc. hydrochloric acid (2.1 ml) and iron powders (0.72 g) and the mixture was heated under reflux for 24 hours. After insoluble materials were filtered off, the filtrate was concentrated in vacuo to dryness. The resulting residue was diluted with 6N aqueous NaOH and the mixture was extracted with ethyl acetate. The extract was washed with water, dried and concentrated to dryness. The residue was purified by column chromatography on silica gel to afford crude crystals. Recrystallization from ethyl acetate-hexane afforded a colorless crystals (0.24 g, 56%), m.p. 131°-132° C.

| Elemental Analysis for C$_{26}$H$_{26}$N$_4$O$_2$: | | | |
|---|---|---|---|
| | C (%) | H (%) | N (%) |
| Calcd.: | 73.22; | 6.14; | 13.14 |
| Found: | 73.10; | 6.01; | 13.09 |

$^1$H-NMR(200 MHz,CDCl$_3$) δ: 0.96(3H,t), 1.38-1.57(2H,m), 1.81-1.96(2H,m), 2.09(3H,s), 2.92(2H,t), 3.70(3H,s), 5.84(2H,s), 6.05(1H,d), 6.85(1H,d), 6.99(2H,d), 7.18-7.31(3H,m), 7.65(1H,dd), 7.96(1H,dd) IR(KBr) cm$^{-1}$: 2200, 1720, 1515, 1475, 1410, 1330, 1280, 1260, 1200, 1120, 1110, 780, 750, 745

27i) Methyl 2-butyl-1-[4-[2-methyl-5-(1H-tetrazol-5-yl)pyrrol-1-yl]phenyl]methyl]benzimidazole-7-carboxylate To a solution of the compound obtained in Working Example 27h) (0.23 g) in toluene (10 ml) was added trimethyltin azide (0.33 g) and the mixture was refluxed for 43 hours. After removal of the solvent by evaporation, the residue was dissolved in methanol (10 ml). After addition of 1N hydrochloric acid (2 ml), the mixture was stirred at room temperature for 30 minutes. After removal of the solvent by evaporation, the residue was diluted with water and the mixture was extracted with ethyl acetate. The extract was washed with water, dried and concentrated to dryness. The residue was purified by column chromatography on silica gel to afford crude crystals. Recrystallization from ethyl acetate-methanol afforded brown crystals (0.11 g, 42%), m.p. 198°–199° C.

Elemental Analysis for C₂₆H₂₇N₇O₂.0.1AcOEt:

| | C (%) | H (%) | N (%) |
|---|---|---|---|
| Calcd.: | 66.29; | 5.86; | 20.50 |
| Found: | 66.13; | 5.82; | 20.24 |

¹H-NMR(200 MHz,CDCl₃) δ: 0.93(3H,t), 1.37–1.55(2H,m), 1.76–1.92(2H,m), 2.09(3H,s), 2.91(2H,t), 3.75(3H,s), 5.75(2H,s), 6.18(1H,d), 6.91(1H,d), 7.04(1H,d), 7.12(2H,d), 7.25(1H,t), 7.63(1H,d), 7.82(1H,d) IR(KBr) cm⁻¹: 1720, 1600, 1515, 1430, 1410, 1350, 1285, 1265, 1215, 1125, 1030, 920, 770, 755, 740

27j) 2-Butyl-1-[4-[2-methyl-5-(1H-tetrazol-5-yl)pyrrol-1-yl]phenyl]methyl]benzimidazole-7-carboxylic acid To a solution of the compound obtained in Working Example 27i) (70 mg) in methanol (1 ml) was added 1N aqueous NaOH (0.5 ml) and the mixture was heated under reflux for 20 hours. After dilution with water, the solution was adjusted with 1N aqueous HCl to pH 3–4. The resulting precipitates were collected by filtration. Recrystallization from ethyl acetate-methanol afforded brown crystals (34 mg, 49%), m.p. 258°–259° C.

Elemental Analysis for C₂₅H₂₅N₇O₂.0.2H₂O:

| | C (%) | H (%) | N (%) |
|---|---|---|---|
| Calcd.: | 65.40; | 5.58; | 21.36 |
| Found: | 65.21; | 5.60; | 21.52 |

¹H-NMR(200 MHz,DMSO-d₆) δ: 0.86(3H,t), 1.27–1.46(2H,m), 1.65–1.80(2H,m), 1.96(3H,s), 2.87(2H,t), 5.92(2H,s), 6.16(1H,d), 6.80(1H,d), 6.94(2H,d), 7.16(2H,d), 7.25(1H,t), 7.61(1H,dd), 7.84(1H,dd) IR(KBr) cm⁻¹: 1600, 1575, 1515, 1425, 1375, 1355, 1210, 1070, 1040, 920, 840, 760, 740

Working Example 28

2-Butyl-1-[[3-methyl-4-oxo-2-[2-(1H-tetrazol-5-yl)phenyl]3,4-dihydroquinazolin-6-yl]methyl]benzimidazole-7-carboxylic acid 28a) 2-Amino-5-methylbenzamide To a stirred solution of 5-methyl-2-nitrobenzoic acid (25.4 g) in THF (150 ml) was added oxalyl chloride (13.5 ml) and DMF (0.1 ml) dropwise and the mixture was stirred at room temperature for 14 hours and concentrated to dryness. To an ice-cooled, stirred 25% aqueous solution of ammonia (150 ml) was added the resulting acid chloride dropwise and the mixture was stirred at the same temperature for 1 hour. The white precipitates were collected by filtration, washed with water, and dried in vacuo. A suspension of the white precipitates and 10% Pd/C (2.4 g) in a mixture of THF (200 ml) and methanol (150 ml) was stirred under hydrogen atmosphere at room temperature for 4 hours. After removal of insoluble materials by filtration, the filtrate was concentrated to dryness. Recrystallization of the resultant crystalline residue from ethyl acetate-hexane afforded colorless crystals (18.7 g, 89%), m.p. 178°–180° C.

Elemental Analysis for C₈H₁₀N₂O.0.1H₂O:

| | C (%) | H (%) | N (%) |
|---|---|---|---|
| Calcd.: | 63.22; | 6.76; | 18.43 |
| Found: | 63.49; | 6.77; | 18.41 |

¹H-NMR(200 MHz,DMSO-d₆) δ: 2.15(3H,s), 6.30(2H,brs), 6.58(1H,d), 6.95(1H,dd), 6.97(1H,br), 7.34(1H,d), 7.64(1H,br) IR(KBr) cm⁻¹: 3380, 3200, 1645, 1580, 1552

28b) 2-(2-Bromobenzamide)-5-methylbenzamide

To a stirred solution of 2-bromobenzoic acid (6.81 g) in THF (70 ml) was added oxalyl chloride (3.3 ml) and DMF (2 drops) dropwise and the mixture was stirred at room temperature for 16 hours and concentrated to dryness to give an acid chloride. To an ice-cooled, stirred solution of the compound obtained in Working Example 28a) (3.91 g), 4-dimethylaminopyridine (0.26 g) and pyridine (4.2 ml) in DMF (15 ml) was added a solution of the resulting acid chloride in DMF (10 ml) dropwise and the mixture was stirred at the same temperature for 1 hour. After removal of the solvent by evaporation, the residue was extracted with ethyl acetate and THF. The extract was washed with dilute hydrochloric acid, aqueous sodium bicarbonate and water, dried and concentrated to dryness. Recrystallization of the crystalline residue from ethyl acetate-ether afforded colorless plates (7.37 g, 85%), m.p. 221.5°–222.5° C.

Elemental Analysis for C₁₅H₁₃N₂O₂Br:

| | C (%) | H (%) | N (%) |
|---|---|---|---|
| Calcd.: | 54.07; | 3.93; | 8.41 |
| Found: | 54.05; | 4.10; | 8.37 |

¹H-NMR(200 MHz,DMSO-d₆) δ: 2.33(3H,s), 7.36–7.75(7H,m), 8.28(1H,brs), 8.48(1H,d), 12.08(1H,brs) IR(KBr) cm⁻¹: 3375, 3205, 3140, 1660, 1622, 1590, 1517

28c) 2-(2-bromophenyl)-6-methylquinazolin-4(3H)-one

A mixture of the compound (7.48 g) obtained in Working Example 28b) in a mixture of pyridine (5 ml) and 2N aqueous sodium hydroxide (135 ml) was heated under reflux for 30 minutes. After cooling, the reaction mixture was diluted with 2N aqueous hydrochloric acid (150 ml) under ice-cooling and the resulting crude crystals were collected by filtration, washed with water, and dried in vacuo. Recrystallization from aqueous methanol afforded colorless crystals (6.74 g, 95%), m.p. 205°–206° C.

Elemental Analysis for C₁₅H₁₁N₂OBr:

| | C (%) | H (%) | N (%) |
|---|---|---|---|
| Calcd.: | 57.16; | 3.52; | 8.89 |
| Found: | 57.40; | 3.58; | 8.93 |

¹H-NMR(200 MHz,DMSO-d₆) δ: 2.48(3H,s), 7.42–7.79(6H,m), 7.97(1H,s), 12.50(1H,brs) IR(KBr) cm⁻¹: 3010, 2860, 1660, 1620, 1602, 1485

28d) 2-(2-Bromophenyl)-3,6-dimethylquinazolin-4(3H)-one

To an ice-cooled solution of the compound obtained in Working Example 28c) (6.0 g) in DMF (50 ml) under N₂ was added sodium hydride (60% dispersion in mineral oil, 0.765 g) and the mixture was stirred at the same temperature for 30 minutes followed by addition of methyl iodide (2.4 ml). The resulting mixture was stirred at room temperature for 2 hours. After removal of the solvent, the residue was extracted with ethyl acetate and the extract was washed with water, dried and concentrated to dryness. The residue was purified by column chromatography on silica gel to afford white powders (5.6 g, 89%).

$^1$H-NMR(200 MHz,CDCl$_3$) δ: 2.53(3H,s), 3.40(3H,s), 7.27–7.73(6H,m), 8.16(1H,s) IR(KBr) cm$^{-1}$: 1678, 1590, 1582, 1560, 1489

28e) 2-(2-Cyanophenyl)-3,6-dimethylquinazolin-4(3H)-one

To a solution of the compound (5.97 g) obtained in Working Example 28d) in DMF (60 ml) was added cuprous cyanide (2.17 g) and the reaction mixture was stirred at 120°–130° C. for 6 hours. After cooling, the mixture was treated with an aqueous solution (60 ml) of ferric chloride (8.84 g) and 1N aqueous hydrochloric acid (28 ml). The reaction mixture was stirred at 50° C. for 20 minutes and then partitioned between ethyl acetate and water. The aqueous phase was extracted with ethyl acetate. The organic phases were combined, washed with water, dried and the solvent was evaporated in vacuo. The residue was purified by column chromatography on silica gel to give cryatals. Recrystallization from ethyl acetate-hexane afforded colorless needles (4.03 g, 81%), m.p. 157°–158° C.

| Elemental Analysis for C$_{17}$H$_{13}$N$_3$O: | | | |
|---|---|---|---|
| | C (%) | H (%) | N (%) |
| Calcd.: | 74.17; | 4.76; | 15.26 |
| Found: | 74.39; | 4.77; | 15.45 |

$^1$H-NMR(200 MHz,CDCl$_3$) δ: 2.53(3H,s), 3.45(3H,s), 7.58–7.69(4H,m), 7.74–7.88(2H,m), 8.14–8.15(1H,m) IR(KBr) cm$^{-1}$: 2220, 1675, 1595, 1582, 1560, 1488

28f) 6-Bromomethyl-2-(2-cyanophenyl)-3-methylquinazolin-4(3H)-one

A solution of the compound obtained in Working Example 28e) (1.66 g), N-bromosuccinimide (1.07 g) and α, α'-azobisisobutyronitrile (0.10 g) in carbon tetrachloride (50 ml) was heated under reflux for 2 hours. After cooling, insoluble materials were removed by filtration and the filtrate was diluted with dichloromethane. The organic phase was washed with water, dried and evaporated in vacuo to afford pale yellow powders (2.1 g, 98%).

$^1$H-NMR(200 MHz,CDCl$_3$) δ: 3.64(3H,s), 4.64(2H,s), 7.61–7.89(6H,m), 8.36(1H,d) IR(KBr) cm$^{-1}$: 2220, 1675, 1599, 1583, 1560, 1487

28g) 2-(2-Cyanophenyl)-6-[[N-(2-methoxycarbonyl-6-nitrophenyl)-N-valeryl]aminomethyl]-3-methyl-quinazolin-4(3H)-one A solution of the compound obtained in Working Example 28f) (2.74 g), methyl 3-nitro-2-valerylaminobenzoate (1.50 g), K$_2$CO$_3$ (1.11 g) and KI (78 mg) in acetonitrile (50 ml) was heated under reflux for 16 hours. In the substantially same manner as in Working Example 25c), the title compound was isolated as pale yellow powders (2.62 g, 88%).

$^1$H-NMR(200MHz,CDCl$_3$) δ: 0.85(3H,t), 1.18–1.35(2H,m), 1.60–1.76(2H,m), 2.12(2H,t), 3.42(3H,s), 3.59(3H,s), 4.67, 5.14(each 1H,d), 7.57–7.70(4H,m), 7.76–7.90(4H,m), 7.99(1H,dd), 8.05(1H,dd) IR(KBr) cm$^{-1}$: 2950, 2225, 1732, 1678, 1599, 1585, 1560, 1533, 1485

28h) Methyl 2-butyl-1-[[2-(2-cyanophenyl)-3-methyl-4-oxo-3,4-dihydroquinazolin-6-yl]methyl]benzimidazole-7-carboxylate In the substantially same manner as in Working Example 25d), the title compound was prepared as white powders (0.984 g, 41%) from the compound (2.60 g) obtained in Working Example 28g).

$^1$H-NMR(200 MHz,CDCl$_3$) δ: 0.95(3H,t), 1.38–1.56(2H,m), 1.82–1.97(2H,m), 2.90(2H,t), 3.42(3H,s), 3.76(3H,s), 5.91(2H,s), 7.20–7.29(3H,m), 7.56–7.87(5H,m), 7.94–8.01(2H,m) IR(KBr) cm$^{-1}$: 2950, 2225, 1712, 1685, 1588, 1560, 1512, 1488

28i) Methyl 2-butyl-1-[[3-methyl-4-oxo-2-[2-(1H-tetrazol-5-yl)phenyl]-3,4-dihydroquinazolin-6-yl]methyl]-benzimidazole-7-carboxylate In the substantially same manner as in Working Example 25e), the title compound was prepared as colorless crystals (0.27 g, 35%) from the compound (0.71 g) obtained in Working Example 28h). m.p. 240°–242° C. (ethyl acetate-methanol).

| Elemental Analysis for C$_{30}$H$_{28}$N$_8$O$_3$.0.3AcOEt: | | | |
|---|---|---|---|
| | C (%) | H (%) | N (%) |
| Calcd.: | 65.17; | 5.33; | 19.49 |
| Found: | 65.01; | 5.35; | 19.26 |

$^1$H-NMR(200 MHz,DMSO-d$_6$) δ: 0.91(3H,t), 1.33–1.52(2H,m), 1.73–1.88(2H,m), 2.95(2H,t), 3.16(3H,s), 3.66(3H,s), 5.83(2H,s), 7.22–7.32(2H,m), 7.43–7.60(3H,m), 7.73–7.80(3H,m), 7.89(1H,d), 8.07–8.12(1H,m) IR(KBr) cm$^{-1}$: 3420, 2960, 2700–2200, 1715, 1672, 1590, 1562

28j) 2-Butyl-1-[[3-methyl-4-oxo-2-[2-(1H-tetrazol-5-yl)phenyl]-3,4-dihydroquinazolin-6-yl]methyl]benzimidazole-7-carboxylic acid A solution of the compound (0.195 g) obtained in Working Example 28i) and 2N aqueous NaOH (3.6 ml) in a mixture of methanol (5 ml), THF (5 ml) and DMF (3 ml) was stirred at room temperature for 43 hours. To the ice-cooled reaction mixture was added 2N aqueous hydrochloric acid (5.0 ml) and the mixture was concentrated to dryness followed by addition of water. The resulting white precipitates were collected by filtration. Recrystallization of the crude crystals from methanol-THF afforded white powders (0.132 g, 70%), m.p. 280°–282° C. (decomp.).

| Elemental Analysis for C$_{29}$H$_{26}$N$_8$O$_3$.0.2THF.0.1H$_2$O: | | | |
|---|---|---|---|
| | C (%) | H (%) | N (%) |
| Calcd.: | 64.98; | 5.09; | 20.34 |
| Found: | 64.90; | 4.92; | 20.05 |

$^1$H-NMR(200 MHz,DMSO-d$_6$) δ: 0.89(3H,t), 1.32–1.50(2H,m), 1.70–1.86(2H,m), 2.91(2H,t), 3.15(3H,S), 6.00(2H,s), 7.23–7.65(5H,m), 7.72–7.90(4H,m), 8.08–8.13(1H,m) IR(KBr) cm$^{-1}$: 3420, 2955, 2700–2200, 1695, 1678, 1587, 1552, 1490

Working Example 29

2-Butyl-1-[[2-[2-(1H-tetrazol-5-yl)phenyl]quinazolin-6-yl]methyl]benzimidazole-7-carboxylic acid 29a) 2-(2-Bromophenyl)-4-chloro-6-methylquinazoline A mixture of the compound (7.0 g) obtained in Working Example 28c) and phosphorous oxychloride (21 ml) was stirred at 100° C. for 2 hours. After cooling, the mixture was concentrated in vacuo to dryness. The residue was neutralized with ice and 2N aqueous NaOH and the mixture was extracted with dichloromethane. The extract was washed with water, dried and the solvent was evaporated in vacuo. The residue was purified by column chromatography on silica gel to afford white powders (7.1 g, 96%), m.p. 112°–113° C.

$^1$H-NMR(200 MHz,CDCl$_3$) δ: 2.6(3H,s), 7.27–7.49(2H,m), 7.70–7.85(3H,m), 8.02–8.09(2H,m) IR(KBr) cm$^{-1}$: 1585, 1555, 1545, 1488

29b) 2-(2-Bromophenyl)-6-methylquinazoline

To a solution of the compound (7.0 g) obtained in Working Example 29a) in chloroform (150 ml) was added p-toluenesulfonic hydrazide (5.9 g) and the mixture was heated under reflux for 14 hours. After cooling, the reaction mixture was concentrated to dryness. To a suspension of the resulting residue in a mixture of ethylene glycol (70 ml) and water (30 ml) was added 1N aqueous NaOH (53 ml) and the mixture was stirred at 100° C. for 1.5 hours. After cooling, the reaction mixture was diluted with aqueous sodium bicarbonate and extracted with chloroform. The extract was washed with water, dried and evaporated in vacuo. The residue was purified by column chromatography on silica gel to afford pale brown solids (4.3 g, 69%), m.p. 70°–71° C.

$^1$H-NMR(200 MHz,CDCl$_3$) δ: 2.61(3H,s), 7.27–7.50(2H,m), 7.71–7.82(4H,m), 8.03(1H,d), 9.44(1H,s) IR(KBr) cm$^{-1}$: 1570, 1552, 1490 SI-MS m/z: 299(MH+; $^{79}$Br), (MH$^{30}$; $^{81}$Br).

29c) 2-(2-Cyanophenyl)-6-methylquinazoline

In the substantially same manner as in Working Example 28e), the title compound was prepared as yellowish needles (2.06 g, 68%) from the compound (3.7 g) obtained in Working Example 29b). m.p. 174°–176° C. (ethyl acetate).

| Elemental Analysis for C$_{16}$H$_{11}$N$_3$: | | | |
|---|---|---|---|
| | C (%) | H (%) | N (%) |
| Calcd.: | 78.35; | 4.52; | 17.13 |
| Found: | 78.11; | 4.54; | 17.05 |

$^1$H-NMR(200 MHz,CDCl$_3$) δ: 2.61(3H,s), 7.57(1H,dt), 7.70–7.91(4H,m), 8.09(1H,d), 8.50(1H,dd), 9.46(1H,s) IR(KBr) cm$^{-1}$: 2220, 1575, 1555, 1485, SI-MS m/z: 246(MH+).

29d) 6-Methyl-2-[2-(N-triphenylmethyltetrazol-5-yl)phenyl]quinazoline

To a solution of the compound obtained in Example 29c) (2.0 g) in toluene (100 ml) was added trimethyltin azide (8.43 g) and the reaction mixture was heated under reflux for 5 days. After cooling, the reaction mixture was concentrated to dryness. To an ice-cooled suspension of the resulting residue in methanol (150 ml) was added conc. hydrochloric acid (2.7 ml) and the mixture was stirred at room temperature for 17 hours and concentrated to dryness. The concentrate was partitioned between water and ethyl acetate-THF and the resulting white powders were collected by filtration, washed with ethyl acetate and dried in vacuo. To the aqueous phase was added 2N aqueous NaOH (16 ml) and the mixture was extracted with ethyl acetate-THF. The organic phases were combined, washed with water, dried and evaporated in vacuo.

To a solution of the resulting residue, the white powders thus obtained and triphenylchloromethane (3.4 g) in DMF (20 ml) was added triethylamine (2.3 ml) and the mixture was stirred at room temperature for 2 hours.

The reaction mixture was diluted with ice-water and extracted with ethyl acetate. The extract was washed with water, dried and evaporated in vacuo. The residue was purified by column chromatography on silica gel. Recrystallization from ethyl acetate-hexane afforded colorless crystals (3.53 g, 81%), m.p. 174°–179° C.

| Elemental Analysis for C$_{35}$H$_{26}$N$_6$: | | | |
|---|---|---|---|
| | C (%) | H (%) | N (%) |
| Calcd.: | 79.22; | 4.94; | 15.84 |
| Found: | 79.03; | 4.94; | 15.81 |

$^1$H-NMR(200 MHz,CDCl$_3$) δ: 2.57(3H,s), 6.85–6.91(6H,m), 7.10–7.28(9H,m), 7.50–7.89(6H,m), 8.11–8.16(1H,m), 8.91(1H,s) RI(KBr) cm$^{-1}$: 1570, 1555, 1490

29e) 6-Bromomethyl-2-[2-(N-triphenylmethyltetrazol-5-yl)phenyl]quinazoline

In the substantially same manner as in Working Example 28f), the title compound was prepared as pale yellow powders (2.1 g, 91%) from the compound (2.0 g) obtained in Working Example 29d).

$^1$H-NMR(200 Mz,CDCl$_3$) δ: 4.66(2H,s), 6.85–6.89(6H,m), 7.11–7.29(9H,m), 7.57–7.89(6H,m), 8.16–8.20(1H,m), 8.96(1H,s) IR(KBr) cm$^{-1}$: 1570, 1555, 1490

29f) 6-[[N-(2-methoxycarbonyl-6-nitrophenyl)-N-valeryl]aminomethyl]-2-[2-(N-triphenylmethyltetrazol-5-yl)phenyl]quinazoline To an ice-cooled solution of methyl 3-nitro-2-valerylaminobenzoate (0.95 g) in DMF (8 ml) under N$_2$ was added sodium hydride (60% dispersion in mineral oil, 0.136 g) and the mixture was stirred at the same temperature for 30 minutes. To the reaction mixture was added dropwise a solution of the compound (2.1 g) obtained in Working Example 29e) in DMF (15 ml) and the mixture was stirred at room temperature for 4 hours. After evaporation of the solvent, the residue was extracted with ethyl acetate. The extract was washed with water, dried and concentrated to dryness. The residue was purified by column chromatography on silica gel to afford pale yellow powders (2.0 g, 73%).

$^1$H-NMR(200 MHz,CDCl$_3$) δ: 0.86(3H,t), 1.18–1.37(2H,m), 1.61–1.77(2H,m), 2.13(2H,t), 3.42(3H,s), 4.71, 5.12(each 1H,d), 6.89–6.95(6H,m), 7.12–7.29(9H,m), 7.43–7.79(6H,m), 7.89–8.09(4H,m), 8.90(1H,s) IR(KBr) cm$^{-1}$: 2950, 1730, 1670, 1570, 1555, 1530

29g) Methyl 2-butyl-1-[[2-[2-(1H-tetrazol-5-yl)phenyl]-quinazoline-6-yl]methyl]benzimidazole-7-carboxylate A mixture of the compound (1.70 g) obtained in Working Example 29f), iron powders (0.38 g) in a mixture of acetic acid (4 ml) and methanol (40 ml) was heated under reflux for 8 hours. After cooling, the reaction mixture was concentrated to dryness, the residue was suspended in acetic acid (50 ml) and the suspension was stirred at 80°–90° C. for 8 hours. Insoluble materials were filtered off through a pad of Celite and the filtrate was concentrated to dryness. The residue was extracted with ethyl acetate and the extract was washed with water, dried and concentrated to dryness. The residue was dissolved in a mixture of methanol (20 ml) and THF (10 ml) followed by addition of 1N hydrochloric acid (10.5 ml) and the mixture was stirred at room temperature for 3 hours. After the reaction mixture was concentrated to dryness, the concentrate was extracted with ethyl acetate. The extract was washed with water, dried and concentrated to dryness. The residue was purified by column chromatography on silica gel. Recrystallization from dichloromethane-hexane afforded colorless powders (0.53 g, 49%), m.p. 129°–131° C.

| Elemental Analysis for $C_{29}H_{26}N_8O_2 \cdot 0.1H_2O$: | | | |
|---|---|---|---|
| | C (%) | H (%) | N (%) |
| Calcd.: | 66.94; | 5.07; | 21.53 |
| Found: | 66.74; | 5.23; | 21.32 |

$^1$H-NMR(200 MHz,CDCl$_3$) δ: 0.89(3H,t), 1.30–1.48(2H,m), 1.73–1.88(2H,m), 2.79(2H,t), 3.68(3H,s), 5.99(2H,s), 7.17–7.25(2H,m), 7.65–7.73(4H,m), 7.86(1H,dd), 8.01(1H,d), 8.19–8.30(2H,m), 9.25(1H,s) IR(KBr) cm$^{-1}$: 2960, 2700-2200, 1715, 1575, 1560, 1515 SI-MS m/z: 519(MH$^+$).

29h) 2-Butyl-1-[[2-[2-(1H-tetrazol-5-yl)phenyl]quinazoline-6-yl]methyl]benzimidazole-7-carboxylic acid In the substantially same manner as in Working Example 28j), the title compound was prepared as colorless crystals (0.106 g, 73%) from the compound (0.15 g) obtained in Working Example 29g). m.p. 188°–191° C. (ethyl acetate-ether).

| Elemental Analysis for $C_{28}H_{24}N_8O_2 \cdot 0.1H_2O$: | | | |
|---|---|---|---|
| | C (%) | H (%) | N (%) |
| Calcd.: | 66.42; | 4.82; | 22.13 |
| Found: | 66.30; | 4.71; | 21.92 |

$^1$H-NMR(200 MHz,DMSO-d$_6$) δ: 0.87(3H,t), 1.31–1.50(2H,m), 1.71–1.86(2H,m), 2.91(2H,t), 6.03(2H,s), 7.25(1H,t), 7.44–7.90(8H,m), 8.24(1H,d), 9.38(1H,s) IR(KBr) cm$^{-1}$: 3420, 2960, 2700-2200, 1700, 1600, 1578, 1560, 1520, 1490

Working Example 30

Pivaloyloxymethyl 2-butyl-1-[[2-[2-(1H-tetrazol-5-yl)phenyl]quinazoline-6-yl]methyl]benzimidazole-7-carboxylate 30a) Pivaloyloxymethyl 2-butyl-1-[[2-[2-(N-triphenylmethyltetrazol-5-yl)phenyl]quinazoline-6-yl]methyl]benzimidazole-7-carboxylate To a solution of the compound (0.196 g) obtained in Working Example 29h), triphenylmethyl chloride (0.13 g) in DMF (4 ml) was added triethylamine (60 μl) and the mixture was stirred at room temperature for 4 hours. After the mixture was concentrated to dryness, the residue was diluted with water and extracted with ethyl acetate. The extract was washed with water, dried and concentrated to dryness. To an ice-cooled solution of the resulting residue in DMF (4 ml) was added potassium carbonate (81 mg) and pivaloyloxymethyl iodide (0.14 ml) and the mixture was stirred at room temperature for 18 hours. After the mixture was concentrated to dryness, the residue was diluted with water and extracted with ethyl acetate. The extract was washed with water, dried and concentrated to dryness. The residue was purified by column chromatography on silica gel to afford white powders (0.21 g, 63%).

$^1$H-NMR(200 MHz,CDCl$_3$) δ: 0.91(3H,t), 1.10(9H,s), 1.34–1.53(2H,m), 1.83–1.98(2H,m), 2.82(2H,t), 5.74(2H,s), 6.06(2H,s), 6.83–6.96(7H,m), 7.07–7.38(10H,m), 7.55–7.61(3H,m), 7.82–7.91(3H,m), 8.06–8.12(2H,m), 8.71(1H,s) IR(KBr) cm$^{-1}$: 2960, 1750, 1730, 1575, 1558, 1522, 1490

30b) Pivaloyloxymethyl 2-butyl-1-[[2-[2-(1H-tetrazol-5-yl)phenyl]quinazoline-6-yl]methyl]benzimidazole-7-carboxylate A solution of the pivaloyloxymethyl ester (0.20 g) obtained in Working Example 30a) in a mixture of 2N hydrochloric acid (2.4 ml), methanol (4 ml) and THF (4 ml) was stirred at room temperature for 4.5 hours. To the reaction mixture was added 1N aqueous sodium hydroxide (3.5 ml) and the mixture was extracted with ethyl acetate. The extract was washed with water, dried and concentrated to dryness. The residue was purified by column chromatography on silica gel to give crystals. Recrystallization from ethyl acetate-isopropyl ether afforded colorless crystals (0.115 g, 80%), m.p. 126°–128° C.

| Elemental Analysis for $C_{34}H_{34}N_8O_4 \cdot 0.5H_2O$: | | | |
|---|---|---|---|
| | C (%) | H (%) | N (%) |
| Calcd.: | 65.06; | 5.62; | 17.85 |
| Found: | 64.80; | 5.78; | 17.64 |

$^1$H-NMR(200 MHz,CDCl$_3$) δ: 0.91(3H,t), 1.06(9H,s), 1.34–1.52(2H,m), 1.77–1.93(2H,m), 2.83(2H,t), 5.73(2H,s), 6.05(2H,s), 7.22–7.33(2H,m), 7.66–7.80(4H,m), 7.96–8.08(2H,m), 8.25–8.32(2H,m), 9.30(1H,s) IR(KBr) cm$^{-1}$: 3430, 2960, 2700-2200, 1750, 1732, 1575, 1560, 1522

Formulation Examples

When the compound (I) of the present invention is used as a therapeutic agent for circulatory failures such as hypertension, heart diseases, strokes, kidney diseases, etc., it can be used in accordance with, for example, the following formulations.

1. Capsules

| | | |
|---|---|---|
| (1) | 7-methyl-2-propyl-3-[[2'-(1H-tetrazol-5-yl)biphenyl-4-yl]methyl]-3H-imidazo[4,5-c]pyridine-4-carboxylic acid | 10 mg |
| (2) | lactose | 90 mg |
| (3) | fine crystalline cellulose | 70 mg |
| (4) | magnesium stearate | 10 mg |
| | one capsule | 180 mg |

(1), (2), (3) and a half of (4) are mixed and granulated. To the granules is added the remainder of (4), and the whole is filled into gelatin capsules.

2. Tablets

| | | |
|---|---|---|
| (1) | 7-methyl-2-propyl-3-[[2'-(1H-tetrazol-5-yl)biphenyl-4-yl]methyl]-3H-imidazo[4,5-c]pyridine-4-carboxylic acid | 10 mg |
| (2) | lactose | 35 mg |
| (3) | corn starch | 150 mg |
| (4) | fine crystalline cellulose | 30 mg |
| (5) | magnesium stearate | 5 mg |
| | one tablet | 230 mg |

(1), (2), (3), two thirds of (4) and a half of (5) are mixed and granulated. To the granules are added the remainders of (4) and (5), followed by subjecting the granules to compression molding.

| 3. Injections | |
|---|---|
| (1) 7-methyl-2-propyl-3-[[2'-(1H-tetrazol-5-yl)biphenyl-4-yl]methyl]-3H-imidazo[4,5-c]pyridine-4-carboxylic acid sodium salt | 10 mg |
| (2) inositol | 100 mg |
| (3) benzyl alcohol | 20 mg |
| one ampoule | 130 mg |

(1), (2) and (3) are dissolved in distilled water for injection to make the whole volume 2 ml, which is filled into an ampoule. The whole process is conducted under sterile conditions.

| 4. Capsules | |
|---|---|
| (1) 2-ethyl-4-oxo-9-[[2'-(1H-tetrazol-5-yl)biphenyl-4-yl]methyl]-4,9-dihydrothieno[2,3-b]quinoline-8-carboxylic acid | 10 mg |
| (2) lactose | 90 mg |
| (3) fine crystalline cellulose | 70 mg |
| (4) magnesium stearate | 10 mg |
| one capsule | 180 mg |

(1), (2), (3) and a half of (4) are mixed and granulated. To the granules is added the remainder of (4), and the whole is filled into gelatin capsules.

Experimental Example 1

Inhibition of Binding of AngiotensinII to Angiotensin receptor

[Method]

An experiment of inhibition on the binding of angiotensinII (AII) to AII receptor was conducted by modifying the method of Douglas et al. [Endocrinology, 102, 685–696 (1978)]. An AII receptor membrane fraction was prepared from bovine adrenal cortex.

The compound of the present invention ($10^{-6}$M or $10^{-7}$M) and [$^{125}$I]-angiotensinII ([$^{125}$I]-AII) (1.85 kBq/50 μl) were added to the receptor membrane fraction, and the mixture was incubated at room temperature for one hour. The receptor-bound and free [$^{125}$I]-AII were separated through a filter (Whatman GF/B filter), and the radioactivity of [$^{125}$I]-AII bound to the receptor was measured.

[Results]

The results relating to the compounds of the present invention are shown in Table 1.

Experimental Example 2

Inhibitory Effect of the Compound of the Pesent Invention on Pressor Action of AII

[Method]

Jcl: SD rats (9 week old, male) were employed. On the day previous to that of the experiment, these animals were applied with cannulation into the femoral artery and vein under anesthesia with pentobarbital Na. The animals were fasted but allowed access freely to drinking water until the experiment was started. On the day of conducting the experiment, the artery cannula was connected with a blood-pressure transducer, and the average blood pressure was recorded by means of polygraph. Before administration of the drug, the pressor action due to intravenous administration of AII (100 ng/kg) as the control was measured. The drugs were orally administered, then, at each point of the measurement, AII was administered intravenously, and the pressor action was similarly measured. By comparing the pressor action before and after administration of the drug, the percent inhibition by the drug on AII-induced pressor action was evaluated.

[Results]

The results relating to the compounds of the present invention are shown in Table 1.

TABLE 1

| Ex. No. | Formula | A II Antagonistic Activity | | Pressor Res. to A II |
|---|---|---|---|---|
| | | Radioreceptor Assay (%) | | |
| | | $10^{-7}$ (M) | $10^{-6}$ (M) | 10 mg/kg, P.O. |
| 1 | (structure shown) | 63 | 92 | N T |

TABLE 1-continued
A II Antagonistic Activity
| Ex. No. | Formula | Radioreceptor Assay (%) | | Pressor Res. to A II |
|---|---|---|---|---|
| | | $10^{-7}$ (M) | $10^{-6}$ (M) | 10 mg/kg, P.O. |
| 2 | 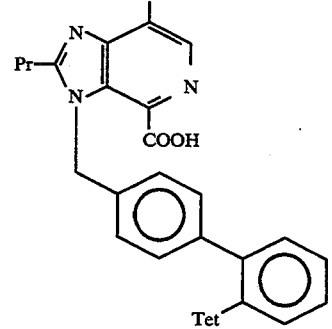 | 54 | 92 | +++ |
| 3 | 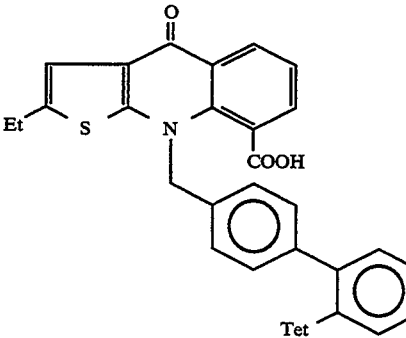 | 12 | 49 | +++ |
| 6 | 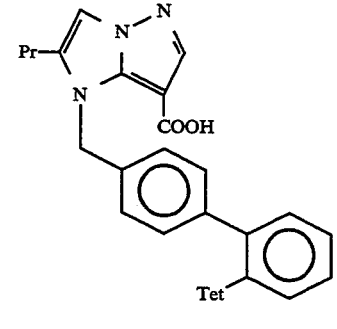 | 60 | 91 | +++ |
| 7 | 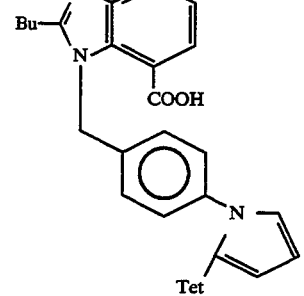 | 27 | 67 | N T |

TABLE 1-continued
A II Antagonistic Activity
| Ex. No. | Formula | Radioreceptor Assay (%) | | Pressor Res. to A II |
|---|---|---|---|---|
| | | $10^{-7}$ (M) | $10^{-6}$ (M) | 10 mg/kg, P.O. |
| 11 | 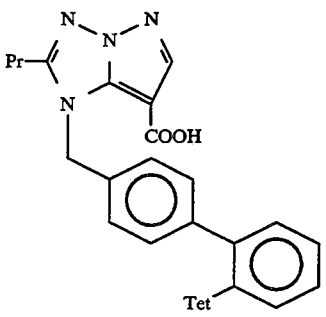 | 54 | 86 | +++ |
| 13 | 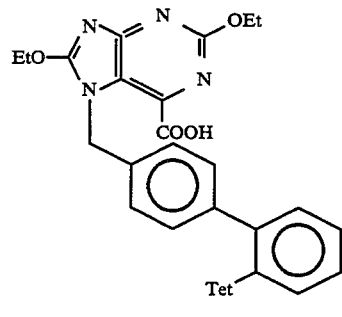 | 20 | 49 | + |
| 14 | 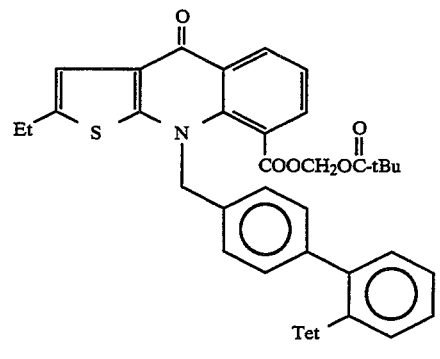 | 31 | 69 | +++ |
| 15 | 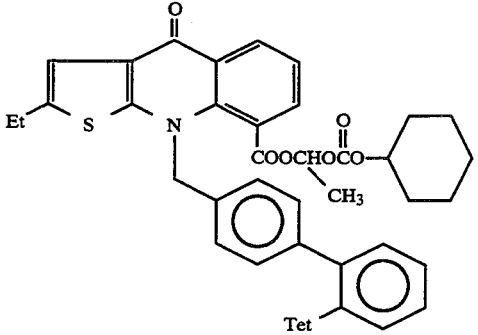 | 1 | 19 | +++ |

TABLE 1-continued

| Ex. No. | Formula | A II Antagonistic Activity | | Pressor Res. to A II |
|---|---|---|---|---|
| | | Radioreceptor Assay (%) | | |
| | | $10^{-7}$ (M) | $10^{-6}$ (M) | 10 mg/kg, P.O. |
| 17 | (structure: 2-Pr-indole-N-CH2-biphenyl-Tet) | 0 | 39 | N T |
| 20 | (structure: Pr-triazole with COOCH2OC(O)—OtBu, CH2-biphenyl-Tet) | 21 | 61 | +++ |
| 21 | (structure: 2-Bu-benzimidazole-COOH, N-CH2-pyridine-phenyl-Tet) | 26 | 70 | +++ |
| 26 | (structure: 2-Bu-benzimidazole-COOH, N-CH2-phenyl-quinazolinone-N-phenyl-Tet) | 39 | 80 | + |

What is claimed is:

1. A compound of the formula:

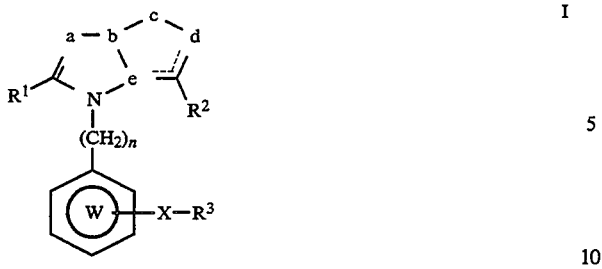

wherein $R^1$ is lower ($C_{1-8}$) alkyl, lower ($C_{2-8}$) alkenyl, lower ($C_{2-8}$) alkynyl, $C_{3-6}$ cycloalkyl, phenyl-lower ($C_{1-4}$) alkyl, phenyl or napthyl, which may be attached through (a) —N($R^{10}$)— wherein $R^{10}$ is hydrogen or lower ($C_{1-4}$) alkyl, (b) oxygen or (c) $S(O)_m$ wherein m is an integer of 0 to 2, each of the lower alkyl, lower alkenyl, lower alkynyl and cycloalkyl being unsubstituted or substituted with hydroxyl, amino, N-lower ($C_{1-4}$) alkylamino, N,N-di-lower ($C_{1-4}$) alkylamino, halogen, lower ($C_{1-4}$) alkoxy or lower ($C_{1-4}$) alkylthio, and each of the phenyl-lower alkyl, phenyl and naphthyl groups being unsubstituted or substituted with halogen, amino, N-lower ($C_{1-4}$) alkylamino, N,N-di-lower ($C_{1-4}$) alkylamino, lower ($C_{1-4}$) alkoxy, lower ($C_{1-4}$) alkylthio or lower ($C_{1-4}$) alkyl on the benzene ring;

$R^2$ is a group of the formula —CO—D, wherein D is (i) hydroxyl, (ii) lower ($C_{1-6}$) alkoxy, or (iii) a group of the formula —OCH($R^4$)OCOR$^5$, wherein $R^4$ is hydrogen or lower ($C_{1-6}$) alkyl and $R^5$ is lower ($C_{1-6}$) alkyl, lower ($C_{1-6}$) alkoxy or $C_{3-8}$ cycloalkyloxy;

$R^3$ is phenyl which is substituted with $R^6$ selected from the group consisting of carboxyl, tetrazolyl, trifluoromethanesulfonic amide (—NHSO$_2$CF$_3$), phosphoric acid, sulfonic acid, cyano, and lower ($C_{1-4}$) alkoxycarbonyl, each of the groups being unprotected or protected with (i) lower ($C_{1-4}$) alkyl group, which may be substituted with lower ($C_{1-4}$) alkoxy or phenyl, (ii) —OCH($R^{4'}$)OCOR$^{5'}$ wherein $R^{4'}$ is hydrogen, lower ($C_{1-6}$) alkyl or $C_{3-8}$ cycloalkyl and $R^{5'}$ is (a) lower ($c_{1-6}$) alkyl, (b) lower ($C_{2-8}$) alkenyl, (c) $C_{3-8}$ cycloalkyl, (d) lower ($C_{1-3}$) alkyl which is substituted with phenyl or $C_{3-8}$ cycloalkyl, (e) lower ($C_{2-3}$) alkenyl which is substituted with phenyl or $C_{3-8}$ cycloalkyl, (f) phenyl, (g) p-tolyl (h) naphthyl, (i) lower ($C_{1-6}$) alkoxy, (j) lower ($C_{2-8}$) alkenyloxy, (k) $C_{3-8}$ cycloalkyloxy, (l) lower ($C_{1-3}$) alkoxy which is substituted with phenyl or $C_{3-8}$ cycloalkyl, (m) lower ($C_{2-3}$) alkenyloxy which is substituted with phenyl or $C_{3-8}$ cycloalkyl, (n) phenoxy, (o) p-nitrophenoxy or (p) naphthoxy, (iii) lower ($C_{2-5}$) alkanoyl or (iv) benzoyl, the phenyl $R^3$ group being optionally further substituted with a substituent selected from halogen, nitro, cyano, lower ($C_{1-4}$) alkoxy, amino, N-lower ($C_{1-4}$) alkylamino, N,N-di-lower ($C_{1-4}$) alkylamino, lower ($C_{1-4}$) alkylthio and lower ($C_{1-4}$) alkyl;

X is (i) a chemical bond, (ii) lower ($C_{1-4}$) alkylene wherein the number of atoms between the W ring and $R^3$ is 1 or 2, (iii) —CO—, (iv) —O—, (v) —S—, (vi) —NH—, (vii) —CO—NH—, (viii) —O—CH$_2$—, (ix) —S—CH$_2$—, or (x) —CH=CH—;

W is phenyl which may be substituted with halogen, nitro, cyano, lower ($C_{1-4}$) alkoxy, amino, N-lower ($C_{1-4}$) alkylamino, N,N-di-lower ($C_{1-4}$) alkylamino, lower ($C_{1-4}$) alkylthio, and lower ($C_{1-4}$) alkyl; a, c and d are independently selected from the group consisting of one or two optionally substituted carbon atoms and one or two optionally substituted hetero atoms; b and e are independently selected from the group consisting of one optionally substituted carbon atom and one optionally substituted nitrogen atom, wherein one of b or e is nitrogen; the dotted line is a bond to form one double bond; n is an integer of 1 or 2; or a pharmaceutically acceptable salt thereof.

2. A compound of the formula:

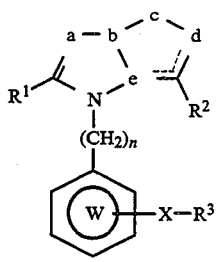

I wherein the heterocyclic group of the formula:

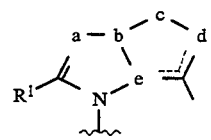

is selected from the group consisting of

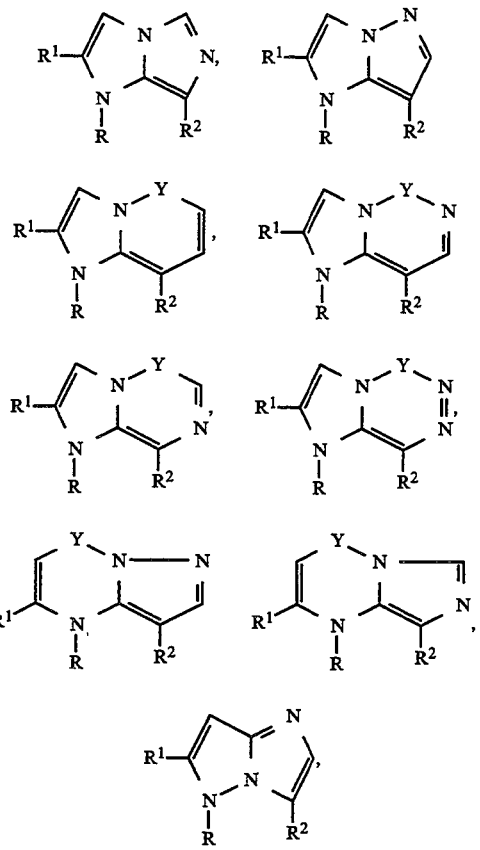

-continued

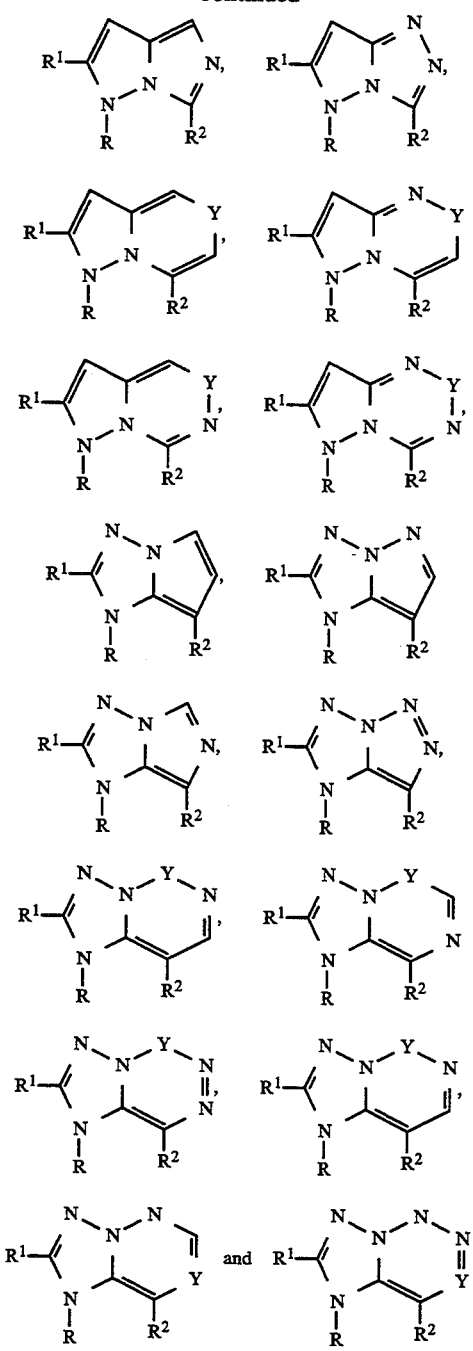

wherein R is

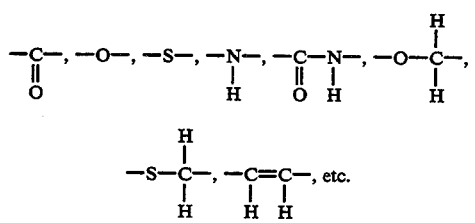

Y is —CH$_2$—, —CO—, —NR$^{11}$— wherein R$^{11}$ is hydrogen or C$_{1-4}$ lower alkyl —O—, or —S—; R$^1$ is lower (C$_{1-8}$) alkyl, lower (C$_{2-8}$) alkenyl, lower (C$_{2-8}$) alkynyl, C$_{3-6}$ cycloalkyl, phenyl-lower (C$_{1-4}$) alkyl, phenyl or naphthyl, which may be attached through (a) —N(R$^{10}$)—wherein R$^{10}$ is hydrogen or lower ($_{1-4}$) alkyl, (b) oxygen or (c) S(O)$_m$ wherein m is an integer of 0 to 2, each of the lower alkyl, lower alkenyl, lower alkynyl and cycloalkyl being unsubstituted or substituted with hydroxyl, amino, N-lower (C$_{1-4}$) alkylamino, N,N-di-lower (C$_{1-4}$) alkylamino, halogen, lower (C$_{1-4}$) alkoxy or lower (C$_{1-4}$) alkylthio, and each of the phenyl-lower alkyl, phenyl and naphthyl groups being unsubstituted or substituted with halogen, amino, N-lower (C$_{1-4}$) alkylamino, N,N-di-lower (C$_{1-4}$) alkylamino, lower (C$_{1-4}$) alkoxy, lower (C$_{1-4}$) alkylthio or lower (C$_{1-4}$) alkyl on the benzene ring;

R$^2$ is a group of the formula —CO—D, wherein D is (i) hydroxyl, (ii) lower (C$_{1-6}$) alkoxy, or (iii) a group of the formula —OCH(R$^4$)OCOR$^5$, wherein R$^4$ is hydrogen or lower (C$_{1-6}$) alkyl and R$^5$ is lower (C$_{1-6}$) alkyl, lower (C$_{1-6}$) alkoxy or C$_{3-8}$ cycloalkyloxy;

R$^3$ is phenyl which is substituted with R$^6$ selected from the group consisting of carboxyl, tetrazolyl, trifluoromethanesulfonic amide (—NHSO$_2$CF$_3$), phosphoric acid, sulfonic acid, cyano, and lower (C$_{1-4}$) alkoxycarbonyl, each of the groups being unprotected or protected with (i) lower (C$_{1-4}$) alkyl group, which may be substituted with lower (C$_{1-4}$) alkoxy or phenyl, (ii) —OCH(R$^{4'}$)OCOR$^{5'}$ wherein R$^{4'}$ is hydrogen, lower (C$_{11-6}$) alkyl or C$_{3-8}$ cycloalkyl and R$^{5'}$ is (a) lower (c$_{1-6}$) alkyl, (b) lower (C$_{2-8}$) alkenyl, (c) C$_{3-8}$ cycloalkyl, (d) lower (C$_{1-3}$) alkyl which is substituted with phenyl or C$_{3-8}$ cycloalkyl, (e) lower (C$_{2-3}$) alkenyl which is substituted with phenyl or C$_{3-8}$ cycloalkyl, (f) phenyl, (g) p-tolyl (h) naphthyl, (i) lower (C$_{1-6}$) alkoxy, (j) lower (C$_{2-8}$) alkenyloxy, (k) C$_{3-8}$ cycloalkyloxy, (1) lower (C$_{1-3}$) alkoxy which is substituted with phenyl or C$_{3-8}$ cycloalkyl, (m) lower (C$_{2-3}$) alkenyloxy which is substituted with phenyl or C$_{3-8}$ cycloalkyl, (n) phenoxy, (o) p-nitrophenoxy or (p) naphthoxy, (iii) lower (C$_{2-5}$) alkanoyl or (iv) benzoyl, the phenyl R$^3$ group being optionally further substituted with a substituent selected from halogen, nitro, cyano, lower (C$_{1-4}$) alkoxy, amino, N-lower (C$_{1-4}$) alkylamino, N,N-di-lower (C$_{1-4}$) alkylamino, lower (C$_{1-4}$) alkylthio and lower (C$_{1-4}$) alkyl;

X is (i) a chemical bond, (ii) lower (C$_{1-4}$) alkylene wherein the number of atoms between the W ring and R$^3$ is 1 or 2, (iii) —CO—, (iv) —O—, (v) —S—, (vi) —NH—, (vii) —CO—NH—, (viii) —O—CH$_2$—, (ix) —S—CH$_2$—, or (x) —CH═CH—;

W is phenyl which may be substituted with halogen, nitro, cyano, lower (C$_{1-4}$) alkoxy, amino, N-lower (C$_{1-4}$) alkylamino, N,N-di-lower (C$_{1-4}$) alkylamino, lower (C$_{1-4}$) alkylthio, and lower (C$_{1-4}$) alkyl; the dotted line is a bond to form one double bond; n is an integer of 1 or 2; or a pharmaceutically acceptable salt thereof.

3. A compound according to claim 1, which is a compound of the formula (I'):

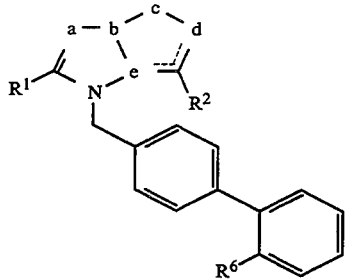

wherein R¹ is lower (C₂₋₄) alkyl wherein the methylene group attached to the condensed heterocyclic ring system may be replaced with a hetero atom selected from the group consisting of O, N and S; R² is a group of the formula —CO—D' wherein D' is hydroxyl, lower (C₁₋₄) alkoxy optionally substituted by lower (C₂₋₆) alkanoyloxy or 1-lower (C₁₋₆) alkoxycarbonyloxy;

R⁶ is (i) tetrazolyl optionally protected with lower (C₁₋₄) alkyl, lower (C₁₋₄) alkoxy-lower (C₁₋₄) alkyl, triphenylmethyl, p-methoxybenzyl, p-nitrobenzyl, lower (C₂₋₅) alkanoyl or benzoyl, or (ii) carboxyl optionally protected with lower (C₁₋₄) alkyl, lower (C₁₋₄) alkoxy-lower (C₁₋₄) alkyl, triphenylmethyl, p-methoxybenzyl, or p-nitrobenzyl, the fused heterocyclic ring of the formula:

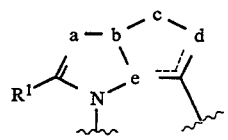

is selected from

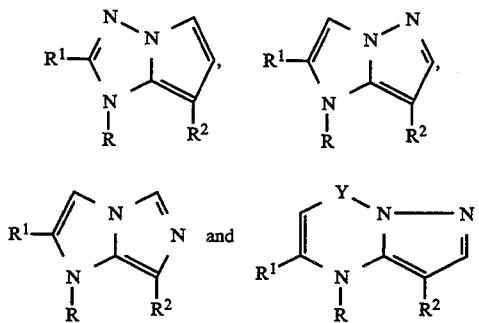

wherein R is a group of the formula:

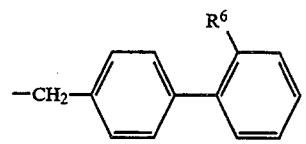

and Y is —CH₂—, —CO—, —O—, —S— or —NR¹¹— wherein R¹¹ is hydrogen or lower (C₁₋₄) alkyl; or a pharmaceutically acceptable salt thereof.

4. A compound according to claim 1, wherein the W ring is phenyl.

5. A compound according to claim 1, wherein R¹ is a lower (C₁₋₈) alkyl or (C₂₋₈) alkenyl group which may be substituted with hydroxy, amino, N-lower (C₁₋₄) alkylamino, N,N-di-lower (C₁₋₄) alkylamino, halogen, lower (C₁₋₄) alkoxy or lower (C₁₋₄) alkylthio.

6. A compound according to claim 1, wherein R² is carboxyl.

7. A compound according to claim 1, wherein R³ is phenyl substituted with a tetrazolyl group.

8. A compound according to claim 1, wherein X is a chemical bond between the ring W group and the the R³ group.

9. A compound which is 2-butyl-7-methyl-3-[[2'-(1H-tetrazol-5-yl)biphenyl-4-yl]methyl]-3H-imidazol[4,5-c]pyridine-4-carboxylic acid or a pharmaceutically acceptable salt thereof.

10. A compound which is 2-propyl-7-methyl-3-[[2'-(1H-tetrazol-5-yl)biphenyl-4-yl]methyl]-3H-imidazo[4,5-c]pyridine-4-carboxylic acid or a pharmaceutically acceptable salt thereof.

11. A compound which is 5-propyl-4-[[2'-(1H-tetrazol-5-yl)biphenyl-4-yl]methyl]-imidazo[1,2-b]pyrazol-3-carboxylic acid or a pharmaceutically acceptable salt thereof.

12. A compound which is 2-propyl-1-[[2'-(1H-tetrazol-5-yl)biphenyl-4-yl]methyl]-1H-pyrazolo[1,5-b][1,2,4]triazole-7-carboxylic acid or a pharmaceutically acceptable salt thereof.

13. A compound which is 2-butyl-1-[[2-[2-(1H-tetrazol-5-yl)phenyl]pyridin-5-yl]methyl]benzimidazole-7-carboxylic acid or a pharmaceutically acceptable salt thereof.

14. A pharmaceutical composition for antagonizing angiotensinII which comprises a therapeutically effective amount of a compound according to claim 1 or a pharmaceutically acceptable salt thereof in admixture with a pharmaceutical acceptable carrier, excipient or diluent.

* * * * *